US008883419B2

(12) United States Patent
Somasundaram et al.

(10) Patent No.: US 8,883,419 B2
(45) Date of Patent: Nov. 11, 2014

(54) METHODS AND KITS USEFUL FOR THE IDENTIFICATION OF ASTROCYTOMA, IT'S GRADES AND GLIOBLASTOMA PROGNOSIS

(75) Inventors: Kumaravel Somasundaram, Bangalore (IN); Paturu Kondaiah, Bangalore (IN); Vani Santosh, Bangalore (IN); Anandh Balasubramaniam, Bangalore (IN); Alangar Sathyaranjandas Hedge, Bangalore (IN); Ashwathnarayana Rao Chandramouli, Bangalore (IN); Manchanahalli Rangaswamy Sathyanarayana Rao, Bangalore (IN)

(73) Assignee: Council of Scientific & Industrial Research, New Delhi (IN)

( * ) Notice: Subject to any disclaimer, the term of this patent is extended or adjusted under 35 U.S.C. 154(b) by 1157 days.

(21) Appl. No.: 12/811,976

(22) PCT Filed: Jan. 6, 2009

(86) PCT No.: PCT/IN2009/000017
§ 371 (c)(1),
(2), (4) Date: Sep. 29, 2010

(87) PCT Pub. No.: WO2009/087689
PCT Pub. Date: Jul. 16, 2009

(65) Prior Publication Data
US 2011/0027784 A1 Feb. 3, 2011

(30) Foreign Application Priority Data

Jan. 7, 2008 (IN) ............................ 0054/DEL/2008
Jan. 7, 2008 (IN) ............................ 0055/DEL/2008

(51) Int. Cl.
*C12Q 1/68* (2006.01)
*C12P 19/34* (2006.01)
(52) U.S. Cl.
CPC ........ *C12Q 1/6886* (2013.01); *C12Q 2600/118* (2013.01); *C12Q 2600/112* (2013.01); *C12Q 2600/158* (2013.01)
USPC ...................................... 435/6.12; 435/91.2
(58) Field of Classification Search
USPC ................................................ 435/6.12, 91.2
See application file for complete search history.

(56) References Cited

U.S. PATENT DOCUMENTS

2004/0053277 A1    3/2004  Zhang et al. ..................... 435/6
2007/0072216 A1*   3/2007  Somasundaram et al. ........ 435/6
2010/0322949 A1*  12/2010  Caballero et al. ........... 424/174.1

FOREIGN PATENT DOCUMENTS

WO       WO 02/40716        5/2002
WO       WO 2007/111733    10/2007
WO          2009/014565  *  1/2009

OTHER PUBLICATIONS

Brock et al., "Current perspectives in gliomas," *Medical Oncology*, 14:103-120, 1997.
De Girolami et al., "Chapter 29: The Central Nervous System," In: *Pathologic basis of disease*, 5th ed., Phildelphia: W.B. Saunders Co., 1295-1357, 1994.
Fathallah-Shaykh et al., "Mathematical modeling of noise and discovery of genetic expression classes in gliomas," *Oncogene*, 21:7164-7174, 2002.
Fleming et al., "Amplification and/or overexpression of platelet-derived growth factor receptors and epidermal growth factor receptor in human glial tumors," *Cancer Research*, 63:6613-6625, 2003.
Freige et al., "Gene Expression Profiling of Gliomas Strongly Predicts Survival," *Cancer Research, American Association for Cancer Research*, 64: 6503-6510, 2004.
Godard et al., "Classification of human astrocytic gliomas on the basis of gene expression: a correlated group of genes with angiogenic activity emerges as a strong predictor of subtypes," *Cancer Research*, 63;6613-6625, 2003.
Golub et al., "Molecular classification of cancer: class discovery and class prediction by gene expression monitoring," *Science*, 286:531-38, 1999.
Hermanson et al., "Association of loss of heterozygosity on chromosome 17p with high platelet-derived growth factor alpha receptor expression in human malignant gliomas," *Cancer Research*, 56:164-171, 1996.
Hermanson et al., "Platelet-derived growth factor and its receptors in human glioma tissue: expression of messenger RNA and protein suggests the presence of autocrine and paracrine loops," *Cancer Research*, 52:3213-3219, 1992.
Hill et al., "Molecular genetics of brain tumors," *Arch Neurol.*, 56:439-441, 1999.
James et al., "Chromosome 9 deletion mapping reveals interferon alpha and interferon beta-1 gene deletions in human glial tumors," *Cancer Research*, 51:1684-1688, 1991.
Kleihues et al., "The WHO classification of tumors of the nervous system," *J. Neuropathol. Exp. Neurol.*, 61:215-225, 2002.

(Continued)

*Primary Examiner* — Kenneth Horlick
(74) *Attorney, Agent, or Firm* — Fulbright & Jaworski LLP

(57) ABSTRACT

The present invention relates to novel primers for identification of astrocytoma, it's grades and glioblastoma prognosis. Further, disclosed is a method of diagnosing the presence of different grades of diffuse astrocytoma and glioblastoma, in a human subject, which involves detection of the expression levels of said genes in tumor tissue samples in comparison to normal brain. Also disclosed is a method of distinguishing between the two types of Glioblastoma—the progressive and de novo types. Also disclosed is a method of prognosis of glioblastoma based on the expression of the gene PBEF1, wherein the higher level of expression of the gene in the tumor sample, indicates poorer survival of the human subject. The disclosed compositions are useful, for example, in the diagnosis, prevention, treatment and/or prognosis of astrocytoma. The invention further provides kits for the detection and prognosis of the said diseases.

5 Claims, 18 Drawing Sheets

(56) References Cited

OTHER PUBLICATIONS

Kudoh et al., "Monitoring the expression profiles of doxorubicin-induced and doxorubicin-resistant cancer cells by cDNA microarray," *Cancer Research*, 60(15):4161-66, 2000.

Li et al., "PTEN, a putative protein tyrosine phosphatase gene mutated in human brain, breast, and prostate cancer," *Science*, 275:1943-1947, 1997.

Liang et al., "Gene expression profiling reveals molecularly and clinically distinct subtypes of glioblastoma multiforme," *Proc. Natl. Acad. Sci. U S A.*, 102:5814-5819, 2005.

Liau et al., "Identification of a human glioma-associated growth factor gene, granulin, using differential immuno-absorption," *Cancer Research*, 60:1353-1360, 2000.

Ljubimova et al., "Overexpression of alpha4 chain-containing laminins in human glial tumors identified by gene microarray analysis," *Cancer Research*, 61:5601-5610, 1995.

Louis et al., "A tiger behind many doors: multiple genetic pathways to malignant glioma," *Trends in Genetics*, 11:412-415, 1995.

Maher et al., "Malignant glioma: genetics and biology of a grave matter," Genes Dev., 15:1311-1333, 2001.

Maxwell et al., "Coexpression of platelet-derived growth factor (PDGF) and PDGF-receptor genes by primary human astrocytomas may contribute to their development and maintenance," *J. Clin. Investigation*, 86:131-140, 1990.

Nagane et al., "Advances in the molecular genetics of gliomas," *Curr. Opin. Oncol.*, 9:215-222, 1997.

Nutt et al., "Gene expression-based classification of malignant gliomas correlates better with survival than histological classification," *Cancer Research*, 63:1602-1607, 2003.

Olopade et al., "Molecular analysis of deletions of the short arm of chromosome 9 in human gliomas," *Cancer Research*, 52:2523-2529, 1992.

PCT International Preliminary Report on Patentability Chapter I issued in Application No. PCT/IN2009/000017, dated Jul. 22, 2010.

PCT International Preliminary Report on Patentability Chapter II issued in Application No. PCT/IN2009/000017, dated Jul. 23, 2010.

PCT Invitation to Pay Additional Fees and Partial International Search Report issued in Application No. PCT/IN2009/000017, dated May 14, 2009.

Phatak et al., "Alterations in tumour suppressor gene p53 in human gliomas from Indian patients," *J. Biosciences*, 27:673-686, 2002.

Rickman et al., "Distinctive molecular profiles of high-grade and low-grade gliomas based on oligonucleotide microarray analysis," *Cancer Research*, 61: 6885-6891, 2001.

Sallinen et al., "Identification of differentially expressed genes in human gliomas by DNA microarray and tissue chip techniques," *Cancer Research*, 60:6617-6622, 2000.

Somasundaram et al., "Upregulation of ASCL1 and inhibition of Notch signaling pathway characterize progressive astrocytoma," *Oncogene*, 24: 7073-7083, 2005.

Tanwar et al., "Gene expression microarray analysis reveals YKL-40 to be a potential serum marker for malignant character in human glioma," *Cancer Research*, 62:4364-4368, 2002.

Wang et al., "Insulin-like growth factor binding protein 2 enhances glioblastoma invasion by activating invasion-enhancing genes," *Cancer Research*, 63:4315-4321, 2003.

Watson et al., "Gene expression profiling with oligonucleotide microarrays distinguishes World Health Organization grade of oligodendrogliomas," *Cancer Research*, 61:1825-1829, 2001.

Westermark et al., "Platelet-derived growth factor in human glioma," *Glia*, 15:257-263, 1995.

Yamaguchi et al., "Differential expression of two fibroblast growth factor-receptor genes is associated with malignant progression in human astrocytomas," *Proc. Natl. Acad. Sci. U S A.*, 91:484-488, 1994.

Zhang et al., "PowerBLAST: a new network Blast application for interactive or automated sequence analysis and annotation," *Genome Research*, 7(6):649-56, 1997.

Zhou et al., "Modeling prognosis for patients with malignant astrocytic gliomas: quantifying the expression of multiple genetic markers and clinical variables," *Neuro-oncology*, 7:485-494, 2005.

* cited by examiner

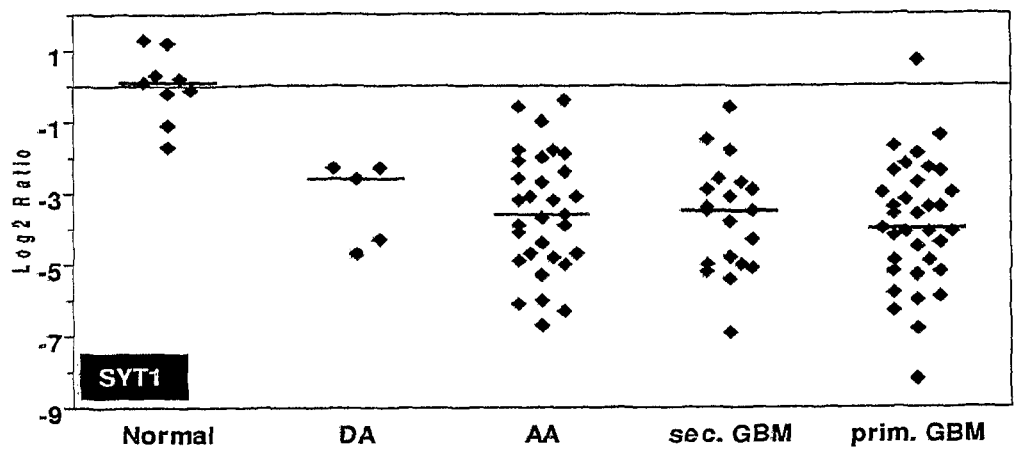
Figure 1.A
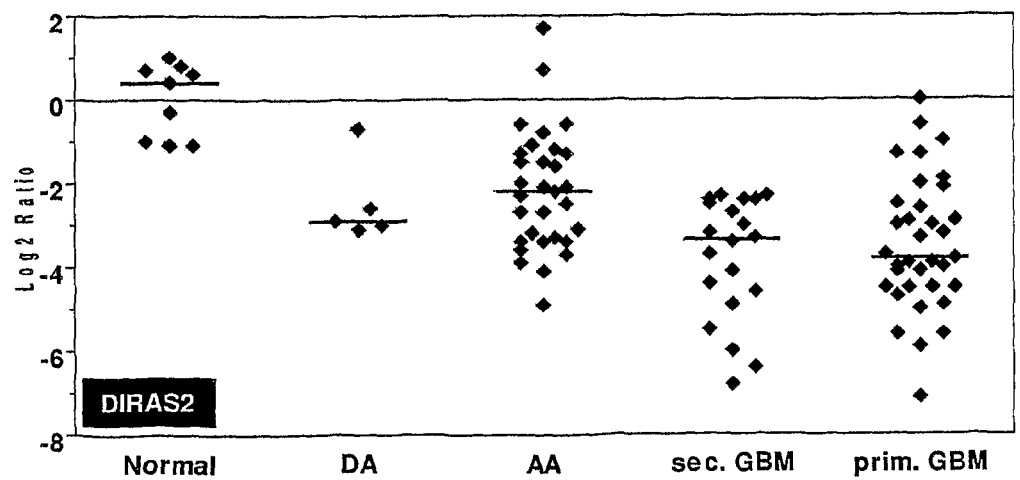
Figure 1.B

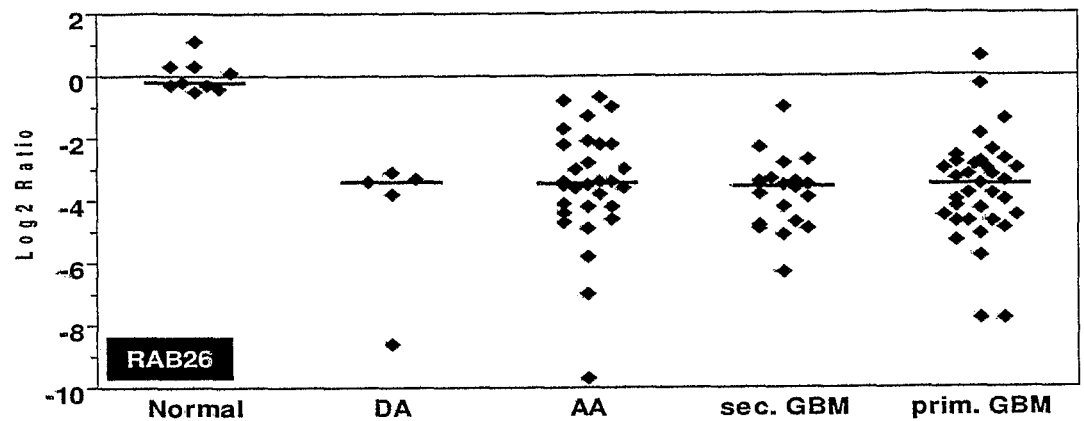
Figure. 1C
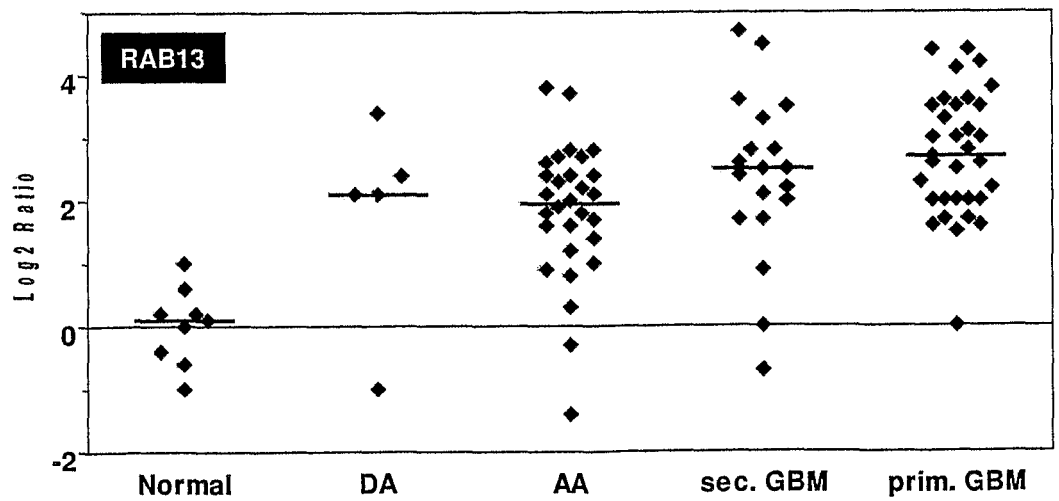
Figure 1.D

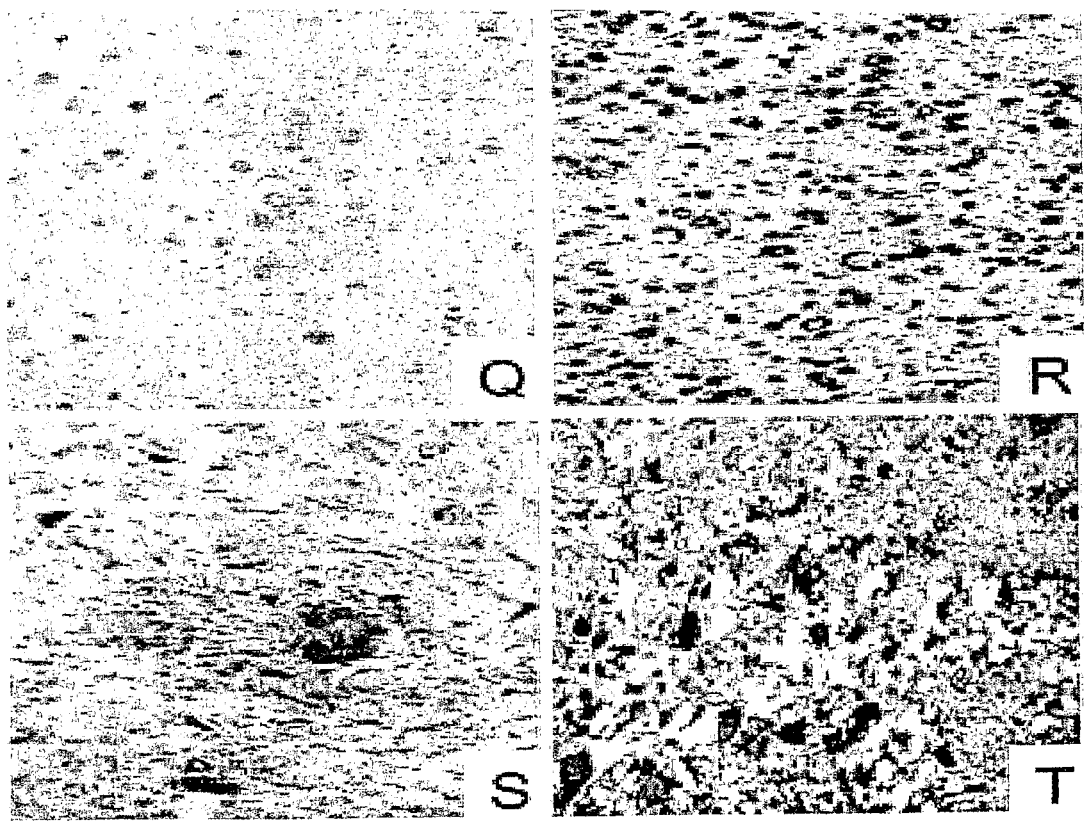
Figure 5 (Q-T)

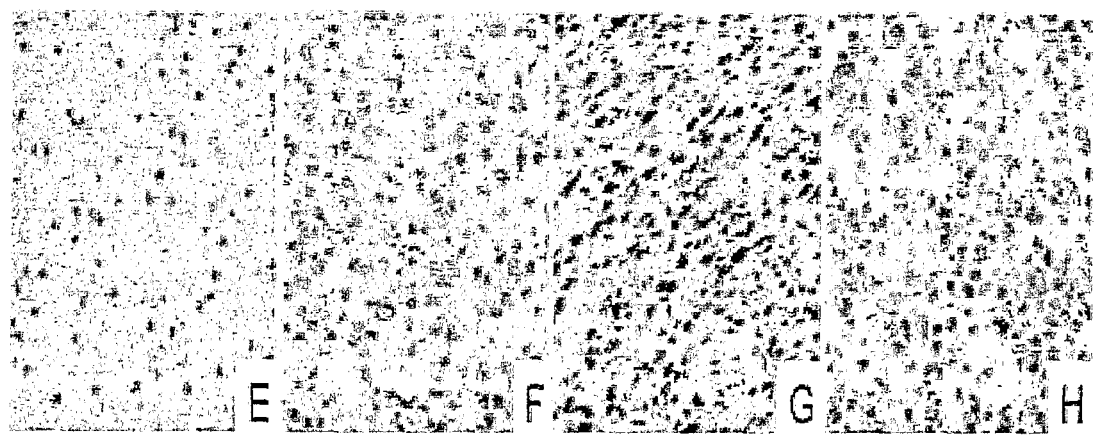
Figure 6(E-H).

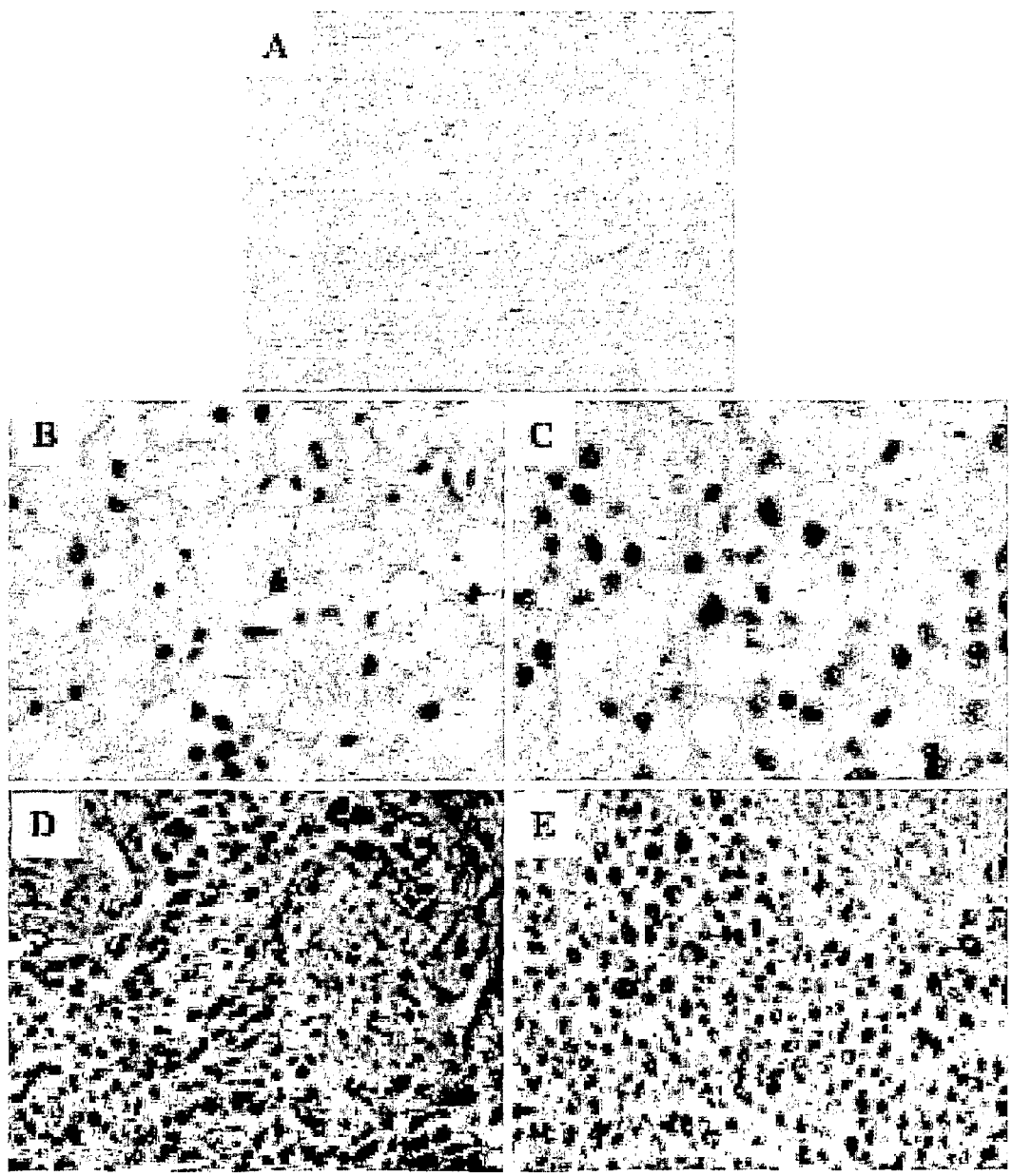
Figure 7 (A-E).

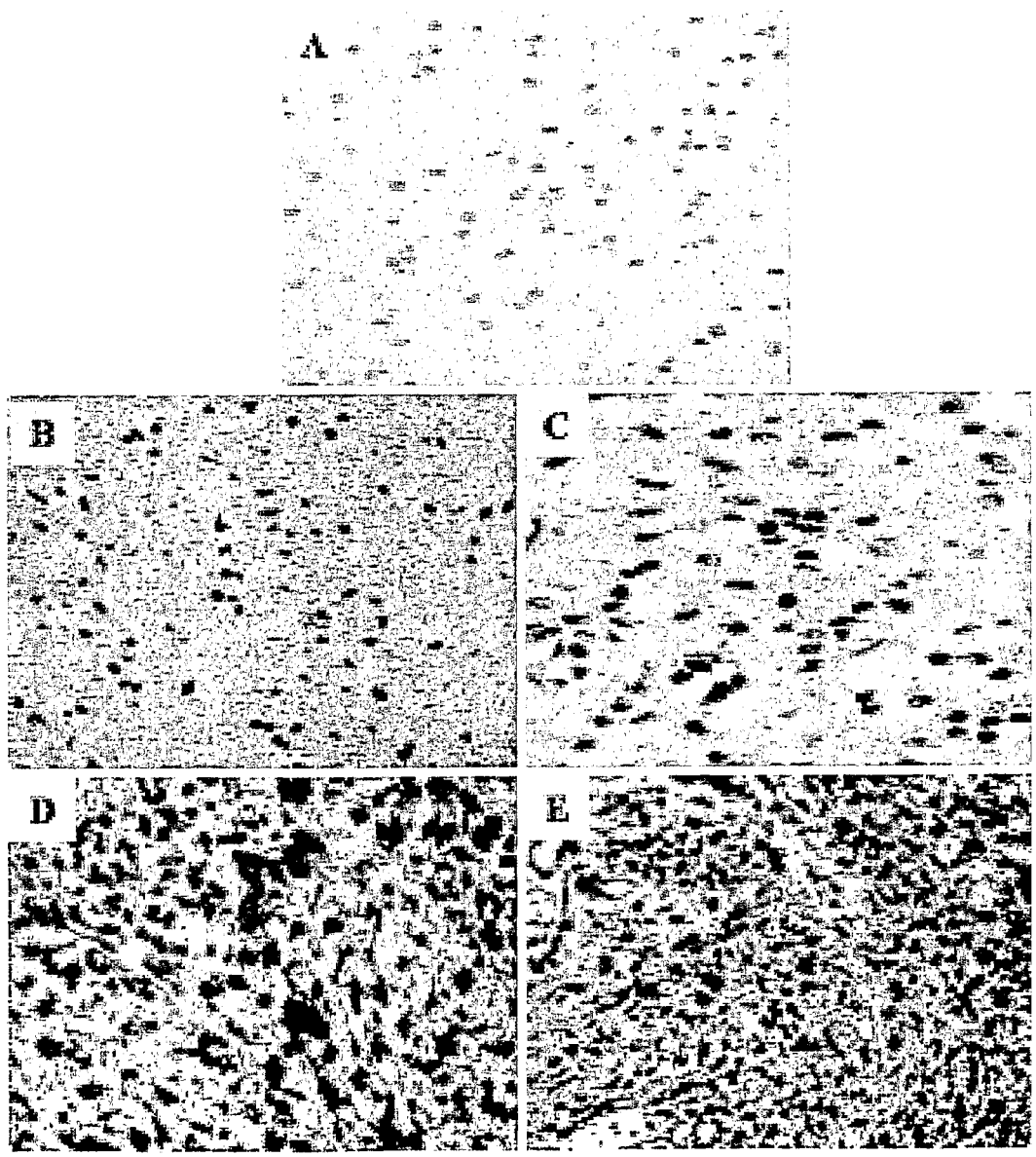
Figure 8 (A-E).

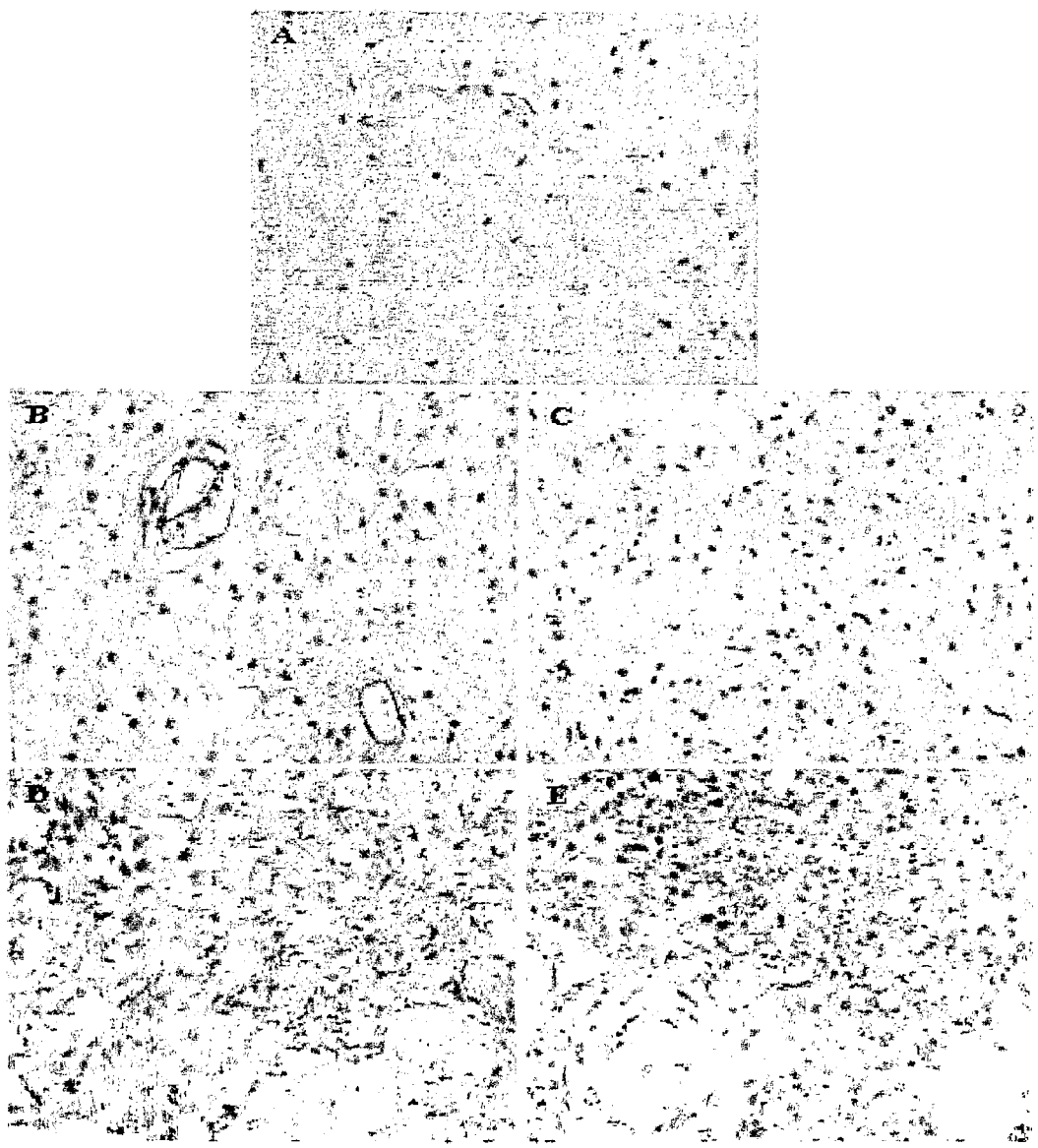
Figure. 9(A-E)

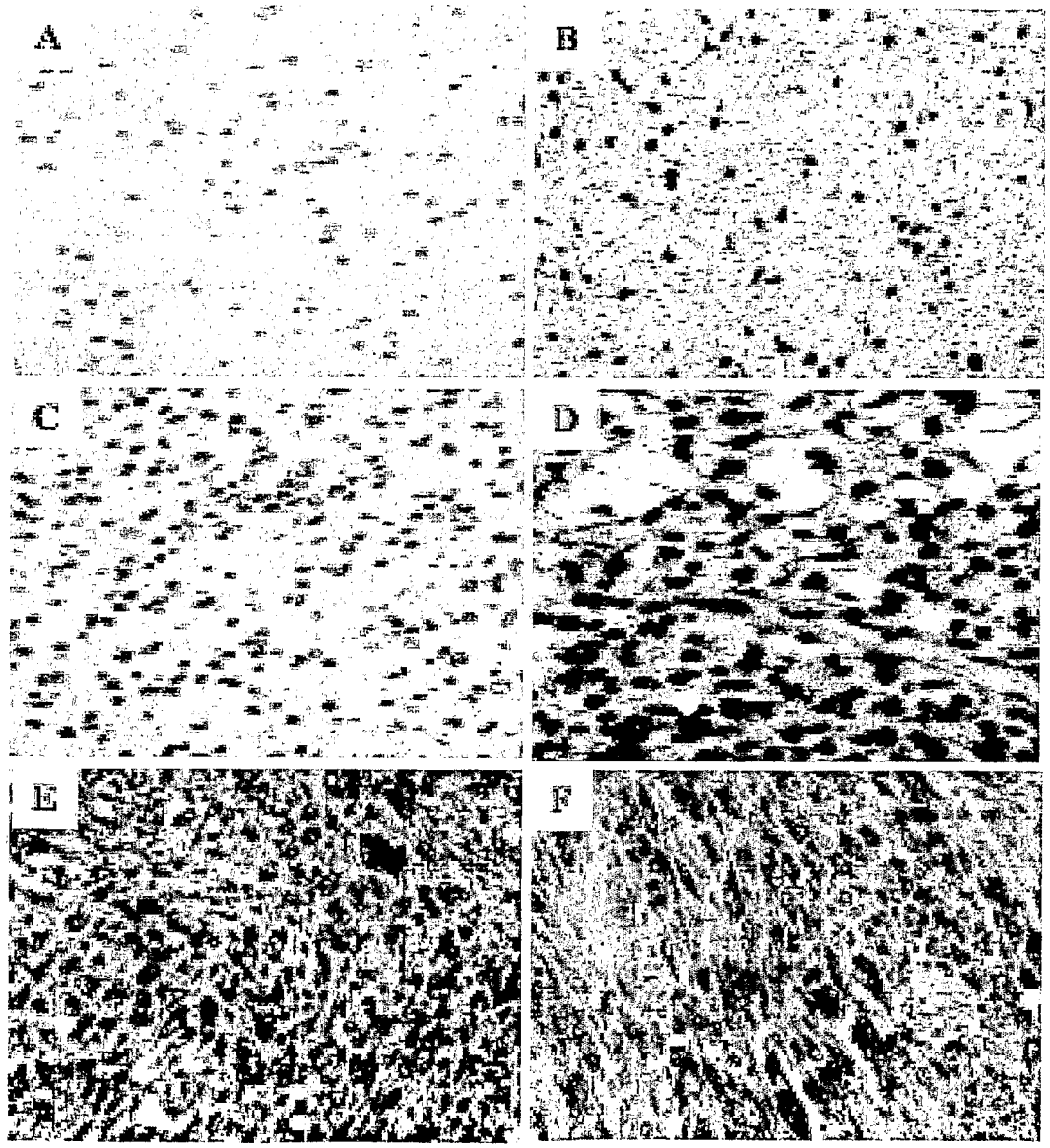
Figure 10 (A-F)

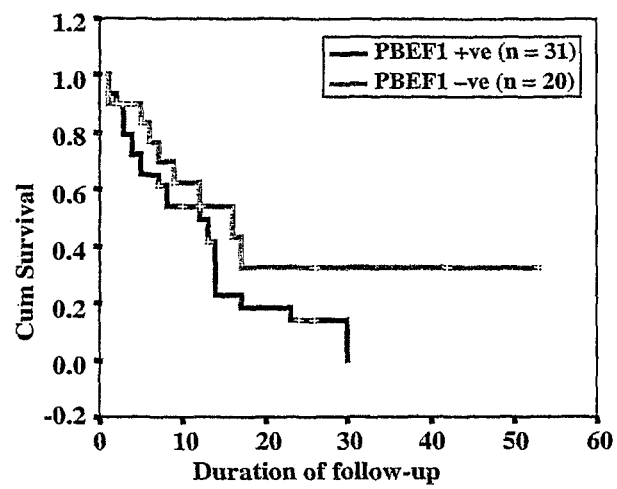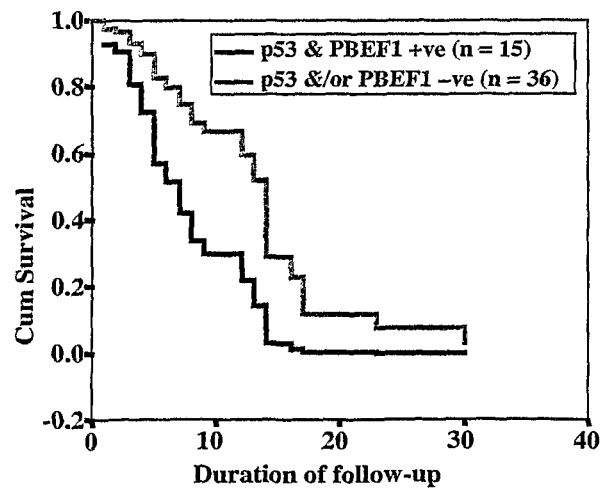
Figure. 11

METHODS AND KITS USEFUL FOR THE IDENTIFICATION OF ASTROCYTOMA, IT'S GRADES AND GLIOBLASTOMA PROGNOSIS

This application is a national phase application under 35 U.S.C. §371 of International Application No. PCT/IN2009/000017 filed 6 Jan. 2009, which claims priority to Indian Application No. 0054/DEL/2008 filed 7 Jan. 2008 and Indian Application No. 0055/DEL/2008 filed 7 Jan. 2008. The entire text of each of the above-referenced disclosures is specifically incorporated herein by reference without disclaimer.

FIELD OF THE INVENTION

The present invention relates to novel markers for identification of astrocytoma, it's grades and glioblastoma prognosis. The invention further provides novel markers and methods for diagnosing the presence of astrocytoma, it's grades and glioblastoma prognosis in a human subject and also provides a kit for characterization thereof. The present invention also relates to a method for diagnosing the presence of malignant astrocytoma followed by a kit for its characterization. The present invention further relates to a method for diagnosing glioblastoma in human subject and provides a kit for identifying the various types of glioblastoma followed by the characterization thereof in a human subject.

BACKGROUND AND PRIOR ART OF THE INVENTION

Gliomas are the most common primary brain tumors and occur at an incidence of almost 12 per 100,000 people (Landis et al., 1999). Diffuse astrocytoma may be classified (as per WHO classification) as low-grade diffuse (DA; Grade II), anaplastic (AA; Grade III) and glioblastoma (Grade IV; GBM), in the order of increasing malignancy (Mischel et al., 2001). Currently, these classifications are based on the observed histopathological characteristics of the tumor, which are sometimes subjective and inconsistent. GBM constitutes more than 80% of malignant gliomas (DeAngelis et al., 2001) and patients with GBM have a median survival of less than one year. Current treatments, including surgery, radiation therapy, and chemotherapy, unfortunately have not changed the natural history of these incurable neoplasms; and the prognosis of patients with GBMs has not improved significantly in the past 30 years (Davis et al., 1998). To find new diagnostic and therapeutic strategies, a better understanding of the biological pathway(s) leading to glial tumorigenesis is warranted.

Astrocytoma development is known to involve accumulation of a series of genetic alterations (Nagane et al., 1997) similar to other cancers. Identification of many of the genes involved in astrocytoma development, using standard molecular approaches, has helped to understand the process of astrocytoma genesis and progression (Louis and Gusella, 1995). Frequent amplification of epidermal growth factor receptor (EGFR) (Hill et al., 1999; Brock and Bower, 1997), platelet derived growth factor receptor (PDGFR) (Hermanson et al., 1992; Hermanson et al., 1996; Maxwell et al., 1990; Westermark et al., 1995; Fleming et al., 1992), amplification of chromosome 12q region, which carries the cdk4 gene (Nagane et al., 1997; Hill et al., 1999) and alterations in chromosomes 1p, 9p, 10, 17p, 19q, and 22q have frequently been found in these tumors. In addition, mutations in the tumor suppressor gene p53 were found to be associated with chromosome Yip alterations in low grade and progressive astrocytoma (Maher et al., 2001; Phatak et al., 2002). Inactivation of the cdk inhibitor p16 INK4a residing in chromosome 9p, is very common in sporadic astrocytoma, occurring in 50-70% of high-grade gliomas and 90% of GBM cell lines (James et al., 1991; Olopade et al., 1992). LOH in chromosome 10 is one of the most frequent alterations in GBM and is accompanied by the loss of PTEN/MMAC gene (Hill et al., 1999; Li et al., 1997).

GBMs are of two types: primary GBM (de novo type), which manifests in older patients (mean age: 55 yrs) as an aggressive, highly invasive tumor, usually without any evidence of prior clinical disease after a short clinical history of less than 3 months; secondary GBM (progressive type) is usually seen in younger patients (mean age: 40 yrs) and develops more slowly by malignant progression from diffuse (WHO grade II) or anaplastic astrocytoma (WHO grade III). Although some differences in the genetic lesions between these two GBMs have been identified, they are not sufficient enough to be used as differentiating markers considering the fact that the two types of GBMs have comparable clinical, genetic and biological characteristics (Kleihues et al., 2002). However, it is likely that these subtypes would respond differently to specific novel therapies as they are developed in the future (Kleihues and Ohgaki, 1999).

Despite all this information about astrocytoma, our understanding of astrocytoma development is not sufficient enough to improve prognosis for GBM patients. A more global, systematic understanding of expression patterns of various genes and their downstream gene products in astrocytoma will hopefully provide new diagnostic and therapeutic targets. Towards this, a number of studies have reported the gene expression profile of astrocytoma (Liau et al., 2000; Sallinen et al., 2000; Rickman et al., 2001; Ljubimova et al., 2001; Watson et al., 2001; Tanwar et al., 2002; Fathallah-Shaykh et al., 2002; Nutt et al., 2003; Wang et al., 2003; Godard et al., 2003).

It is also desirable to be able to target specific therapeutic modalities to pathogenetically distinct tumor types to maximize efficacy and minimize toxicity to the patient. (Golub et al., 1999; Kudoh et al., 2000). Previously, cancer classification has been based primarily on the morphological appearance of tumor cells. But this has serious limitations, because tumors with similar histopathgological appearance can follow significantly different clinical courses and show different responses to therapy. For example, based on histopathological appearance, astrocytoma grade IV cannot consistently be distinguished from astrocytoma grade III. Immunophenotyping for brain tumors has defined and refined diagnosis, e.g., distinguishing oligoastrocytoma from astrocytomas, and high-grade from low-grade astrocytomas. However, differential protein expression (GFAP, vimentin, synaptophysin, nestin) has not helped to improve therapeutic approaches. Prediction of transitions from low- to high-grade astrocytomas is difficult to make with currently available markers (De Girolami et al., 1994).

Tews and Nissen reported that immunohistochemical detection of various cancer-associated markers failed to reveal significant differential expression patterns among primary and secondary glioblastomas and precursor tumors; there was also no intra-individual constant expression pattern during glioma progression or correlation with malignancy. (Tews and Nissen, 1998-99). In contrast, class prediction for leukemia has been described based on monitoring gene expression profiles with DNA microarrays. (Golub et al., 1999).

But no class prediction capability, based on gene expression profiles, has been available heretofore for classifying high-grade gliomas to allow for optimizing treatment regimens. Zhang et al. (US Patent 20040053277) have identified a number of gene sets whose expression can accurately classify a glioma as glioblastoma (GBM), anaplastic astrocytoma (AA), anaplastic oligodendroglioma (AO) or oligodendroglioma (OL). However, these and other molecular markers currently in use are not capable of unambiguously identifying the subtypes of GBM. Mutations in p53 gene are reported to be associated with about 50% of grade WILL astrocytomas and secondary glioblastomas, but are seen only in 10-20% of primary glioblastoma (Campomenosi et al., 1996; Watanabe et al., 1997; Schmidt et al., 2002). Similarly, Epidermal growth factor receptor (EGFR), another marker routinely used in the classification of GBMs is found to be amplified in only 40% of all primary GBM cases and is rarely reported in secondary GBMs (Frederick et al., 2000). Microarray gene expression profiling of glioma allows simultaneous analysis of thousands of genes and is likely to identify molecular markers associated with tumor grade, progression and survival. Through cDNA microarray experiments, and subsequent validation with real-time quantitative PCR and/or immunohistochemistry, we have identified several distinct gene categories of transcripts over expressed in different set of astrocytoma. In addition, we have identified genes which characterize GBMs in general and primary GBMs in particular. Furthermore, we have also established the correlation between treatment response and the expression of the genes identified. Therefore, it is also a desideratum to be able to predict the presence of astrocytoma, type of glioblastoma and subtype of glioblastoma in the context of prognosis and, thus, to be able to administer appropriate treatment. These and other benefits are provided by the present invention.

OBJECTS OF THE INVENTION

The first object of the present invention is to provide a method for diagnosing the presence of astrocytoma in a human subject.

Another object of the present invention is to provide a kit for characterizing astrocytoma in a human subject.

Another object of the present invention is to provide a method for characterizing malignant astrocytoma (AA, GBM) in a human subject.

Another object of the present invention is to provide a kit for characterizing malignant astrocytoma (AA, GBM) in a human subject.

Another object of the present invention is to diagnose the presence of glioblastoma in human subject.

Another object of the present invention is to provide a kit for characterizing glioblastoma (GBM) in a human subject.

Still another object of the present invention is to provide a method for identifying the type of glioblastoma in human subject.

Another object of the present invention is to provide a kit for distinguishing primary and secondary glioblastoma in a human subject.

Another object of the present invention relates to a method for the prognosis of glioblastoma in human subjects.

Further, another object of the present invention relates to a kit for the prognosis of glioblastoma in human subjects.

SUMMARY OF THE INVENTION

The present invention relates to a method of diagnosing astrocytoma from a normal sample in a human subject based on the expression level of a single gene in a test sample of brain tissue cells obtained from the said human subject and in a control sample of known normal brain tissue cells wherein higher or lower level of expression of the mentioned genes in the test sample as compared to the normal sample in the said human subject indicates astrocytoma. It also relates to a kit to identify astrocytoma in a human subject.

The present invention relates to a method of diagnosing malignant astrocytoma (AA, GBM) in a human subject based on the expression level of a single gene in a test sample of brain tissue cells obtained from the said human subject and in a control sample of known normal brain tissue cells wherein higher level of expression of the gene in the test sample as compared to the normal sample, indicates malignant astrocytoma in the human subject from which the test sample has been obtained. It also relates to a kit to distinguish malignant astrocytoma from the benign astrocytoma in a human subject.

The present invention relates to a method of diagnosing glioblastoma from low-grade astrocytoma in a human subject based on the expression level of a single gene in a test sample of brain tissue cells obtained from the said human subject and in a control sample of known normal brain tissue cells wherein higher level of expression of the gene in the test sample as compared to the normal sample, indicates glioblastoma (GBM) in the human subject from which the test sample has been obtained. It also relates to a kit to distinguish glioblastoma from low-grade astrocytoma in a human subject.

The present invention relates to a method of distinguishing primary glioblastoma from secondary glioblastoma in a human subject based on the expression level of a single gene, in a test sample of brain tissue cells obtained from the said human subject and in a control sample of known normal brain tissue cells wherein higher level of expression of the above mentioned genes in the test sample as compared to the normal sample, indicates primary glioblastoma in the human subject from which the test sample has been obtained. It also relates to a kit to distinguish primary and secondary glioblastoma in a human subject.

Further, another object of the present invention also relates to a method for the prognosis of glioblastoma in human subjects. The present invention relates to a method of prognostication of the survival of human subject with glioblastoma based on the expression of the gene PBEF1 in a test sample of brain tissue cells obtained from the said human subject and in a control sample of known normal brain tissue cells wherein higher level of expression of the gene in the test sample as compared to the normal sample, indicates poorer survival of the human subject from which the test sample has been obtained. It also relates to a kit to distinguish a human subject with glioblastoma of poorer survival from that of better survival.

DETAILED DESCRIPTION OF THE INVENTION

The present invention relates to a method of diagnosing the presence of a astrocytoma, malignant astrocytoma, glioblastoma and to identify the type of glioblastoma in a human subject. Diffuse infiltrating astrocytomas include the following entities: 1. Diffuse astrocytoma (DA; WHO Gr. II), 2. Anaplastic astrocytoma (AA; WHO Gr. III) and 3. Glioblastoma (GBM; WHO Gr. IV). AA and GBM constitute malignant astrocytomas and are the most common intrinsic CNS neoplasms. The development of GBM has been described to occur through at least two genetic pathways resulting in the formation of primary and secondary GBMs. Primary GBM represents the most frequently presenting variant occurring de novo without an evidence of a less malignant precursor. Patients under this category are commonly of older age and have a high rate of epidermal growth factor receptor (EGFR) gene amplification, p16 INK4A deletion, mutations in PTEN gene and MDM2 amplification. In contrast, secondary GBM occurs after a preceding diagnosis of lower grade astrocytomas. Mutations in p53 gene, RB alterations and PDGFR amplification and over-expression are thought to be more common in the development of secondary GBM. In spite of these genetic differences, it remains uncertain whether these subtypes differ significantly with respect to prognosis.

The inventive method involves collecting or otherwise obtaining a sample of a bodily substance derived from the human subject, which sample contains human nucleic acid or protein originating from the subject, and quantitatively or semi-quantitatively determining therein the level of expression of single or combination of genes selected from the groups comprising of:

1. SYT1, RAB26, DIRAS2 and RAB13. A characteristic expression pattern of the said genes is diagnostic for the presence of astrocytoma.
2. IGFBP7. A characteristic expression pattern of the said gene is diagnostic for the malignant astrocytoma (AA, GBM).
3. COL6A1, DCN, PLAT, LGALS3, FABP7, LOX, LAMB1, IGFBP3, GADD45A, FSTL1, RHOC, B2M and PBEF1. A characteristic expression pattern of the said genes is diagnostic for the presence of glioblastoma.
4. AEBP1 and SOD2. A characteristic expression pattern of the said genes is diagnostic for the type of glioblastoma.
5. PBEF1. A characteristic expression of said gene to determine the prognosis of glioblastoma This includes detection by means of measuring of proteins or specific nucleic acids, such as RNA or cDNA.

The sequences used in the present invention are provided here as under. However, they are not arranged according to the SEQ ID but according to the genes to which they correspond [the sequences arranged as per the SEQ ID as well as the key to the Sequences are provided in the later pages in the patentIn 3.5 format].

1. Synaptotagmin I (SYT1)
Accession number: NM_001135806
Sequence:

ACCACCAAGAATAAAATAGTTGTTTGTCCCCTACAGTAGAACAAGTTT

GCCCATTCATCCTTGTGATAGATATGCATGCAAAACCAAATGAAATC

AAATCCCCACAGATGGCTCGTAAGTCAAAAACACTGTTTAATTCTTTC

ACTGCATCCCTTTGGGAAGCCTGGCCCTTGAAAAACAGAATAATTCTG

AAAGAAAGAAAACAAAGAAAAACATACTCCAGAATTCCTAATAGAACA

CTTCACCTGAACCTAAAATGGTGAGCGAGAGTCACCATGAGGCCCTGG

CAGCCCCGCCTGTCACCACTGTCGCGACTGTTCTGCCAAGCAACGCCA

CAGAGCCAGCCAGTCCTGGAGAAGGAAAGGAAGATGCATTTTCTAAGC

TGAAGGAGAAGTTTATGAATGAGTTGCATAAAATTCCATTGCCACCGT

GGGCCTTAATTGCAATAGCCATAGTCGCAGTCCTTTTAGTCCTGACCT

GCTGCTTTTGTATCTGTAAGAAATGTTTGTTCAAAAAGAAAACAAGA

AGAAGGGAAAGGAAAAAGGAGGGAAGAATGCCATTAACATGAAAGATG

TAAAAGACTTAGGGAAGACGATGAAAGATCAGGCCCTCAAGGATGATG

ATGCTGAAACTGGATTGACAGATGGAGAAGAAAAAGAAGAACCCAAAG

AAGAGGAGAAACTGGGAAAACTTCAGTATTCACTGGATTATGATTTCC

AAAATAACCAGCTGCTGGTAGGGATCATTCAGGCTGCCGAACTGCCCG

CCTTGGACATGGGGGGCACATCTGATCCTTACGTGAAAGTGTTTCTGC

TACCTGATAAGAAGAAGAAATTTGAGACAAAAGTCCACCGAAAAACCC

TTAATCCTGTCTTCAATGAGCAATTTACTTTCAAGGTACCATACTCGG

AATTGGGTGGCAAAACCCTAGTGATGGCTGTATATGATTTTGATCGTT

TCTCTAAGCATGACATCATT

GGAGAATTTAAAGTCCCTATGAACACAGTGGATTTTGGCCATGTAACT

GAGGAATGGCGTGACCTGCAAAGTGCTGAGAAGGAAGAGCAAGAGAAA

TTGGGTGATATCTGCTTCTCCCTTCGCTACGTACCTACTGCTGGTAAG

CTGACTGTTGTCATTCTGGAGGCAAAGAACCTGAAGAAGATGGATGTG

GGTGGCTTATCCGATCCTTATGTGAAGATTCATCTGATGCAGAATGGT

AAGAGGCTGAAGAAGAAAAAGACAACAATTAAAAAGAACACACTTAAC

CCCTACTACAATGAGTCATTCAGCTTTGAAGTACCTTTTGAACAAATC

CAGAAAGTGCAGGTGGTGGTAACTGTTTTGGACTATGACAAGATTGGC

AAGAACGATGCCATCGGCAAAGTCTTTGTGGGCTACAACAGCACCGGC

GCGGAGCTGCGACACTGGTCAGACATGCTGGCCAACCCCAGGCGACCT

ATTGCCCAGTGGCACACCCTGCAGGTAGAGGAGGAAGTTGATGCCATG

CTGGCCGTCAAGAAGTAAAGGAAAGAAGAAGCCTTTCTGCATTTGCCC

ATATAGTGCTCTTTAGCCAGTATCTGTAAATACCTCAGTAATATGGGT

CCTTTCATTTTTCCAGCCATGCATTCCTAACACAATTCAGTGGTACTT

GGAATCCTGTTTTAATTTGCACAAATTTAAATGTAGAGAGCCCCTAAG

TCCTTCATCATACCACTGCCCTCCAAATCTACTCTTCTTTTAAGCAAT

ATGATGTGTAGATAGAGCATGAATGAAATTATTTATTGTATCACACTG

TTGTATATACCAGTATGCTAAAGATTTATTTCTAGTTTGTGTATTTGT

ATGTTGTAAGCGTTTCCTAATCTGTGTATATCTAGATGTTTTTAATAA

GATGTTCTATTTTAAACTATGTAAATTGACTGAGATATAGGAGAGCTG

ATAATATATTATACGGTAAATATAGTATCGTCTGCATTCCAGCAAAAA

TATCAACTCGTAAGGCACTAGTACAGTTAAACTGACATCTTAAAGGAC

AACTTAAACCTGAGCTTTCTATTGAATCATTTGAGTACCAAGATAAAC

TTACACCACATACTTGGTGGGTGAATCCAATTTTGTAGAATTCCTACA

CAGGCAAAATAGCATGATCTGAGCAGCAGCATCCAGGCTGACCTCAAG

GAAGCATAGCCACAAAACAGAATAGCACCTGTCTGTACATATTTACAA

AGCTAAAATAATGGCTTCACTCTTATATTTGAGGAAGCAACTGAACAG

GAGTCAATGATTTCATATTACTGCATATAGAATAACAACAAGGTGTTC

CGTGTGTGTGTGTGTGTGTGTGTGTGTGTGTGTGCACATTTGTTTG

GGGATGGGGAGAAGAAGCTAAGGGGAGAAGTCAACATTTATGAAATA

TTGCCTGACTATTTAAAAAGAAAAAAGTAGCTCTCCATTATCACCTTT

ATACAAAATGTACATCCTGTGAATTCTGTTCCAGATTTCACACCTACA

ATAATTCCAAAAGGTTTGCACATTAGAGTTTGTAACAAAATATTTTAT

TATATAAAACCAGGTTAGAAGGAATGCAGGATATTTTTAACACAACAA

TCTGTGCTTATTACACAAAATTACTTTGTGGTAAACAGACAGTATTGT

AATCCCATCAAAAGATGAAAGAAAACAAAAACAAAAACCAACAACAA

-continued
TTAGCCATAGTTCTGAATGCACTTCAATTAAGCCAAAACAGACAGCTA
GTGATCTTTTTATATGCTCTTTTTACTTAAGTTTTAATTTGTCCTTTA
AAAAAAGGTGAAACAAACCAAGAACAAGTTCTAGAAAACTGAAGCAAC
CTCTTATGTATACTAGATGCTTGATTTAGGAGGAGTTTTTAAACGTTT
TCAATGTTATTATGTAGTAAATGACACTATTATGAAGCTACTAGTCAT
TCCATAAGAGTCTTAAAGGACTGCTCTGTGTAACACTGTGACTGCCGT
GTGTGCTTAGACCCGTAGTTTCCTCAGTGGATAGCACTCAATTTATTC
CGTAGTGATATTGTAACAATACTGCCATTCCCTTCTACTGCACTGCCC
AAGGTGTGTGTAGCACAAACAGTTCTCATTACAAAGGACCAATTCAGA
ACTGAAAAGCTATGCATAGGACAAGGAAGATACATAGAATGGGGTGGA
ACACAGCATTTTGTCAAGCACTGTGCAATATTCCATATTTTTCCCCAC
TATGGTAGACAACCATTTCGTGGAAGGGCAGCCTATTATCCCACACTG
CATCTAGCCTTTTGTCCCATTCACTTCTGTGATCCATTTTAATTTCCA
GGCCACAAGACAGTAGTGATGCTCTGAAATGAAAGTTTGTCTTCACAA
ATATCAAAACAAAATGGAGGAAAACTAAGCATTGGCCTCATGTTCAGT
CTTCAGGATATCACACCACGTCTTTTCAAAAACTAAAGAGAATTCAAA
AAGGGCTGATGGTAGGCTTTGAACATGGGGTTGGCTGTTTCCCAGTAA
AACTGGAATTCCTGTCGTTACTGTTTCCTTATCAAAGAAGGGGCAAGC
TCTTTTGCCTTTTAGGCCAGACATAGCAAACGCTTTATAATTGGCATA
GACATAAAGGATAAAAGGAAAATAACCGTCTGCCGATGGTCCGTACTT
CTTAAAAAACATAGGTAATAGAAAATATACACAAGTCAGAATGTGAAA
TTAAATAATGGTTTGAACAGAAAATTCAAACAAGACTCTTTCCAATTT
AAAGGGCCAAACCCTACCAAAGAGAGGGAGTTGACTGGCTTTTAAAAA
GTATTTAAATACCACAAATGACATTTAATTTCACTGTATTCAGCTTTA
AGTTGTTCACAATGAAACCACACTTTCAAACAAGCAGGTTCAAGCTGC
TGAATAGACATTATTTCTTGCATTAAAATACCACTAATGCATTCTCTT
GCAACACTGCCAGACATGGGATTGTCACCATAGAATTAGTTGGTACTA
TGCCATCTTTCACTCTTTCACAAGTCAGTGATGGAACCTGCTTTATGA
CCAAGATTCATCCTCAAATAAGCCACATGTACCCTTCTGACAAAGCTG
TGTAAAGTATTAGAATCTGATGCTCTAGAAAGATCCTAGTTGCCTTTG
TGTATATTTACTGCCTGCTTGAGTGTTTCTATGTGTGGGTTTTCCCTG
TATCTTGTAGAAATGTTGGGGTGTTTCCTCTGCCATATGGCTCGTGG
CCTGCGAGCCAACTATTTCAGCTGTATTTTACCTTCATTTTTGATGAG
GTGATTTAAATTTTGTTTCACTTTGTGTAGTGAATTCCACAGTAGTTT
TCTGATTGTTGTTAAAAATGACTTAACATATTACACAGATATTCAATA
AAAATGTTTTATTTCCTGTTGAAAAAAAAAAAAAAAA Primers used:

Forward primer sequence:
        GGTTGGCTGTTTCCCAGTAAAAC

Reverse primer sequence:
        TTTTAAGAAGTACGGACCATCGG

Amplicon length: 171
Amplicon sequence:

GGTTGGCTGTTTCCCAGTAAAACTGGAATTCCTGTCGTTACTGTTTCC
TTATCAAAGAAGGGGCAAGCTCTTTTGCCTTTTAGGCCAGACATAGCA
AACGCTTTATAATTGGCATAGACATAAAGGATAAAAGGAAAATAACCG
TCTGCCGATGGTCCGTACTTCTTAAAA

2. RAB26, Member RAS Oncogene Family (RAB26)
Accession number: NM_014353.
Sequence:

GCCGCCGCCGCCGCCGCCGCCGCCGCCGCCAGGGGAAGGGTTCGG
GTCCGGGTCGGCTCGGCGGGCGCGGGGTGCGGGACGGCCCAGGGCAC
GGCGGCTGCAGCGGGAGCACACTGAGCGCCCGCCCGCCATGTCCAGGA
AGAAGACCCCCAAGAGCAAAGGGGCCAGCACCCCGCTGCCTCCACGC
TGCCCACCGCCAACGGGCCCGACCGGCGCGCTCCGGGACTGCGCTTT
CCGGCCCCGACGCGCCGCCCAACGGGCCCTTGCAGCCCGGCCGGCCCT
CGCTTGGCGGCGGTGTCGACTTCTACGACGTCGCCTTCAAGGTCATGC
TGGTGGGGACTCGGGTGTGGGAAGACCTGTCTGCTGGTGCGATTCA
AGGATGGTGCTTTCCTGGCGGGGACCTTCATCTCCACCGTAGGCATTG
ACTTCCGGAACAAAGTTCTGGACGTGGATGGTGTGAAGGTGAAGCTGC
AGATGTGGGACACAGCTGGTCAGGAGCGGTTCCGdAGTGTTACCCATG
CCTACTACCGGGATGCTCATGCTCTGCTGCTGCTCTACGATGTCACCA
ACAAGGCCTCCTTTGACAACATCCAGGCCTGGCTGACCGAGATCCACG
AGTACGCCCAGCACGACGTGGCGCTCATGCTGCTGGGGAACAAGGTGG
ACTCTGCCCATGAGCGTGTGGTGAAGAGGGAGGACGGGGAGAAGCTGG
CCAAGGAGTATGGACTGCCCTTCATGGAGACCAGCGCCAAGACGGGCC
TCAACGTGGACTTGGCCTTCACAGCCATAGCAAAGGAGTTGAAGCAGC
GCTCCATGAAGGCTCCCAGCGAGCCGCGCTTCCGGCTGCATGATTACG
TTAAGAGGGAGGGTCGAGGGGCCTCCTGCTGCCGCCCTTGAACCTGGC
TGAGCTCAGTCCTCTGGAGGAAGCCGCCCAGTCCCTAGAAGGCTGGAC
AGAGGGTCTCCAGGCCCTTCTGACTTTGTTGCCCAGTGGCCAACGCCC
GAGTGTCTGTTTTCAGGAGCCCCAGGTCAAGCCTTGTCCCTTCCTCCT
CCCAGCAACAGTCCCAACAAGCAGGCTTCTGAGAGCCCGTGGCCGCAC
ACTGGCCGCCACGGAAAAGCAGTCTTCTGCACGGGACGGGGAGCGGCA
AGTGGACAGACTTTGCCACGGTGCTCTGCTGCCCCCTCCTGGGCACGT
CCAGGTGAGGGAGGGCTGGGGCTGGCACCACGCACAGTGCCTAACCCT
AGAAAAGCCATGTCTTCAGCCGCACATGCTCAGGCAGCTAAGGGAGGA
CGCCTGCCCACGCCTGGGACAGAAGGCTTCACTGCTAATCACATCGTG
CATCTGTGTGTCCTGGGAGCTGCCTGCTCCCGGCCCACCCTCTAGGAG
GCTCTGGCTCAAACAGCAATAGGGTCTTCCTCACTGACCTTGGAGGAT
GCCTGTGGCCTTGTGATAAAATGTGGGAAATCACAGAAAACACCAGAA
ACAACAACTGCCAGCCCGGCCTGGCCACAGGTGAGGTCTGTGATTTCC

-continued

GAGCACGCTCCACCTTGCACTCAACTTGGCCTTTTGATTGCACAAGCC

TTTGTTTTCAGTCCTAGTGAATAAAGTTGTGTTTTCTGGAAAAAAAAA

AAAAAAAAA

Primers used:

Forward primer sequence:
GTCTGCTGGTGCGATTCAAG

Reverse primer sequence:
GCATGGGTAACACTGCGGA

Amplicon length: 163
Amplicon sequence:

GTCTGCTGGTGCGATTCAAGGATGGTGCTTTCCTGGCGGGGACCTTCA

TCTCCACCGTAGGCATTGACTTCCGGAACAAAGTTCTGGACGTGGATG

GTGTGAAGGTGAAGCTGCAGATGTGGGACACAGCTGGTCAGGAGCGGT

TCCGCAGTGTTACCCATGC

3. DIRAS Family, GTP-Binding RAS-Like 2(DIRAS2)
Accession number: NM_017594
Sequence

ACACACCCTGCGCTGCCCTGTCCTGCGCGAGTGGAGCTCTGAAGAAGC

TCTGAGCGGAGTTGTGTTCTTCCCCAGGTGCGTCCTGGCTGAGAGTTG

GAGCTCTCCAGCAACATGCCTGAGCAGAGTAACGATTACCGGGTGGCC

GTGTTTGGGGCTGGCGGTGTTGGCAAGAGCTCCCTGGTGTTGAGGTTT

GTGAAAGGCACATTCCGGGAGAGCTACATCCCGACGGTGGAAGACACC

TACCGGCAAGTGATCAGCTGTGACAAGAGCATATGCACATTGCAGATC

ACCGACACGACGGGGAGCCACCAGTTCCCGGCCATGCAGCGGCTGTCC

ATCTCCAAAGGGCACGCCTTCATCCTGGTGTACTCCATTACCAGCCGA

CAGTCCTTGGAGGAGCTCAAGCCCATCTACGAACAAATCTGCGAGATC

AAAGGGGACGTGGAGAGCATCCCCATCATGCTGGTGGGGAACAAGTGT

GATGAGAGCCCCAGCCGCGAGGTGCAGAGCAGCGAGGCGGAGGCCTTG

GCCCGCACATGGAAGTGTGCCTTCATGGAGACCTCAGCCAAGCTCAAC

CATAACGTGAAGGAGCTTTTCCAGGAGCTGCTCAACCTGGAGAAGCGC

AGGACCGTGAGTCTCCAGATCGACGGGAAAAAGAGCAAGCAGCAGAAA

AGGAAAGAGAAGCTCAAAGGCAAGTGCGTGATCATGTGAAGGCCCTTC

CTGCGGGAGGAGCAGCTGTGTGTCCCCGGCACCTCACTCCCCCAAAAT

GACACCCACCGTCGTCAGGGTAGCATGTATAATGCCCACGTGTTAAAC

ATTGCATTTAATCGAGATGCGTCCTATTGTCCTTAAGAGGGCGTTTCA

CACCACCAACAGTAAGCCACCCACTCTGGAGTCACAGAATCTGCCAGG

CGGTTCAAGTGAAAACCAACACACTCAGCATCCCTGGGAACTGAGAGG

TGCCAGCAATTGCTGAAGGTGGCGATGAACACCCGAAGGTGGGAGGGA

GGACTGGTACCCACAAAGCAACATGTACCGAGAGGACTAAATGTCATC

TACGTGCATGTGAGAGCGTGTTAACCTAGAGTTACCTGCACCAACCCC

AGACAGAAGCCAATCACATCTTTGGGGGAGGGGAGGGGCAGGAAGAGG

TGAGAAGATCAGATGGTCCAAAGTGGACCACACTTGGTCCATTTTACA

CTTTTTTAAAGGGGATTAAAAAACACAGCCTCTCCCCCAAAGGGTGTC

CGTTCTTAATTCCCACCTGGCCTGTTAGGAGCCTTGCTACCCTGAGGG

GATGTGTTCACCTTACCTAGACCTAGTTAGGAAGTATCATTTTAAGCT

ATTAGAGTATTTATCTTCATGTGCAGGGATAAGTGCACTAACAGTGTG

CTGCTCTGTCGGAAGTTCTTCAGTTTTTAAGTGAGGATATCGTGACAG

TATTAAAACATCGCAATAATGTTCCTGTGTGTTATACATCGAGGGTTT

TAGAAATGTGATTTTCTTCTTTTGACCTGTGAGGAGTATAACTTCTTT

CAGCCCTCAGATTTTAAATACAAGCAAATAAACTCACTATTTTTAGAC

GTTTTTTTCCTCCAAGGTGGTTTTCTTCTCTTAAATAACTCGATCTGT

ACCCAGCTGGGTAGCAGCCAGCAAAGGCCATCAGACAACCAGAAGCAC

ATCCATTTTTGTAGTGTCACAAACATGTATATGCCACACTTTGCACCT

TAATGAAATACTTTGAAACAGAAGTTATTCACTGTGTTTTTGATGATC

TATCTGTATTGGAAATATGTTCCTGGAAATGCATTTAAATAATAGTA

AATTCTCTTGCATGTTCCATTATACGTGTCTTCTAAGAGCTGTTCAAT

ACAGTATTCACTCTAGAAACAATTATCTTTTTCTCTTAATGATTTTGT

GTGCATCTTTAATCTTTCAAGCCAAATTACAGCTATTTCAGGTTTCCT

GTGTTAGCTTGGGGATAGGATGGTGGCTGGAGACAGGCAGGCTTCTCT

GCCCTGGGAAGAGCCCACTCAGCTTAATTGCTCTGCCATCGTAGAGCC

TGGTTGGACTTGGCTTCCTGAAAACTCCCACTGATAGTGCCTGTTAGA

TCTCCTGTTTGTTTCAGTTGGCAGAACATTTACTGGCCCCAACTGTGG

CATCATCCTCTCAGCAGTCTTCCTGTCACCCGCCTGGCAGGCAGAAGG

AGCTGCAGTCCTACGTGGGCCTGCCTGGGGGGTGGGGCTGCATGGC

TGTTGGGTGGCAGTGTCAGCACAGGGAGGGCTTAAGTTGGGGATGTTT

GACCAGGCCACCTCCTGCAACTGCTGTTTCTCCTGTCCCTCCTATGCA

GGGCTTGCAGCAGCAGCAGTGTGGCCATCTCCATCCCCCAAAGCACAC

TTGCTCTCTCAATATGTCCTAGTTTTCTTCAGCCTTTTCTGGTTCAGT

TCCCTTGTCCTGATCTCATCCTCTCTGGTCTCCCAATAACTCACCCTT

GGGATGTGTTTAGAGCGTGGGAGGTGCCTTTGAGAACTGCTTGACTCC

ATGATCTCCTAGAACAAAACCGCCCTGACTTTACAGGGGGAACACTCA

TGCTGAGCTGAGAAAGCAGAGAAGTGGCGTGGGAGCCAGCTGGGGGTG

AAGAGCATTTGGGCCAGTCCCGTGGCCCCCTTCAGATTCCTCAAGCAG

GATTGTTCTGTTCTAAAAAGCTGTTGCACAGCATTCGCAATGAGATCT

TTAGTTGGCGGATTTTCTGGAACATTTGTTTTTCAACTTGTCCCGACA

TTTTTTTTCTGTTTCTATTCTGAGAGAGAGATGATCAAGTTTTAATTT

GGGTATAGGTTAAATGGAAGAAGAAACAGAACTTCATGGCCAAAGTAG

ACCTATAGATTTTGATTGGGTTCTTTGTTAACAGTAGAATGCGATCTT

TGCCACTGACTGTAGTATTAATAAGGTTTTAATGTGAGATATTCCTGC

AAACCATCCCATTTCTACTGATTGTAAGTCAGAATTTCTTTTATCCCT

```
TTCAAATCAGTTTCTACATGTTTAAGTGTTCAGGGCTTCATCAGCATG
AGAAGTTTGTAATTACTGAAAGTCTGATTTCATTCAGGACACATTTTT
TCCTTCATATTTTTTCTGTGAATTTATAGGCTAGGAAGGCTATTGAAG
CCTCAATTATGGGTCTTCATTTTGAGATCGTTTTCTATGAGCTGAACT
GGAGATATCAATGGTTATCTCAAAATCGTCTTTTAGGAGATCCCCAAT
TGACTCAGAGTTTGAGGAGTTAGTATCACAGAATTAGATTTTTTTAAA
GCATTTGTACGTTTCCATTCCCAAATATGTAGCTGTGGTTCTTGAAAA
CACATCCTACATTGCATATGGGCATAGCAGTTTTTGACCCAGGCAGAA
TAAGTTAATATTTAATTAAATATTGCTTTGAAGATGGCGCTCTGGGCA
TGAGCATGGGGCTCCATGACTTCCCTTCTATCCCCATGAGCCCCTCCT
CCATCCAGCGACAAGCCATGGGCATGCATACAATGCAGCAAGACCAAC
ACAAGAGCAATATTGAATTGTTCATTCTATCTAAAATTACATGTATAT
AAAATATATAATTTATCTTCCTGCATTTTTGAAGTATAAAGTCATAAA
TTGTACATATCTGTAAGCTAGTATATTTGTTTCACTGTTTGTAATATT
TAAGAAATGCTCATTCTTTGTAGAACAAAAATGTATTAAATATTTTAA
AAATTGCTCTGTGATACTTAATTTTTTTCCCCAAAATTTGTAATGTGT
TGCTTCTACATAAGTTCTCTGGAAATATCTACAACTAATAGGACACAT
GTAAATCCTTGAAGACACATCCTGGAATTCATACCCCACAAGGACAGT
GTGTATACAAAGTATTTGCAGAGCATGACTTTTATATGTGTGGGATAT
CAATGTGTATATTTATATTTAAAGTGTATTTATTGTTACAAGTCTATT
CTCTATTATATTTTATTTACTCTGCGGTTATAAAAATCACCCTTGCAT
ACAAGTTTCTAGTTGCCAGTGATGTTCTGGAAATAATGGGAGATATTA
CAATAAAGCTACAGTTATGACACCCTG
```

Primers used:

Forward primer sequence:
        CTGGTGTTGAGGTTTGTGAAAGG

Reverse primer sequence:
        CCGTCGTGTCGGTGATCTG

Amplicon length: 124
Amplicon sequence:

```
CTGGTGTTGAGGTTTGTGAAAGGCACATTCCGGGAGAGCTACATCCCG
ACGGTGGAAGACACCTACCGGCAAGTGATCAGCTGTGACAAGAGCATA
TGCACATTGCAGATCACCGACACGACGG
```

4. RAB13, Member RAS Oncogene Family (RAB13)
Accession number: NM_002870
Sequence:

```
CTGGGCTCCGTGCCGCTCTGTTTGCCAACCGTCCAGTCCCGCCTACCA
GTGCCGGGCGCTCCCCACCCCTCCCCCGGCTCCCCCGGTGTCCGCCAT
GGCCAAAGCCTACGACCACCTCTTCAAGTTGCTGCTGATCGGGGACTC
GGGGGTGGGCAAGACTTGTCTGATCATTCGCTTTGCAGAGGACAACTT
```

```
CAACAACACTTACATCTCCACCATCGGAATTGATTTCAAGATCCGCAC
TGTGGATATAGAGGGGAAGAAGATCAAACTACAAGTCTGGGACACGGC
TGGCCAAGAGCGGTTCAAGACAATAACTACTGCCTACTACCGTGGAGC
CATGGGCATTATCCTAGTATACGACATCACGGATGAGAAATCTTTCGA
GAATATTCAGAACTGGATGAAAAGCATCAAGGAGAATGCCTCGGCTGG
GGTGGAGCGCCTCTTGCTGGGGAACAAATGTGACATGGAGGCCAAGAG
GAAGGTGCAGAAGGAGCAGGCCGATAAGTTGGCTCGAGAGCATGGAAT
CCGATTTTTCGAAACTAGTGCTAAATCCAGTATGAATGTGGATGAGGC
TTTTAGTTCCCTGGCCCGGGACATCTTGCTCAAGTCAGGAGGCCGGAG
ATCAGGAAACGGCAACAAGCCTCCCAGTACTGACCTGAAAACTTGTGA
CAAGAAGAACACCAACAAGTGCTCCCTGGGCTGAGGACCCTTTCTTGC
CTCCCCACCCCGGAAGCTGAACCTGAGGGAGACAACGGCAGAGGGAGT
GAGCAGGGGAGAAATAGCAGAGGGGCTTGGAGGGTCACATAGGTAGAT
GGTAAAGAGAATGAGGAGAAAAAGGAGAAAAGGGAAAAGCAGAAAGGA
AAAAAGGAAGAGAGAGGAAGGGAGAAGGGAGAGGAATGAATTGAGGA
AGTGAAAGAAGGCAAGGAGGTAGGAAGAGAGGGAGGAGGAAAGGAAGG
AGAGATGCCTCAGGCTTCAGACCTTACCTGGGTTTTCAGGGCAAACAT
AAATGTAAATACACTGATTTATTCTGTTACTAGATCAGGTTTTAGGGT
CCTGCAAAGGCTAGCTCGGCACTACACTAGGGAATTTGCTCCTGTTC
TGTCACTTGTCATGGTCTTTCTTGGTATTAAAGGCCACCATTTGCACA
AAAAAAAAAAAAAAAAAAAAAAAAAAAAAAAAAAAAAAAAAAAAAAAA
AAAAAAAAAA
```

Primers used:

Forward primer sequence:
        ATAACTACTGCCTACTACCGTGG

Reverse primer sequence:
        CCATGTCACATTTGTTCCCCAG

Amplicon length: 160
Amplicon sequence:

```
ATAACTACTGCCTACTACCGTGGAGCCATGGGCATTATCCTAGTATAC
GACATCACGGATGAGAAATCTTTCGAGAATATTCAGAACTGGATGAAA
AGCATCAAGGAGAATGCCTCGGCTGGGGTGGAGCGCCTCTTGCTGGGG
AACAAATGTGACATGG
```

5. Insulin-Like Growth Factor Binding Protein 7 (IGFBP7)
Accession number: NM_001553
Sequence:

```
GCCGCTGCCACCGCACCCCGCCATGGAGCGGCCGTCGCTGCGCGCCCT
GCTCCTCGGCGCCGCTGGGCTGCTGCTCCTGCTCCTGCCCCTCTCCTC
TTCCTCCTCTTCGGACACCTGCGGCCCCTGCGAGCCGGCCTCCTGCCC
GCCCCTGCCCCCGCTGGGCTGCCTGCTGGGCGAGACCCGCGACGCGTG
```

```
CGGCTGCTGCCCTATGTGCGCCCGCGGCGAGGGCGAGCCGTGCGGGGG

TGGCGGCGCCGGCAGGGGGTACTGCGCGCCGGGCATGGAGTGCGTGAA

GAGCCGCAAGAGGCGGAAGGGTAAAGCCGGGGCAGCAGCCGGCGGTCC

GGGTGTAAGCGGCGTGTGCGTGTGCAAGAGCCGCTACCCGGTGTGCGG

CAGCGACGGCACCACCTACCCGAGCGGCTGCCAGCTGCGCGCCGCCAG

CCAGAGGGCCGAGAGCCGCGGGGAGAAGGCCATCACCCAGGTCAGCAA

GGGCACCTGCGAGCAAGGTCCTTCCATAGTGACGCCCCCCAAGGACAT

CTGGAATGTCACTGGTGCCCAGGTGTACTTGAGCTGTGAGGTCATCGG

AATCCCGACACCTGTCCTCATCTGGAACAAGGTAAAAAGGGGTCACTA

TGGAGTTCAAAGGACAGAACTCCTGCCTGGTGACCGGGACAACCTGGC

CATTCAGACCCGGGGTGGCCCAGAAAAGCATGAAGTAACTGGCTGGGT

GCTGGTATCTCCTCTAAGTAAGGAAGATGCTGGAGAATATGAGTGCCA

TGCATCCAATTCCCAAGGACAGGCTTCAGCATCAGCAAAAATTACAGT

GGTTGATGCCTTACATGAAATACCAGTGAAAAAAGGTGAAGGTGCCGA

GCTATAAACCTCCAGAATATTATTAGTCTGCATGGTTAAAAGTAGTCA

TGGATAACTACATTACCTGTTCTTGCCTAATAAGTTTCTTTTAATCCA

ATCCACTAACACTTTAGTTATATTCACTGGTTTTACACAGAGAAATAC

AAAATAAAGATCACACATCAAGACTATCTACAAAAATTTATTATATAT

TTACAGAAGAAAAGCATGCATATCATTAAACAAATAAAATACTTTTTA

TCACAAAAAAAAAAAAAAA
```

Primers used:

```
                Forward primer sequence:
                GGTCCTTCCATAGTGACGCC Reverse primer sequence:
                TCTGAATGGCCAGGTTGTCC
```

Amplicon length: 184
Amplicon sequence:

```
GGTCCTTCCATAGTGACGCCCCCCAAGGACATCTGGAATGTCACTGGT

GCCCAGGTGTACTTGAGCTGTGAGGTCATCGGAATCCCGACACCTGTC

CTCATCTGGAACAAGGTAAAAAGGGGTCACTATGGAGTTCAAAGGACA

GAACTCCTGCCTGGTGACCGGGACAACCTGGCCATTCAGA
```

6. Collagen, Type VI, Alpha 1 (COL6A1)
Accession number: NM_001848
Sequence:

```
GCTCTCACTCTGGCTGGGAGCAGAAGGCAGCCTCGGTCTCTGGGCGGC

GGCGGCGGCCCACTCTGCCCTGGCCGCGCTGTGTGGTGACCGCAGGCC

CCAGACATGAGGGCGGCCCGTGCTCTGCTGCCCCTGCTGCTGCAGGCC

TGCTGGACAGCCGCGCAGGATGAGCCGGAGACCCCGAGGGCCGTGGCC

TTCCAGGACTGCCCCGTGGACCTGTTCTTTGTGCTGGACACCTCTGAG

AGCGTGGCCCTGAGGCTGAAGCCCTACGGGGCCCTCGTGGACAAAGTC

AAGTCCTTCACCAAGCGCTTCATCGACAACCTGAGGGACAGGTACTAC

CGCTGTGACCGAAACCTGGTGTGGAACGCAGGCGCGCTGCACTACAGT

GACGAGGTGGAGATCATCCAAGGCCTCACGCGCATGCCTGGCGGCCGC

GACGCACTCAAAAGCAGCGTGGACGCGGTCAAGTACTTTGGGAAGGGC

ACCTACACCGACTGCGCTATCAAGAAGGGGCTGGAGCAGCTCCTCGTG

GGGGGCTCCCACCTGAAGGAGAATAAGTACCTGATTGTGGTGACCGAC

GGGCACCCCCTGGAGGGCTACAAGGAACCCTGTGGGGGGCTGGAGGAT

GCTGTGAACGAGGCCAAGCACCTGGGCGTCAAAGTCTTCTCGGTGGCC

ATCACACCCGACCACCTGGAGCCGCGTCTGAGCATCATCGCCACGGAC

CACACGTACCGGCGCAACTTCACGGCGGCTGACTGGGGCCAGAGCCGC

GACGCAGAGGAGGCCATCAGCCAGACCATCGACACCATCGTGGACATG

ATCAAAAATAACGTGGAGCAAGTGTGCTGCTCCTTCGAATGCCAGCCT

GCAAGAGGACCTCCGGGGCTCCGGGGCGACCCCGGCTTTGAGGGAGAA

CGAGGCAAGCCGGGGCTCCCAGGAGAGAAGGGAGAAGCCGGAGATCCT

GGAAGACCCGGGGACCTCGGACCTGTTGGGTACCAGGGAATGAAGGGA

GAAAAAGGGAGCCGTGGGGAGAAGGGCTCCAGGGGACCCAAGGGCTAC

AAGGGAGAGAAGGGCAAGCGTGGCATCGACGGGGTGGACGGCGTGAAG

GGGGAGATGGGGTACCCAGGCCTGCCAGGCTGCAAGGGCTCGCCCGGG

TTTGACGGCATTCAAGGACCCCCTGGCCCCAAGGGAGACCCCGGTGCC

TTTGGACTGAAAGGAGAAAAGGGCGAGCCTGGAGCTGACGGGGAGGCG

GGGAGACCAGGGAGCTCGGGACCATCTGGAGACGAGGGCCAGCCGGGA

GAGCCTGGGCCCCCGGAGAGAAAGGAGAGGCGGGCGACGAGGGGAAC

CCAGGACCTGACGGTGCCCCCGGGGAGCGGGGTGGCCCTGGAGAGAGA

GGACCACGGGGACCCCAGGCACGCGGGGACCAAGAGGAGACCCTGGT

GAAGCTGGCCCGCAGGGTGATCAGGGAAGAGAAGGCCCCGTTGGTGTC

CCTGGAGACCCGGGCGAGGCTGGCCCTATCGGACCTAAAGGCTACCGA

GGCGATGAGGGTCCCCCAGGGTCCGAGGGTGCCAGAGGAGCCCCAGGA

CCTGCCGGACCCCCTGGAGACCCGGGGCTGATGGGTGAAAGGGGAGAA

GACGGCCCCGCTGGAAATGGCACCGAGGGCTTCCCCGGCTTCCCCGGG

TATCCGGGCAACAGGGGCGCTCCCGGGATAAACGGCACGAAGGGCTAC

CCCGGCCTCAAGGGGGACGAGGGAGAAGCCGGGGACCCCGGAGACGAT

AACAACGACATTGCACCCCGAGGAGTCAAAGGAGCAAAGGGGTACCGG

GGTCCCGAGGGCCCCCAGGGACCCCCAGGACACCAAGGACCGCCTGGG

CCGGACGAATGCGAGATTTTGGACATCATCATGAAAATGTGCTCTTGC

TGTGAATGCAAGTGCGGCCCCATCGACCTCCTGTTCGTGCTGGACAGC

TCAGAGAGCATTGGCCTGCAGAACTTCGAGATTGCCAAGGACTTCGTC

GTCAAGGTCATCGACCGGCTGAGCCGGGACGAGCTGGTCAAGTTCGAG

CCAGGGCAGTCGTACGCGGGTGTGGTGCAGTACAGCCACAGCCAGATG

CAGGAGCACGTGAGCCTGCGCAGCCCCAGCATCCGGAACGTGCAGGAG

CTCAAGGAAGCCATCAAGAGCCTGCAGTGGATGCGGGCGGCACCTTC

ACGGGGGAGGCCCTGCAGTACACGCGGGACCAGCTGCTGCCGCCCAGC
```

```
CCGAACAACCGCATCGCCCTGGTCATCACTGACGGGCGCTCAGACACT
CAGAGGGACACCACACCGCTCAACGTGCTCTGCAGCCCCGGCATCCAG
GTGGTCTCCGTGGGCATCAAAGACGTGTTTGACTTCATCCCAGGCTCA
GACCAGCTCAATGTCATTTCTTGCCAAGGCCTGGCACCATCCCAGGGC
CGGCCCGGCCTCTCGCTGGTCAAGGAGAACTATGCAGAGCTGCTGGAG
GATGCCTTCCTGAAGAATGTCACCGCCCAGATCTGCATAGACAAGAAG
TGTCCAGATTACACCTGCCCCATCACGTTCTCCTCCCCGGCTGACATC
ACCATCCTGCTGGACGGCTCCGCCAGCGTGGGCAGCCACAACTTTGAC
ACCACCAAGCGCTTCGCCAAGCGCCTGGCCGAGCGCTTCCTCACAGCG
GGCAGGACGGACCCCGCCCACGACGTGCGGGTGGCGGTGGTGCAGTAC
AGCGGCACGGGCCAGCAGCGCCCAGAGCGGGCGTCGCTGCAGTTCCTG
CAGAACTACACGGCCCTGGCCAGTGCCGTCGATGCCATGGACTTTATC
AACGACGCCACCGACGTCAACGATGCCCTGGGCTATGTGACCCGCTTC
TACCGCGAGGCCTCGTCCGGCGCTGCCAAGAAGAGGCTGCTGCTCTTC
TCAGATGGCAACTCGCAGGGCGCCACGCCCGCTGCCATCGAGAAGGCC
GTGCAGGAAGCCCAGCGGGCAGGCATCGAGATCTTCGTGGTGGTCGTG
GGCCGCCAGGTGAATGAGCCCCACATCCGCGTCCTGGTCACCGGCAAG
ACGGCCGAGTACGACGTGGCCTACGGCGAGAGCCACCTGTTCCGTGTC
CCCAGCTACCAGGCCCTGCTCCGCGGTGTCTTCCACCAGACAGTCTCC
AGGAAGGTGGCGCTGGGCTAGCCCACCCTGCACGCCGGCACCAAACCC
TGTCCTCCCACCCCTCCCCACTCATCACTAAACAGAGTAAAATGTGAT
GCGAATTTTCCCGACCAACCTGATTCGCTAGATTTTTTTAAGGAAAA
GCTTGGAAAGCCAGGACACAACGCTGCTGCCTGCTTTGTGCAGGGTCC
TCCGGGGCTCAGCCCTGAGTTGGCATCACCTGCGCAGGGCCCTCTGGG
GCTCAGCCCTGAGCTAGTGTCACCTGCACAGGGCCCTCTGAGGCTCAG
CCCTGAGCTGGCGTCACCTGTGCAGGGCCCTCTGGGGCTCAGCCCTGA
GCTGGCCTCACCTGGGTTCCCCACCCCGGGCTCTCCTGCCCTGCCCTC
CTGCCCGCCCTCCCTCCTGCCTGCGCAGCTCCTTCCCTAGGCACCTCT
GTGCTGCATCCCACCAGCCTGAGCAAGACGCCCTCTCGGGGCCTGTGC
CGCACTAGCCTCCCTCTCCTCTGTCCCCATAGCTGGTTTTTCCCACCA
ATCCTCACCTAACAGTTACTTTACAATTAAACTCAAAGCAAGCTCTTC
TCCTCAGCTTGGGGCAGCCATTGGCCTCTGTCTCGTTTTGGGAAACCA
AGGTCAGGAGGCCGTTGCAGACATAAATCTCGGCGACTCGGCCCCGTC
TCCTGAGGGTCCTGCTGGTGACCGGCCTGGACCTTGGCCCTACAGCCC
TGGAGGCCGCTGCTGACCAGCACTGACCCCGACCTCAGAGAGTACTCG
CAGGGGCGCTGGCTGCACTCAAGACCCTCGAGATTAACGGTGCTAACC
CCGTCTGCTCCTCCCTCCCGCAGAGACTGGGGCCTGGACTGGACATGA
GAGCCCCTTGGTGCCACAGAGGGCTGTGTCTTACTAGAAACAACGCAA
ACCTCTCCTTCCTCAGAATAGTGATGTGTTCGACGTTTTATCAAAGGC
CCCCTTTCTATGTTCATGTTAGTTTTGCTCCTTCTGTGTTTTTTTCTG
AACCATATCCATGTTGCTGACTTTTCCAAATAAAGGTTTTCACTCCT
CTAAAAAAAAAAAAAAAAAAAA
```

Primers used:

```
Forward primer sequence:
ACAGTGACGAGGTGGAGATCA

Reverse primer sequence:
GATAGCGCAGTCGGTGTAGG
```

Amplicon length: 122
Amplicon sequence:

```
ACAGTGACGAGGTGGAGATCATCCAAGGCCTCACGCGCATGCCTGGCG
GCCGCGACGCACTCAAAAGCAGCGTGGACGCGGTCAAGTACTTTGGGA
AGGGCACCTACACCGACTGCGCTATC
```

7. Decorin (DCN)
Accession number: NM 001920
Sequence:

```
>gi|47419925|ref|NM_001920.3| Homo sapiens
decorin (DCN), transcript variant A1, mRNA
GAATCTACAATAAGACAAATTTCAAATCAAGTTGCTCCACTATACTGC
ATAAGCAGTTTAGAATCTTAAGCAGATGCAAAAAGAATAAAGCAAATG
GGAGGAAAAAAAGGCCGATAAAGTTTCTGGCTACAATACAAGAGACA
TATCATTACCATATGATCTAATGTGGGTGTCAGCCGGATTGTGTTCAT
TGAGGGAAACCTTATTTTTTAACTGTGCTATGGAGTAGAAGCAGGAGG
TTTTCAACCTAGTCACAGAGCAGCACCTACCCCCTCCTCCTTTCCACA
CCTGCAAACTCTTTTACTTGGGCTGAATATTTAGTGTAATTACATCTC
AGCTTTGAGGGCTCCTGTGGCAAATTCCCGGATTAAAAGGTTCCCTGG
TTGTGAAAATACATGAGATAAATCATGAAGGCCACTATCATCCTCCTT
CTGCTTGCACAAGTTTCCTGGGCTGGACCGTTTCAACAGAGAGGCTTA
TTTGACTTTATGCTAGAAGATGAGGCTTCTGGGATAGGCCCAGAAGTT
CCTGATGACCGCGACTTCGAGCCCTCCCTAGGCCCAGTGTGCCCCTTC
CGCTGTCAATGCCATCTTCGAGTGGTCCAGTGTTCTGATTTGGGTCTG
GACAAAGTGCCAAAGGATCTTCCCCCTGACACAACTCTGCTAGACCTG
CAAAACAACAAAATAACCGAAATCAAAGATGGAGACTTTAAGAACCTG
AAGAACCTTCACGCATTGATTCTTGTCAACAATAAAATTAGCAAAGTT
AGTCCTGGAGCATTTACACCTTTGGTGAAGTTGGAACGACTTTATCTG
TCCAAGAATCAGCTGAAGGAATTGCCAGAAAAAATGCCCAAAACTCTT
CAGGAGCTGCGTGCCCATGAGAATGAGATCACCAAAGTGCGAAAAGTT
ACTTTCAATGGACTGAACCAGATGATTGTCATAGAACTGGGCACCAAT
CCGCTGAAGAGCTCAGGAATTGAAAATGGGGCTTTCCAGGGAATGAAG
AAGCTCTCCTACATCCGCATTGCTGATACCAATATCACCAGCATTCCT
CAAGGTCTTCCTCCTTCCCTTACGGAATTACATCTTGATGGCAACAAA
ATCAGCAGAGTTGATGCAGCTAGCCTGAAAGGACTGAATAATTTGGCT
```

-continued

```
AAGTTGGGATTGAGTTTCAACAGCATCTCTGCTGTTGACAATGGCTCT
CTGGCCAACACGCCTCATCTGAGGGAGCTTCACTTGGACAACAACAAG
CTTACCAGAGTACCTGGTGGGCTGGCAGAGCATAAGTACATCCAGGTT
GTCTACCTTCATAACAACAATATCTCTGTAGTTGGATCAAGTGACTTC
TGCCCACCTGGACACAACACCAAAAAGGCTTCTTATTCGGGTGTGAGT
CTTTTCAGCAACCCGGTCCAGTACTGGGAGATACAGCCATCCACCTTC
AGATGTGTCTACGTGCGCTCTGCCATTCAACTCGGAAACTATAAGTAA
TTCTCAAGAAAGCCCTCATTTTTATAACCTGGCAAAATCTTGTTAATG
TCATTGCTAAAAATAAATAAAAGCTAGATACTGGAAACCTAACTGCA
ATGTGGATGTTTTACCCACATGACTTATTATGCATAAAGCCAAATTTC
CAGTTTAAGTAATTGCCTACAATAAAAAGAAATTTTGCCTGCCATTTT
CAGAATCATCTTTTGAAGCTTTCTGTTGATGTTAACTGAGCTACTAGA
GATATTCTTATTTCACTAAATGTAAAATTTGGAGTAAATATATATGTC
AATATTTAGTAAAGCTTTTCTTTTTTAATTTCCAGGAAAAAATAAAAA
GAGTATGAGTCTTCTGTAATTCATTGAGCAGTTAGCTCATTTGAGATA
AAGTCAAATGCCAAACACTAGCTCTGTATTAATCCCCATCATTACTGG
TAAAGCCTCATTTGAATGTGTGAATTCAATACAGGCTATGTAAAATTT
TTACTAATGTCATTATTTTGAAAAAATAAATTTAAAAATACATTCAAA
ATTACTATTGTATACAAGCTTAATTGTTAATATTCCCTAAACACAATT
TTATGAAGGGAGAAGACATTGGTTTGTTGACAATAACAGTACATCTTT
TCAAGTTCTCAGCTATTTCTTCTACCTCTCCCTATCTTACATTTGAGT
ATGGTAACTTATGTCATCTATGTTGAATGTAAGCTTATAAAGCACAAA
GCATACATTTCCTGACTGGTCTAGAGAACTGATGTTTCAATTTACCCC
TCTGCTAAATAAATATTAAAACTATCATGTGAAAAAAAAAAAAAAA
AA
```

Primers used:

```
Forward primer sequence:
AGTTGGAACGACTTTATCTGTCC

Reverse primer sequence:
GTGCCCAGTTCTATGACAATCA
```

Amplicon length: 160
Amplicon sequence:

```
AGTTGGAACGACTTTATCTGTCCAAGAATCAGCTGAAGGAATTGCCAG
AAAAAATGCCCAAAACTCTTCAGGAGCTGCGTGCCCATGAGAATGAGA
TCACCAAAGTGCGAAAAGTTACTTTCAATGGACTGAACCAGATGATTG
TCATAGAACTGGGCAC
```

8. Plasminogen Activator, Tissue (PLAT)
   Accession number: N_000930
   Sequence:

```
ATGGCCCTGTCCACTGAGCATCCTCCCGCCACACAGAAACCCGCCCAG
CCGGGGCCACCGACCCCACCCCCTGCCTGGAAACTTAAAGGAGGCCGG
```

-continued

```
AGCTGTGGGGAGCTCAGAGCTGAGATCCTACAGGAGTCCAGGGCTGGA
GAGAAAACCTCTGCGAGGAAAGGGAAGGAGCAAGCCGTGAATTTAAGG
GACGCTGTGAAGCAATCATGGATGCAATGAAGAGAGGGCTCTGCTGTG
TGCTGCTGCTGTGTGGAGCAGTCTTCGTTTCGCCCAGCCAGGAAATCC
ATGCCCGATTCAGAAGAGGAGCCAGATCTTACCAAGTGATCTGCAGAG
ATGAAAAAACGCAGATGATATACCAGCAACATCAGTCATGGCTGCGCC
CTGTGCTCAGAAGCAACCGGGTGGAATATTGCTGGTGCAACAGTGGCA
GGGCACAGTGCCACTCAGTGCCTGTCAAAAGTTGCAGCGAGCCAAGGT
GTTTCAACGGGGGCACCTGCCAGCAGGCCCTGTACTTCTCAGATTTCG
TGTGCCAGTGCCCCGAAGGATTTGCTGGGAAGTGCTGTGAAATAGATA
CCAGGGCCACGTGCTACGAGGACCAGGGCATCAGCTACAGGGGCACGT
GGAGCACAGCCGGAGAGTGGCGCCGAGTGCACCAACTGGAACAGCAGCG
CGTTGGCCCAGAAGCCCTACAGCGGGCGGAGGCCAGACGCCATCAGGC
TGGGCCTGGGGAACCACAACTACTGCAGAAACCCAGATCGAGACTCAA
AGCCCTGGTGCTACGTCTTTAAGGCGGGGAAGTACAGCTCAGAGTTCT
GCAGCACCCCTGCCTGCTCTGAGGGAAACAGTGACTGCTACTTTGGGA
ATGGGTCAGCCTACCGTGGCACGCACAGCCTCACCGAGTCGGGTGCCT
CCTGCCTCCCGTGGAATTCCATGATCCTGATAGGCAAGGTTTACACAG
CACAGAACCCCAGTGCCCAGGCACTGGGCCTGGGCAAACATAATTACT
GCCGGAATCCTGATGGGGATGCCAAGCCCTGGTGCCACGTGCTGAAGA
ACCGCAGGCTGACGTGGGAGTACTGTGATGTGCCCTCCTGCTCCACCT
GCGGCCTGAGACAGTACAGCCAGCCTCAGTTTCGCATCAAAGGAGGGC
TCTTCGCCGACATCGCCTCCCACCCCTGGCAGGCTGCCATCTTTGCCA
AGCACAGGAGGTCGCCCGGAGAGCGGTTCCTGTGCGGGGCATACTCA
TCAGCTCCTGCTGGATTCTCTCTGCCGCCCACTGCTTCCAGGAGAGGT
TTCCGCCCCACCACCTGACGGTGATCTTGGGCAGAACATACCGGGTGG
TCCCTGGCGAGGAGGAGCAGAAATTTGAAGTCGAAAAATACATTGTCC
ATAAGGAATTCGATGATGACACTTACGACAATGACATTGCGCTGCTGC
AGCTGAAATCGGATTCGTCCCGCTGTGCCCAGGAGAGCAGCGTGGTCC
GCACTGTGTGCCTTCCCCCGGCGGACCTGCAGCTGCCGGACTGGACGG
AGTGTGAGCTCTCCGGCTACGGCAAGCATGAGGCCTTGTCTCCTTTCT
ATTCGGAGCGGCTGAAGGAGGCTCATGTCAGACTGTACCCATCCAGCC
GCTGCACATCACAACATTTACTTAACAGAACAGTCACCGACAACATGC
TGTGTGCTGGAGACACTCGGAGCGGCGGGCCCCAGGCAAACTTGCACG
ACGCCTGCCAGGGCGATTCGGGAGGCCCCCTGGTGTGTCTGAACGATG
GCCGCATGACTTTGGTGGGCATCATCAGCTGGGGCCTGGGCTGTGGAC
AGAAGGATGTCCCGGGTGTGTACACCAAGGTTACCAACTACCTAGACT
GGATTCGTGACAACATGCGACCGTGACCAGGAACACCCGACTCCTCAA
AAGCAAATGAGATCCCGCCTCTTCTTCTTCAGAAGACACTGCAAAGGC
GCAGTGCTTCTCTACAGACTTCTCCAGACCCACCACACCGCAGAAGCG
```

```
GGACGAGACCCTACAGGAGAGGGAAGAGTGCATTTTCCCAGATACTTC
CCATTTTGGAAGTTTTCAGGACTTGGTCTGATTTCAGGATACTCTGTC
AGATGGGAAGACATGAATGCACACTAGCCTCTCCAGGAATGCCTCCTC
CCTGGGCAGAAAGTGGCCATGCCACCCTGTTTTCAGCTAAAGCCCAAC
CTCCTGACCTGTCACCGTGAGCAGCTTTGGAAACAGGACCACAAAAT
GAAAGCATGTCTCAATAGTAAAAGATAACAAGATCTTTCAGGAAAGAC
GGATTGCATTAGAAATAGACAGTATATTTATAGTCACAAGAGCCCAGC
AGGGCCTCAAAGTTGGGGCAGGCTGGCTGGCCCGTCATGTTCCTCAAA
AGCACCCTTGACGTCAAGTCTCCTTCCCCTTTCCCCACTCCCTGGCTC
TCAGAAGGTATTCCTTTTGTGTACAGTGTGTAAAGTGTAAATCCTTTT
TCTTTATAAACTTTAGAGTAGCATGAGAGAATTGTATCATTTGAACAA
CTAGGCTTCAGCATATTTATAGCAATCCATGTTAGTTTTTACTTTCTG
TTGCCACAACCCTGTTTTATACTGTACTTAATAAATTCAGATATATTT
TTCACAGTTTTTCCAAAATCAGAGTGGAATGGTTTTGTTATAGATGCT
GTATCCCACTCTTTATTCATGTTCACATTTTAAAATCATTTGGAATTC
TGCTTCACTCGCTTAACATATACACAACACCTGTAACATACAAGGCAA
TGGGCTAGGTGCTCCAGACCGGGAAAAGGAGGGACAGGAATGCTTGGT
CTGATGGGCTAATATGGCATTTAGAGAAGTACCAAGGTACAGTGGAGC
CGGTCACAAAAGGGCAGACTTGTAGTAGAATTCAGTTGCAAGAGGGAT
TGGGGAATCTTAAGGAAAAAATAGAATCTTAAGGAAAAAATAACTGGG
TGAGACGTGGACTGTGGACAGGTGTGGAAAAGGCACTCTCCATGGAGG
TATGAATATGTAGAGGGCCAAGAGAGGGGAGTACAGGGAGAAATGAGT
TGAGCTTGTCTGAAGTGAACTTCAGGAAGAGGAACATAGGCTGGAATT
TAGATTATGGGGCTCTGAACACCAAACTGAGTTTGGACTTAATTGAC
TTCTG
```

Primers used:

```
Forward primer sequence:
ACTGCCGGAATCCTGATGG

Reverse primer sequence:
TGTGCTTGGCAAAGATGGC
```

Amplicon length: 201
Amplicon sequence:

```
ACTGCCGGAATCCTGATGGGGATGCCAAGCCCTGGTGCCACGTGCTGA
AGAACCGCAGGCTGACGTGGGAGTACTGTGATGTGCCCTCCTGCTCCA
CCTGCGGCCTGAGACAGTACAGCCAGCCTCAGTTTCGCATCAAAGGAG
GGCTCTTCGCCGACATCGCCTCCCACCCCTGGCAGGCTGCCATCTTTG
CCAAGCACA
```

9. Lectin, Galactoside-Binding, Soluble, 3 (LGALS3)
Accession number: NM_002306.
Sequence:

```
GGAGAGGACTGGCTGGGCAGGGGCGCCGCCCCGCCTCGGGAGAGGCGG
GCCGGGCGGGGCTGGGAGTATTTGAGGCTCGGAGCCACCGCCCCGCCG
GCGCCCGCAGCACCTCCTCGCCAGCAGCCGTCCGGAGCCAGCCAACGA
GCGGAAAATGGCAGACAATTTTTCGCTCCATGATGCGTTATCTGGGTC
TGGAAACCCAAACCCTCAAGGATGGCCTGGCGCATGGGGAACCAGCC
TGCTGGGGCAGGGGGCTACCCAGGGGCTTCCTATCCTGGGGCCTACCC
CGGGCAGGCACCCCCAGGGGCTTATCCTGGACAGGCACCTCCAGGCGC
CTACCCTGGAGCACCTGGAGCTTATCCCGGAGCACCTGCACCTGGAGT
CTACCCAGGGCCACCCAGCGGCCCTGGGGCCTACCCATCTTCTGGACA
GCCAAGTGCCACCGGAGCCTACCCTGCCACTGGCCCCTATGGCGCCCC
TGCTGGGCCACTGATTGTGCCTTATAACCTGCCTTTGCCTGGGGGAGT
GGTGCCTCGCATGCTGATAACAATTCTGGGCACGGTGAAGCCCAATGC
AAACAGAATTGCTTTAGATTTCCAAAGAGGGAATGATGTTGCCTTCCA
CTTTAACCCACGCTTCAATGAGAACAACAGGAGAGTCATTGTTTGCAA
TACAAAGCTGGATAATAACTGGGGAAGGGAAGAAAGACAGTCGGTTTT
CCCATTTGAAAGTGGGAAACCATTCAAAATACAAGTACTGGTTGAACC
TGACCACTTCAAGGTTGCAGTGAATGATGCTCACTTGTTGCAGTACAA
TCATCGGGTTAAAAAACTCAATGAAATCAGCAAACTGGGAATTTCTGG
TGACATAGACCTCACCAGTGCTTCATATACCATGATATAATCTGAAAG
GGGCAGATTAAAAAAAAAAAAGAATCTAAACCTTACATGTGTAAAGG
TTTCATGTTCACTGTGAGTGAAAATTTTTACATTCATCAATATCCCTC
TTGTAAGTCATCTACTTAATAAATATTACAGTGAATTACCTGTCTCAA
TATGTCAAAAAAAAAAAAAAAAA
```

Primers used:

```
Forward primer sequence:
TGCTGATAACAATTCTGGGCAC

Reverse primer sequence:
TGAAGCGTGGGTTAAAGTGGA
```

Amplicon length: 102
Amplicon sequence:

```
TGCTGATAACAATTCTGGGCACGGTGAAGCCCAATGCAAACAGAATTG
CTTTAGATTTCCAAAGAGGGAATGATGTTGCCTTCCACTTTAACCCAC
GCTTCA
```

10. Fatty Acid Binding Protein 7, Brain (FABP7)
Accession number: NM_001446.
Sequence:

```
GAGGATTGGGAGGAACTCGACCTACTCCGCTAACCCAGTGGCCTGAGC
CAATCACAAAGAGGATTGGAGCCTCACTCGAGCGCTCCTTCCCTTCTC
CTCTCTCTGTGACAGCCTCTTGGAAAGAGGGACACTGGAGGGGTGTGT
TTGCAATTTAAATCACTGGATTTTTGCCCACCCTCTTTCCAAATAAGA
AGGCAGGAGCTGCTTGCTGAGGTGTAAAGGGTCTTCTGAGCTGCAGTG
GCAATTAGACCAGAAGATCCCCGCTCCTGTCTCTAAAGAGGGGAAAGG
```

-continued

```
GCAAGGATGGTGGAGGCTTTCTGTGCTACCTGGAAGCTGACCAACAGT
CAGAACTTTGATGAGTACATGAAGGCTCTAGGCGTGGGCTTTGCCACT
AGGCAGGTGGGAAATGTGACCAAACCAACGGTAATTATCAGTCAAGAA
GGAGACAAAGTGGTCATCAGGACTCTCAGCACATTCAAGAACACGGAG
ATTAGTTTCCAGCTGGGAGAAGAGTTTGATGAAACCACTGCAGATGAT
AGAAACTGTAAGTCTGTTGTTAGCCTGGATGGAGACAAACTTGTTCAC
ATACAGAAATGGGATGGCAAAGAAACAAATTTTGTAAGAGAAATTAAG
GATGGCAAAATGGTTATGACCCTTACTTTTGGTGATGTGGTTGCTGTT
CGCCACTATGAGAAGGCATAAAAATGTTCCTGGTCGGGCTTGGAAGA
GCTCTTCAGTTTTTCTGTTTCCTCAAGTCTCAGTGCTATCCTATTACA
ACATGGCTGATCATTAATTAGAAGGTTATCCTTGGTGTGGAGGTGGAA
AATGGTGATTTAAAAACTTGTTACTCCAAGCAACTTGCCCAATTTTAA
TCTGAAAATTTATCATGTTTTATAATTTGAATTAAAGTTTTGTCCCCC
CCCCCCTTTTTTTTATAAACAAGTGAATACATTTTATAATTTCTTTTG
GAATGTAAATCAAATTTGAATAAAAATCTTACACGTGAAAAAAAA
```

Primers used:

```
Forward primer sequence:
CTCTCAGCACATTCAAGAACACG

Reverse primer sequence:
GCGAACAGCAACCACATCAC
```

Amplicon length: 221
Amplicon sequence

```
CTCTCAGCACATTCAAGAACACGGAGATTAGTTTCCAGCTGGGAGAAG
AGTTTGATGAAACCACTGCAGATGATAGAAACTGTAAGTCTGTTGTTA
GCCTGGATGGAGACAAACTTGTTCACATACAGAAATGGGATGGCAAAG
AAACAAATTTTGTAAGAGAAATTAAGGATGGCAAAATGGTTATGACCC
TTACTTTTGGTGATGTGGTTGCTGTTCGC
```

11. Lysyl Oxidase (LOX)
Accession number: NM_002317
Sequence:

```
ATTACGTGAACAAATAGCTGAGGGGCGGCCGGGCCAGAACGGCTTGTG
TAACTTTGCAAACGTGCCAGAAAGTTTAAAATCTCTCCTCCTTCCTTC
ACTCCAGACACTGCCCGCTCTCCGGGACTGCCGCGCCGCTCCCCGTTG
CCTTCCAGGACTGAGAAAGGGGAAAGGGAAGGGTGCCACGTCCGAGCA
GCCGCCTTGACTGGGGAAGGGTCTGAATCCCACCCTTGGCATTGCTTG
GTGGAGACTGAGATACCCGTGCTCCGCTCGCCTCCTTGGTTGAAGATT
TCTCCTTCCCTCACGTGATTTGAGCCCCGTTTTTATTTTCTGTGAGCC
ACGTCCTCCTCGAGCGGGGTCAATCTGGCAAAAGGAGTGATGCGCTTC
GCCTGGACCGTGCTCCTGCTCGGGCCTTTGCAGCTCTGCGCGCTAGTG
CACTGCGCCCCTCCCGCCGCCGGCCAACAGCAGCCCCGCGCGAGCCG
CCGGCGGCTCCGGGCGCCTGGCGCCAGCAGATCCAATGGGAGAACAAC
GGGCAGGTGTTCAGCTTGCTGAGCCTGGGCTCACAGTACCAGCCTCAG
CGCCGCCGGGACCCGGGCGCCGCCGTCCCTGGTGCAGCCAACGCCTCC
GCCCAGCAGCCCCGCACTCCGATCCTGCTGATCCGCGACAACCGCACC
GCCGCGGCGCGAACGCGGACGGCCGGCTCATCTGGAGTCACCGCTGGC
CGCCCCAGGCCCACCGCCCGTCACTGGTTCCAAGCTGGCTACTCGACA
TCTAGAGCCCGCGAAGCTGGCGCCTCGCGCGGGAGAACCAGACAGCG
CCGGGAGAAGTTCCTGCGCTCAGTAACCTGCGGCCGCCCAGCCGCGTG
GACGGCATGGTGGGCGACGACCCTTACAACCCCTACAAGTACTCTGAC
GACAACCCTTATTACAACTACTACGATACTTATGAAAGGCCCAGACCT
GGGGGCAGGTACCGGCCCGGATACGGCACTGGCTACTTCCAGTACGGT
CTCCCAGACCTGGTGGCCGACCCCTACTACATCCAGGCGTCCACGTAC
GTGCAGAAGATGTCCATGTACAACCTGAGATGCGCGGCGGAGGAAAAC
TGTCTGGCCAGTACAGCATACAGGGCAGATGTCAGAGATTATGATCAC
AGGGTGCTGCTCAGATTTCCCCAAAGAGTGAAAAACCAAGGGACATCA
GATTTCTTACCCAGCCGACCAAGATATTCCTGGGAATGGCACAGTTGT
CATCAACATTACCACAGTATGGATGAGTTTAGCCACTATGACCTGCTT
GATGCCAACACCCAGAGGAGAGTGGCTGAAGGCCACAAAGCAAGTTTC
TGTCTTGAAGACACATCCTGTGACTATGGCTACCACAGGCGATTTGCA
TGTACTGCACACACACAGGGATTGAGTCCTGGCTGTTATGATACCTAT
GGTGCAGACATAGACTGCCAGTGGATTGATATTACAGATGTAAAACCT
GGAAACTATATCCTAAAGGTCAGTGTAAACCCCAGCTACCTGGTTCCT
GAATCTGACTATACCAACAATGTTGTGCGCTGTGACATTCGCTACACA
GGACATCATGCGTATGCCTCAGGCTGCACAATTTCACCGTATTAGAAG
GCAAAGCAAAACTCCCAATGGATAAATCAGTGCCTGGTGTTCTGAAGT
GGGAAAAAATAGACTAACTTCAGTAGGATTTATGTATTTTGAAAAAGA
GAACAGAAAACAACAAAAGAATTTTTGTTTGGACTGTTTTCAATAACA
AAGCACATAACTGGATTTTGAACGCTTAAGTCATCATTACTTGGGAAA
TTTTTAATGTTTATTATTTACATCACTTTGTGAATTAACACAGTGTTT
CAATTCTGTAATTACATATTTGACTCTTTCAAAGAAATCCAAATTTCT
CATGTTCCTTTTGAAATTGTAGTGCAAAATGGTCAGTATTATCTAAAT
GAATGAGCCAAAATGACTTTGAACTGAAACTTTTCTAAAGTGCTGGAA
CTTTAGTGAAACATAATAATAATGGGTTTATATATGTCATAGCATAGA
TGAATTTAGAAACAATGCTCCTACTGTTTAAATACATATGGACACATC
TGGTGCTGAGAAAGAAACAAACACATTACCATTGGTGTCAAGAAATAT
TACTATATAGCAGAGAAATGGCAATACATGTACTCAGATAGTTACATC
CCTATATAAAAAGTATGTTTACATTTAAAAAATTAGTAGATAACTTCC
TTTCTTTCAAGTGCACAATTTCATTTTGACTTGAGTCAACTTTTGTTT
TGGAACAAATTAAGTAAGGGAGCTGCCCAATCCTGTCTGATATTTCTT
GAGGCTGCCCTCTATCATTTTATCTTTCCCATGGGCAGAGATGTTGTA
AGTGGGATTCTTAATATCACCATTCTTGGGACTGGTATACATAAGGCA
```

-continued

GCCGTGAAACTGGAAAGTCATTTTGATGACTGATGTGATACATCCAGA

GGTAAAATGCATTTAAACATATTAAAGTATTTGCCAAAGATACAATTT

TCTTGCTGACATAAAAATCACACAAACAAGTCCCCCCCAAACCACAAC

TGTCTCTCAAATAGCTTAAAAAAATTGAAAAACATTTTAGGATTTTTC

AAGTTTTCTAGATTTTAAAAAGATGTTCAGCTATTAGAGGAATGTTAA

AAATTTTATATTATCTAGAACACAGGAACATCATCCTGGGTTATTCAG

GAATCAGTCACACATGTGTGTGTCTGAGATATAGTCTAAATTAGCA

AAGCACATAGTATTACATACTTGAGGGGTTGGTGAACAAAGGAAAAAT

ATACTTTCTGCAAAACCAAGGACTGTGCTGCGTAATGAGACAGCTGTG

ATTTCATTTGAAACTGTGAAACCATGTGCCATAATAGAATTTTGAGAA

TTTTGCTTTTACCTAAATTCAAGAAAATGAAATTACACTTTTAAGTTA

GTGGTGCTTAAGCATAATTTTTCCTATATTAACCAGTATTAAAATCTC

AAGTAAGATTTTCCAGTGCCAGAACATGTTAGGTGGAATTTTAAAAGT

GCCTCGGCATCCTGTATTACATGTCATAGAATTGTAAAGTCAACATCA

ATTACTAGTAATCATTCTGCACTCACTGGGTGCATAGCATGGTTAGAG

GGGCTAGAGATGGACAGTCATCAACTGGCGGATATAGCGGTACATATG

ATCCTTAGCCACCAGGGCACAAGCTTACCAGTAGACAATACAGACAGA

GCTTTTGTTGAGCTGTAACTGAGCTATGGAATAGCTTCTTTGATGTAC

CTCTTTGCCTTAAATTGCTTTTTAGTTCTAAGATTGTAGAATGATCCT

TTCAAATTGTAATCTTTTCTAACAGAGATATTTTAATATACTTGCTTT

CTTAAAAAACAAAAAAACTACTGTCAGTATTAATACTGAGCCAGACTG

GCATCTACAGATTTCAGATCTATCATTTTATTGATTCTTAAGCTTGTA

TTAAAAACTAGGCAATATCATCATGGATACATAGGAGAAGACACATTT

ACAATCATTCATTGGGCCTTTTATCTGTCTATCCATCCATCATCATTT

GAAGGCCTAATATATGCCAAGTACTCACATGGTATGCATTGAGACATA

AAAAAGACTGTCTATAACCTCAATAAGTATTAAAAATCCCATTATTAC

CCATAAGGTTCATCTTATTTCATTTTTAGGGAATAAAATTACATGTCT

ATGAAATTTCAATTTTAAGCACTATTGTTTTTCATGACCATAATTTAT

TTTTAAAAATAAATTAAAGGTTAATTATATGCATGTATGTATTTCTAA

TAATTAAAAATGTGTTCAATCCCTGAAATGTCTGCCTTTTAAATATAA

CACCTACTATTTGGTTAAAAAAAAAAAAAAAAAAAAA

Primers used:

```
Forward primer sequence:
CAGGGTGCTGCTCAGATTTCC

Reverse primer sequence:
GGTAATGTTGATGACAACTGTGC
```

Amplicon length: 110
Amplicon sequence:

CAGGGTGCTGCTCAGATTTCCCCAAAGAGTGAAAAACCAAGGGACATCAG

ATTTCTTACCCAGCCGACCAAGATATTCCTGGGAATGGCACAGTTGTCAT

CAACATTACC

12. Laminin, Beta 1 (LAMB1)
Accession number: NM_002291
Sequence:

GGGACCTGGAAGCGCCCCAGCCCCGCAGCGATCGCAGATTCGGCTTTCAA

ACAAAAGAGGCGCCCCGGGGGGTGGGACCGGGACCTCACCCGGTCCTCGC

AGAGTTGCGGCCGCCCGCCCCTTCAGCCCCGGCTCTCCGTATGCGCATGA

GCAGAGGCGCCTCCCTCTGTTCCTCCCAAGGCTAAACTTTCTAATTCCCT

TCTTTGGGCTCGGGGGCTCCCGGAGCAGGGCGAGAGCTCGCGTCGCCGGA

AAGGAAGACGGGAAGAAAGGGCAGGCGGCTCGGCGGGCGTCTTCTCCACT

CCTCTGCCGCGTCCCCGTGGCTGCAGGGAGCCGGCATGGGGCTTCTCCAG

TTGCTAGCTTTCAGTTTCTTAGCCCTGTGCAGAGCCCGAGTGCGCGCTCA

GGAACCCGAGTTCAGCTACGGCTGCGCAGAAGGCAGCTGCTATCCCGCCA

CGGGCGACCTTCTCATCGGCCGAGCACAGAAGCTTTCGGTGACCTCGACG

TGCGGGCTGCACAAGCCCGAACCCTACTGTATCGTCAGCCACTTGCAGGA

GGACAAAAAATGCTTCATATGCAATTCCCAAGATCCTTATCATGAGACCC

TGAATCCTGACAGCCATCTCATTGAAAATGTGGTCACTACATTTGCTCCA

AACCGCCTTAAGATTTGGTGGCAATCTGAAAATGGTGTGGAAAATGTAAC

TATCCAACTGGATTTGGAAGCAGAATTCCATTTTACTCATCTCATAATGA

CTTTCAAGACATTCCGTCCAGCTGCTATGCTGATAGAACGATCGTCCGAC

TTTGGGAAAACCTGGGGTGTGTATAGATACTTCGCCTATGACTGTGAGGC

CTCGTTTCCAGGCATTTCAACTGGCCCCATGAAAAAAGTCGATGACATAA

TTTGTGATTCTCGATATTCTGACATTGAACCCTCAACTGAAGGAGAGGTG

ATATTTCGTGCTTTAGATCCTGCTTTCAAAATAGAAGATCCTTATAGCCC

AAGGATACAGAATTTATTAAAAATTACCAACTTGAGAATCAAGTTTGTGA

AACTGCATACTTTGGGAGATAACCTTCTGGATTCCAGGATGGAAATCAGA

GAAAAGTATTATTATGCAGTTTATGATATGGTGGTTCGAGGAAATTGCTT

CTGCTATGGTCATGCCAGCGAATGTGCCCCTGTGGATGGATTCAATGAAG

AAGTGGAAGGAATGGTTCACGGACACTGCATGTGCAGGCATAACACCAAG

GGCTTAAACTGTGAACTCTGCATGGATTTCTACCATGATTTACCTTGGAG

ACCTGCTGAAGGCCGAAACAGCAACGCCTGTAAAAAATGTAACTGCAATG

AACATTCCATCTCTTGTCACTTTGACATGGCTGTTTACCTGGCCACGGGG

AACGTCAGCGGAGGCGTGTGTGATGACTGTCAGCACAACACCATGGGGCG

CAACTGTGAGCAGTGCAAGCCGTTTTACTACCAGCACCCAGAGAGGGACA

TCCGAGATCCTAATTTCTGTGAACGATGTACGTGTGACCCAGCTGGCTCT

CAAAATGAGGGAATTTGTGACAGCTATACTGATTTTTCTACTGGTCTCAT

TGCTGGCCAGTGTCGGTGTAAATTAAATGTGGAAGGAGAACATTGTGATG

TTTGCAAAGAAGGCTTCTATGATTTAAGCAGTGAAGATCCATTTGGTTGT

AAATCTTGTGCTTGCAATCCTCTGGGAACAATTCCTGGAGGGAATCCTTG

TGATTCCGAGACAGGTCACTGCTACTGCAAGCGTCTGGTGACAGGACAGC

ATTGTGACCAGTGCCTGCCAGAGCACTGGGGCTTAAGCAATGATTTGGAT

GGATGTCGACCATGTGACTGTGACCTTGGGGGAGCCTTAAACAACAGTTG

```
CTTTGCGGAGTCAGGCCAGTGCTCATGCCGGCCTCACATGATTGGACGTC
AGTGCAACGAAGTGGAACCTGGTTACTACTTTGCCACCCTGGATCACTAC
CTCTATGAAGCGGAGGAAGCCAACTTGGGGCCTGGGGTTAGCATAGTGGA
GCGGCAATATATCCAGGACCGGATTCCCTCCTGGACTGGAGCCGGCTTCG
TCCGAGTGCCTGAAGGGGCTTATTTGGAGTTTTTCATTGACAACATACCA
TATTCCATGGAGTACGACATCCTAATTCGCTACGAGCCACAGCTACCCGA
CCACTGGGAAAAGCTGTCATCACAGTGCAGCGACCTGGAAGGATTCCAA
CCAGCAGCCGATGTGGTAATACCATCCCCGATGATGACAACCAGGTGGTG
TCATTATCACCAGGCTCAAGATATGTCGTCCTTCCTCGGCCGGTGTGCTT
TGAGAAGGGAACAAACTACACGGTGAGGTTGGAGCTGCCTCAGTACACCT
CCTCTGATAGCGACGTGGAGAGCCCCTACACGCTGATCGATTCTCTTGTT
CTCATGCCATACTGTAAATCACTGGACATCTTCACCGTGGGAGGTTCAGG
AGATGGGGTGGTCACCAACAGTGCCTGGGAAACCTTTCAGAGATACCGAT
GTCTAGAGAACAGCAGAAGCGTTGTGAAAACACCGATGACAGATGTTTGC
AGAAACATCATCTTTAGCATTTCTGCCCTGTTACACCAGACAGGCCTGGC
TTGTGAATGCGACCCTCAGGGTTCGTTAAGTTCCGTGTGTGATCCCAACG
GAGGCCAGTGCCAGTGCCGGCCCAACGTGGTTGGAAGAACCTGCAACAGA
TGTGCACCTGGAACTTTTGGCTTTGGCCCCAGTGGATGCAAACCTTGTGA
GTGCCATCTGCAAGGATCTGTCAATGCCTTCGCAATCCCGTCACTGGCC
AGTGCCACTGTTTCCAGGGAGTGTATGCTCGGCAGTGTGATCGGTGCTTA
CCTGGGCACTGGGGCTTTCCAAGTTGCCAGCCCTGCCAGTGCAATGGCCA
CGCCGATGACTGCGACCCAGTGACTGGGGAGTGCTTGAACTGCCAGGACT
ACACCATGGGTCATAACTGTGAAAGGTGCTTGGCTGGTTACTATGGCGAC
CCCATCATTGGGTCAGGAGATCACTGCCGCCCTTGCCCTTGCCCAGATGG
TCCCGACAGTGGACGCCAGTTTGCCAGGAGCTGCTACCAAGATCCTGTTA
CTTTACAGCTTGCCTGTGTTTGTGATCCTGGATACATTGGTTCCAGATGT
GACGACTGTGCCTCAGGATACTTTGGCAATCCATCAGAAGTTGGGGGGTC
GTGTCAGCCTTGCCAGTGTCACAACAACATTGACACGACAGACCCAGAAG
CCTGTGACAAGGAGACTGGGAGGTGTCTCAAGTGCCTGTACCACACGGAA
GGGGAACACTGTCAGTTCTGCCGGTTTGGATACTATGGTGATGCCCTCCA
GCAGGACTGTCGAAAGTGTGTCTGTAATTACCTGGGCACCGTGCAAGAGC
ACTGTAACGGCTCTGACTGCCAGTGCGACAAAGCCACTGGTCAGTGCTTG
TGTCTTCCTAATGTGATCGGGCAGAACTGTGACCGCTGTGCGCCCAATAC
CTGGCAGCTGGCCAGTGGCACTGGCTGTGACCCATGCAACTGCAATGCTG
CTCATTCCTTCGGGCCATCTTGCAATGAGTTCACGGGGCAGTGCCAGTGC
ATGCCTGGGTTTGGAGGCCGCACCTGCAGCGAGTGCCAGGAACTCTTCTG
GGGAGACCCCGACGTGGAGTGCCGAGCCTGTGACTGTGACCCCAGGGGCA
TTGAGACGCCACAGTGTGACCAGTCCACGGGCCAGTGTGTCTGCGTTGAG
GGTGTTGAGGGTCCACGCTGTGACAAGTGCACGCGAGGGTACTCGGGGGT
CTTCCCTGACTGCACACCCTGCCACCAGTGCTTTGCTCTCTGGGATGTGA
TCATTGCCGAGCTGACCAACAGGACACACAGATTCCTGGAGAAAGCCAAG
```
```
GCCTTGAAGATCAGTGGTGTGATCGGGCCTTACCGTGAGACTGTGGACTC
GGTGGAGAGGAAAGTCAGCGAGATAAAAGACATCCTGGCGCAGAGCCCCG
CAGCAGAGCCACTGAAAAACATTGGGAATCTCTTTGAGGAAGCAGAGAAA
CTGATTAAAGATGTTACAGAAATGATGGCTCAAGTAGAAGTGAAATTATC
TGACACAACTTCCCAAAGCAACAGCACAGCCAAAGAACTGGATTCTCTAC
AGACAGAAGCCGAAAGCCTAGACAACACTGTGAAAGAACTTGCTGAACAA
CTGGAATTTATCAAAAACTCAGATATTCGGGGTGCCTTGGATAGCATTAC
CAAGTATTTCCAGATGTCTCTTGAGGCAGAGGAGAGGGTGAATGCCTCCA
CCACAGAACCCAACAGCACTGTGGAGCAGTCAGCCCTCATGAGAGACAGA
GTAGAAGACGTGATGATGGAGCGGAAATCCCAGTTCAAGGAAAAACAAGA
GGAGCAGGCTCGCCTCCTTGATGAACTGGCAGGCAAGCTACAAAGCCTAG
ACCTTTCAGCCGCTGCCGAAATGACCTGTGGAACACCCCAGGGGCCTCC
TGTTCCGAGACTGAATGTGGCGGGCCAAACTGCAGAACTGACGAAGGAGA
GAGGAAGTGTGGGGGCCTGGCTGTGGTGGTCTGGTTACTGTTGCACACA
ACGCCTGGCAGAAAGCCATGGACTTGGACCAAGATGTCCTGAGTGCCCTG
GCTGAAGTGGAACAGCTCTCCAAGATGGTCTCTGAAGCAAAACTGAGGGC
AGATGAGGCAAACAAAGTGCTGAAGACATTCTGTTGAAGACAAATGCTA
CCAAAGAAAAAATGGACAAGAGCAATGAGGAGCTGAGAAATCTAATCAAG
CAAATCAGAAACTTTTTGACCCAGGATAGTGCTGATTTGGACAGCATTGA
AGCAGTTGCTAATGAAGTATTGAAAATGGAGATGCCTAGCACCCCACAGC
AGTTACAGAACTTGACAGAAGATATACGTGAACGAGTTGAAAGCCTTTCT
CAAGTAGAGGTTATTCTTCAGCATAGTGCTGCTGACATTGCCAGAGCTGA
GATGTTGTTAGAAGAAGCTAAAAGAGCAAGCAAAAGTGCAACAGATGTTA
AAGTCACTGCAGATATGGTAAAGGAAGCTCTGGAAGAAGCAGAAAAGGCC
CAGGTCGCAGCAGAGAAGGCAATTAAACAAGCAGATGAAGACATTCAAGG
AACCCAGAACCTGTTAACTTCGATTGAGTCTGAAACAGCAGCTTCTGAGG
AAAACCTTGTTCAACGCGTCCCAGCGCATCAGCGAGTTAGAGAGGAATGTG
GAAGAACTTAAGCGGAAAGCTGCCCAAAACTCCGGGGAGGCAGAATATAT
TGAAAAGTAGTATATACTGTGAAGCAAAGTGCAGAAGATGTTAAGAAGA
CTTTAGATGGTGAACTTGATGAAAAGTATAAAAAAGTAGAAAATTTAATT
GCCAAAAAAACTGAAGAGTCAGCTGATGCCAGAAGGAAAGCCGAAATGCT
ACAAAATGAAGCAAAAACTCTTTTAGCTCAAGCAAATAGCAAGCTGCAAC
TGCTCAAAGATTTAGAAAGAAAATATGAAGACAATCAAAGATACTTAGAA
GATAAAGCTCAAGAATTAGCAAGACTGGAAGGAGAAGTCCGTTCACTCCT
AAAGGATATAAGCCAGAAAGTTGCTGTGTATAGCACATGCTTGTAACAGA
GGAGAATAAAAAATGGCTGAGGTGAACAAGGTAAAACAACTACATTTTAA
AAACTGACTTAATGCTCTTCAAAATAAAACATCACCTATTTAATGTTTTT
AATCACATTTTGTATGGAGTTAAATAAAGTACAGTGCTTTTGTATAAAAA
AAAAAAAAAAAAAAAA
```

Primers used:

```
Forward primer sequence:    ACAAGCCCGAACCCTACTGTA
Reverse primer sequence:    GACCACATTTTCAATGAGATGGC
```

Amplicon length: 125
Amplicon sequence:

ACAAGCCCGAACCCTACTGTATCGTCAGCCACTTGCAGGAGGACAAAAAA
TGCTTCATATGCAATTCCCAAGATCCTTATCATGAGACCCTGAATCCTGA
CAGCCATCTCATTGAAAATG

13. Insulin-Like Growth Factor Binding Protein 3 (IGFBP3)
Accession number: NM_000598.
Sequence:

AGATGCGAGCACTGCGGCTGGGCGCTGAGGATCAGCCGCTTCCTGCCTGG
ATTCCACAGCTTCGCGCCGTGTACTGTCGCCCCATCCCTGCGCGCCCAGC
CTGCCAAGCAGCGTGCCCCGGTTGCAGGCGTCATGCAGCGGGCGCGACCC
ACGCTCTGGGCCGCTGCGCTGACTCTGCTGGTGCTGCTCCGCGGGCCGCC
GGTGGCGCGGGCTGGCGCGAGCTCGGCGGGCTTGGGTCCCGTGGTGCGCT
GCGAGCCGTGCGACGCGCGTGCACTGGCCCAGTGCGCGCCTCCGCCCGCC
GTGTGCGCGGAGCTGGTGCGCGAGCCGGGCTGCGGCTGCTGCCTGACGTG
CGCACTGAGCGAGGGCCAGCCGTGCGGCATCTACACCGAGCGCTGTGGCT
CCGGCCTTCGCTGCCAGCCGTCGCCCGACGAGGCGCGACCGCTGCAGGCG
CTGCTGGACGGCCGCGGGCTCTGCGTCAACGCTAGTGCCGTCAGCCGCCT
GCGCGCCTACCTGCTGCCAGCGCCGCCAGCTCCAGGAAATGCTAGTGAGT
CGGAGGAAGACCGCAGCGCCGGCAGTGTGGAGAGCCCGTCCGTCTCCAGC
ACGCACCGGGTGTCTGATCCCAAGTTCCACCCCCTCCATTCAAAGATAAT
CATCATCAAGAAAGGGCATGCTAAAGACAGCCAGCGCTACAAAGTTGACT
ACGAGTCTCAGAGCACAGATACCCAGAACTTCTCCItCGAGTCCAAGCGG
GAGACAGAATATGGTCCCTGCCGTAGAGAAATGGAAGACACACTGAATCA
CCTGAAGTTCCTCAATGTGCTGAGTCCCAGGGGTGTACACATTCCCAACT
GTGACAAGAAGGGATTTTATAAGAAAAAGCAGTGTCGCCCTTCCAAAGGC
AGGAAGCGGGGCTTCTGCTGGTGTGTGGATAAGTATGGGCAGCCTCTCCC
AGGCTACACCACCAAGGGGAAGGAGGACGTGCACTGCTACAGCATGCAGA
GCAAGTAGACGCCTGCCGCAAGGTTAATGTGGAGCTCAAATATGCCTTAT
TTTGCACAAAAGACTGCCAAGGACATGACCAGCAGCTGGCTACAGCCTCG
ATTTATATTTCTGTTTGTGGTGAACTGATTTTTTTAAACCAAAGTTTAG
AAAGAGGTTTTTGAAATGCCTATGGTTTCTTTGAATGGTAAACTTGAGCA
TCTTTTCACTTTCCAGTAGTCAGCAAAGAGCAGTTTGAATTTTCTTGTCG
CTTCCTATCAAAATATTCAGAGACTCGAGCACAGCACCCAGACTTCATGC
GCCCGTGGAATGCTCACCACATGTTGGTCGAAGCGGCCGACCACTGACTT
TGTGACTTAGGCGGCTGTGTTGCCTATGTAGAGAACACGCTTCACCCCCA
CTCCCCGTACAGTGCGCACAGGCTTTATCGAGAATAGGAAAACCTTTAAA
CCCCGGTCATCCGGACATCCCAACGCATGCTCCTGGAGCTCACAGCCTTC
TGTGGTGTCATTTCTGAAACAAGGGCGTGGATCCCTCAACCAAGAAGAAT
GTTTATGTCTTCAAGTGACCTGTACTGCTTGGGGACTATTGGAGAAAATA
AGGTGGAGTCCTACTTGTTTAAAAAATATGTATCTAAGAATGTTCTAGGG
CACTCTGGGAACCTATAAAGGCAGGTATTTCGGGCCCTCCTCTTCAGGAA
TCTTCCTGAAGACATGGCCCAGTCGAAGGCCCAGGATGGCTTTTGCTGCG
GCCCCGTGGGGTAGGAGGGACAGAGAGACAGGGAGAGTCAGCCTCCACAT
TCAGAGGCATCACAAGTAATGGCACAATTCTTCGGATGACTGCAGAAAAT
AGTGTTTTGTAGTTCAACAACTCAAGACGAAGCTTATTTCTGAGGATAAG
CTCTTTAAAGGCAAAGCTTTATTTTCATCTCTCATCTTTTGTCCTCCTTA
GCACAATGTAAAAAAGAATAGTAATATCAGAACAGGAAGGAGGAATGGCT
TGCTGGGGAGCCCATCCAGGACACTGGGAGCACATAGAGATTCACCCATG
TTTGTTGAACTTAGAGTCATTCTCATGCTTTTCTTTATAATTCACACATA
TATGCAGAGAAGATATGTTCTTGTTAACATTGTATACAACATAGCCCCAA
ATATAGTAAGATCTATACTAGATAATCCTAGATGAAATGTTAGAGATGCT
ATATGATACAACTGTGGCCATGACTGAGGAAAGGAGCTCACGCCCAGAGA
CTGGGCTGCTCTCCCGGAGGCCAAACCCAAGAAGGTCTGGCAAAGTCAGG
CTCAGGGAGACTCTGCCCTGCTGCAGACCTCGGTGTGGACACACGCTGCA
TAGAGCTCTCCTTGAAAACAGAGGGGTCTCAAGACATTCTGCCTACCTAT
TAGCTTTTCTTTATTTTTTTAACTTTTTGGGGGAAAAGTATTTTTGAGA
AGTTTGTCTTGCAATGTATTTATAAATAGTAAATAAAGTTTTTACCATTA
AAAAATATCTTTCCCTTTGTTATTGACCATCTCTGGGCTTTGTATCACT
AATTATTTTATTTTATTATATAATAATTATTTTATTATAATAAAATCCTG
AAAGGGGAAAATAAAAAAAA

Primers used:

```
Forward primer sequence:    AGAGCACAGATACCCAGAACT
Reverse primer sequence:    TGAGGAACTTCAGGTGATTCAGT
```

Amplicon length: 105
Amplicon sequence:

AGAGCACAGATACCCAGAACTTCTCCTCCGAGTCCAAGCGGGAGACAGAA
TATGGTCCCTGCCGTAGAGAAATGGAAGACACACTGAATCACCTGAAGTT
CCTCA

14. Growth Arrest and DNA-Damage-Inducible, Alpha (GADD45A)
Accession number: NM_001924
Sequence:

CAGTGGCTGGTAGGCAGTGGCTGGGAGGCAGCGGCCCAATTAGTGTCGTG
CGGCCCGTGGCGAGGCGAGGTCCGGGGAGCGAGCGAGCAAGCAAGGCGGG
AGGGGTGGCCGGAGCTGCGGCGGCTGGCACAGGAGGAGGAGCCCGGGCGG
GCGAGGGGCGGCCGGAGAGCGCCAGGGCCTGAGCTGCCGGAGCGGCGCCT

```
GTGAGTGAGTGCAGAAAGCAGGCGCCCGCGCGCTAGCCGTGGCAGGAGCA
GCCCGCACGCCGCGCTCTCTCCCTGGGCGACCTGCAGTTTGCAATATGAC
TTTGGAGGAATTCTCGGCTGGAGAGCAGAAGACCGAAAGGATGGATAAGG
TGGGGGATGCCCTGGAGGAAGTGCTCAGCAAAGCCCTGAGTCAGCGCACG
ATCACTGTCGGGGTGTACGAAGCGGCCAAGCTGCTCAACGTCGACCCCGA
TAACGTGGTGTTGTGCCTGCTGGCGGCGGACGAGGACGACGACAGAGATG
TGGCTCTGCAGATCCACTTCACCCTGATCCAGGCGTTTTGCTGCGAGAAC
GACATCAACATCCTGCGCGTCAGCAACCCGGGCCGGCTGGCGGAGCTCCT
GCTCTTGGAGACCGACGCTGGCCCCGCGGCGAGCGAGGGCGCCGAGCAGC
CCCCGGACCTGCACTGCGTGCTGGTGACGAATCCACATTCATCTCAATGG
AAGGATCCTGCCTTAAGTCAACTTATTTGTTTTTGCCGGGAAAGTCGCTA
CATGGATCAATGGGTTCCAGTGATTAATCTCCCTGAACGGTGATGGCATC
TGAATGAAAATAACTGAACCAAATTGCACTGAAGTTTTTGAAATACCTTT
GTAGTTACTCAAGCAGTTACTCCCTACACTGATGCAAGGATTACAGAAAC
TGATGCCAAGGGGCTGAGTGAGTTCAACTACATGTTCTGGGGGCCCGGAG
ATAGATGACTTTGCAGATGGAAAGAGGTGAAAATGAAGAAGGAAGCTGTG
TTGAAACAGAAAATAAGTCAAAAGGAACAAAAATTACAAAGAACCATGC
AGGAAGGAAAACTATGTATTAATTTAGAATGGTTGAGTTACATTAAAATA
AACCAAATATGTTAAAGTTTAAGTGTGCAGCCATAGTTTGGGTATTTTTG
GTTTATATGCCCTCAAGTAAAAGAAAAGCCGAAAGGGTTAATCATATTTG
AAAACCATATTTTATTGTATTTTGATGAGATATTAAATTCTCAAAGTTTT
ATTATAAATTCTACTAAGTTATTTTATGACATGAAAAGTTATTTATGCTA
TAAATTTTTTGAAACACAATACCTACAATAAACTGGTATGAATAATTGCA
TCATT
```

Primers used:

```
Forward primer sequence:    GAGAGCAGAAGACCGAAAGGA
Reverse primer sequence:    CACAACACCACGTTATCGGG
```

Amplicon length: 145
Amplicon sequence:

```
GAGAGCAGAAGACCGAAAGGATGGATAAGGTGGGGGATGCCCTGGAGGAA
GTGCTCAGCAAAGCCCTGAGTCAGCGCACGATCACTGTCGGGGTGTACGA
AGCGGCCAAGCTGCTCAACGTCGACCCCGATAACGTGGTGTTGTG
```

15. Follistatin-Like 1 (FSTL1)
Accession number: BX647421
Sequence:

```
ATTTCCTCCGAGGCTGGCGATCGGCGGAGCTCCCACCTCCGCTTACAGCT
CGCTGCCGCCGTCCTGCCCCGCGCCCCAGGAGACCTGGACCAGACCACG
ATGTGGAAACGCTGGCTCGCGCTCGCGCTCGCGCTGGTGGCGGTCGCCTG
GGTCCGCGCCGAGGAAGAGCTAAGGAGCAAATCCAAGATCTGTGCCAATG
TGTTTTGTGGAGCCGGCCGGGAATGTGCAGTCACAGAGAAAGGGGAACCC
ACCTGTCTCTGCATTGAGCAATGCAAACCTCACAAGAGGCCTGTGTGTGG
CAGTAATGGCAAGACCTACCTCAACCACTGTGAACTGCATCGAGATGCCT
GCCTCACTGGATCCAAAATCCAGGTTGATTACGATGGACACTGCAAAGAG
AAGAAATCCGTAAGTCCATCTGCCAGCCCAGTTGTTTGCTATCAGTCCAA
CCGTGATGAGCTCCGACGTCGCATCATCCAGTGGCTGGAAGCTGAGATCA
TTCCAGATGGCTGGTTCTCTAAAGGCAGCAACTACAGTGAAATCCTAGAC
AAGTATTTTAAGAACTTTGATAATGGTGATTCTCGCCTGGACTCCAGTGA
ATTCCTGAAGTTTGTGGAACAGAATGAAACTGCCATCAATATTACAACGT
ATCCAGACCAGGAGAACAACGAGTTGCTTAGGGGACTCTGTGTTGATGCT
CTCATTGAACTGTCTGATGAAATGCTGATTGGAAACTCAGCTTCCAAGA
GTTTCTCAAGTGCCTCAACCCATCTTTCAACCCTCCTGAGAAGAAGTGTG
CCCTGGAGGATGAAACGTATGCAGATGGAGCTGAGACCGAGGTGGACTGT
AACCGCTGTGTCTGTGCCTGTGGAAATTGGGTCTGTACAGCCATGACCTG
TGACGGAAAGAATCAGAAGGGGGCCCAGACCCAGACAGAGGAGGAGATGA
CCAGATATGTCCAGGAGCTCCAAAAGCATCAGGAAACAGCTGAAAAGACC
AAGAGAGTGAGCACCAAAGAGATCTAATGAGGAGGCACAGACCAGTGTCT
GGATCCCAGCATCTTCTCCACTTCAGCGCTGAGTTCAGTATACACAAGTG
TCTGCTACAGTCGCCAAATCACCAGTATTTGCTTATATAGCAATGAGTTT
TATTTTGTTTATTTGTTTTGCAATAAAGGATATGAAGGTGGCTGGCTAGG
AAGGGAAGGGCCACAGCCTTCATTTCTAGGAGTGCTTTAAGAGAAACTGT
AAATGGTGCTCTGGGGCTGGAGGCTAGTAAGGAAACTGCATCACGATTGA
AAGAGGAACAGACCCAAATCTGAACCTCTTTTGAGTTTACTGCATCTGTC
AGCAGGCTGCAGGGAGTGCACACGATGCCAGAGAGAACTTAGCAGGGTGT
CCCCGGAGGAGAGGTTTGGGAAGCTCCACGGAGAGGAACGCTCTCTGCTT
CCAGCCTCTTTCCATTGCCGTCAGCATGACAGACCTCCAGCATCCACGCA
TCTCTTGGTCCCAATAACTGCCTCTAGATACATAGCCATACTGCTAGTTA
ACCCAGTGTCCCTCAGACTTGGATGGAGTTTCTGGGAGGGTACACCCAAA
TGATGCAGATACTTGTATACTTTGAGCCCCTTAGCGACCTAACCAAATTT
TAAAAATACTTTTTACCAAAGGTGCTATTTCTCTGTAAAACACTTTTTTT
TGGCAGGTTGACTTTATTCTTCAATTATTATCATTATATTATTGTTTTTT
AATATTTTATTTTCTTGACTAGGTATTAAGCTTTTGTAATTATTTTTCAG
TAGTCCCACCACTTCATAGGTGGAAGGAGTTTGGGGTTCTTCCTGGTGCA
GGGGCTGAAATAACCCAGATGCCCCACCCTGCCACATACTAGATGCAGC
CCATAGTTGGCCCCCCTAGCTTCCAGCAGTCCACTATCTGCCAGAGGAGC
AAGGGTGCCTTAGACCGAAGCCAGGGGAAGAAGCATCTTCATAAAAAACT
TTCAAGATCCAAACATTAATTTGTTTTTATTTATTCTGAGAAGTTGAGGC
AAATCAGTATTCCCAAGGATGGCGACAAGGGCAGCCAAGCAGGGCTTAGG
ATATCCCAGCCTACCAATATGCTCATTCGACTAACTAGGAGGGTGAGTTG
GCCCTGTCTCTTCTTTTTTTCTGGACCTCAGTTTCCTCAGTGAGCTGGTAA
```

-continued
```
GAATGCACTAACCTTTTGATTTGATAAGTTATAAATTCTGTGGTTCTGAT
CATTGGTCCAGAGGGGAGATAGGTTCCTGTGATTTTTCCTTCTTCTCTAT
AGAATAAATGAAATCTTGTTACTAGAACAAGAAATGTCAGATGGCCAAAA
ACAAGATGACCAGATTTGATCTCAGCCTGATGACCCTACAGGTCGTGCTA
TGATATGGAGTCCTCATGGGTAAAGCAGGAAGAGAGTGGGAAAGAGAACC
ACCCCACTCTGTCTTCATATTTGCATTTCATGTTTAACCTCCGGCTGGAA
ATAGAAAGCATTCCCTTAGAGATGAGGATAAAAGAAAGTTTCAGATTCAA
CAGGGGGAAGAAAATGGAGATTTAATCCTAAAACTGTGACTTGGGGAGGT
CAGTCATTTACAGTTAGTCCTGTGTCTTTCGACTTCTGTGATTATTAACC
CCACTCACTACCCTGTTTCAGATGCATTTGGAATACCAAAGATTAAATCC
TTGACATAAGATCTCATTTGCAGAAAGCAGATTAAAGACCATCAGAAGGA
AATTATTTAGGTTGTAATGCACAGGCAACTGTGAGAAACTGTTGTGCCAA
AAATAGAATTCCTTCTAGTTTTTCTTGTTCTCATTTGAAAGGAGAAAATT
CCACTTTGTTTAGCATTTCAAGCTTTTATGTATCCATCCCATCTAAAAAC
TCTTCAAACTCCACTTGTTCAGTCTGAAATGCAGCTCCCTGTCCAAGTGC
CTTGGAGAACTCACAGCAGCACGCCTTAATCAAAGGTTTTACCAGCCCTT
GGACACTATGGGAGGAGGGCAAGAGTACACCAATTTGTTAAAAGCAAGAA
ACCACAGTGTCTCTTCACTAGTCATTTAGAACATGGTTATCATCCAAGAC
TACTCTACCCTGCAACATTGAACTCCCAAGAGCAAATCCACATTCCTCTT
GAGTTCTGCAGCTTCTGTGTAAATAGGGCAGCTGTCGTCTATGCCGTAGA
ATCACATGATCTGAGGACCATTCATGGAAGCTGCTAAATAGCCTAGTCTG
GGGAGTCTTCCATAAAGTTTTGCATGGAGCAAACAAACAGGATTAAACTA
GGTTTGGTTCCTTCAGCCCTCTAAAAGCATAGGGCTTAGCCTGCAGGCTT
CCTTGGGCTTTCTCTGTGTGTAGTTTTGTAAACACTATAGCATCTGTT
AAGATCCAGTGTCCATGGAAACATTCCCACATGCCGTGACTCTGGACTAT
ATCAGTTTTTGGAAAGCAGGGTTCCTCTGCCTGCTAACAAGCCCACGTGG
ACCAGTCTGAATGTCTTTCCTTTACACCTATGTTTTTAAGTAGTCAAACT
TCAAGAAACAATCTAAACAAGTTTCTGTTGCATATGTGTTTGTGAACTTG
TATTTGTATTTAGTAGGCTTCTATATTGCATTTAACTTGTTTTTGTAACT
CCTGATTCTTCCTTTTCGGATACTATTGATGAATAAAGAAATTAAAGTGA
AAAAAAAAAAAAAAAAAAAAGAAAAAAAAAAAAAAAAAA
```
Primers used:

```
Forward primer sequence:   CAACCACTGTGAACTGCATCG
Reverse primer sequence:   CCTTTAGAGAACCAGCCATCTG
```
Amplicon length: 204
Amplicon sequence:

```
CAACCACTGTGAACTGCATCGAGATGCCTGCCTCACTGGATCCAAAATCC
AGGTTGATTACGATGGACACTGCAAAGAGAAGAAATCCGTAAGTCCATCT
GCCAGCCCAGTTGTTTGCTATCAGTCCAACCGTGATGAGCTCCGACGTCG
CATCATCCAGTGGCTGGAAGCTGAGATCATTCCAGATGGCTGGTTCTCTA
AAGG
```

16. Ras Homolog Gene Family, Member C(RHOC)
Accession number: AK094474
Sequence:

```
GGAGCCTGTAGCCTTTATTCATGCCCCCCTGACCAAATGCAGTGAGAGAC
AAGGCCCCTGCCGAAAACAACTCCAGGGGCCTGGGACTCTGGGTCCCCTA
CTGCAGACACTTTCCTGTGAGCCAGAAGTGTATAAAGTGCTGGTGTGTGA
CCATCCTTTGGGGAAGGTCAAAGGGGGCAAGATCCCCAGGGGCCCTGAGG
AAGGGCAGGGCATAGGCGTGGCTCCCAGAGCGCTGGGAGGGAGGGCCCGT
GCCACCACCTCGGGGCTAGAAAACAATGCAGTCCTGGGCAGGAGGGAACT
GAAAATGGGAGCCTTCAGCATGGAGCCCTCAGGAGGCTGGGGTTGTAGGG
GGATAATTTCTGTACCCCTGTGAAGGGAGGGGGCATGTAGGAAAGGCCTT
GGGGATCTCAGAGAATGGGACAGCCCCTCCGACGCTTGTTCTTGCGGACC
TGGAGGCCAGCCCGAGTGGCCATCTCAAACACCTCCCGCACTCCCTCCTT
GGTCTTGGCTGAGCACTCAAGGTAGCCAAAGGCACTGATCCGGTTCGCCA
TGTCCCGGCCTTCCTCAGACCGAACGGGCTCCTGCTTCATCTTGGCCAGC
TCTCTCCTGGTGTGCTCGTCTTGCCTCAGGTCCTTCTTATTCCCCACCAG
GATGATGGGCACGTTGGGGCAGAAGTGCTTCACCTCTGGGGTCCACTTCT
CAGGAATGTTTTCCAGGCTGTCAGGGCTGTCGATGGAGAAGCACATGAGG
ATGACATCAGTGTCCGGGTAGGAGAGAGGCCGCAGTCGATCATAGTCTTC
CTGCCCTGCTGTGTCCCACAGAGCCAGCTCCACCTGCTTGCCGTCCACCT
CAATGTCCGCAATATAGTTCTCAAAGACAGTAGGGACGTAGACCTCCGGA
AACTGATCCTTGCTGAAGACGATGAGGAGGCAGGTCTTCCCACAGGCACC
ATCCCCAACGATCACCAGCTTCTTTCGGATTGCAGCCATGGTGGGCTCC
AGCCGGCTGAAGTTCCCAGGCTGCAGGAAGAGAGGGCGGGCTCTGGAGCT
GAGATGAAGTCAAGGCTGTTGGGAAGGGGGAGGGGGCTAGAGTCTGGGCT
GGGAGGAGCCCCAAAAGAAGAGACAAATGAGGGCCAGTCCCAGCACCAAC
CAGGCAGGGAGCAGTTAAGAAAGCGACGGTAACCTGATCTCAGCCTCAAA
CCTAGCTTTTTCTCTCAGTCCCACATCCTGTCAAACTGGGCTGACTGAAC
GCCTCTACTCCCCACACCCCACCACCACCTCACACTGCCCTTTAGGAAGC
GAATACTCCAGCCCCAGGCCTCTTCCCTTCAACATAGATCCTGAGTGGCC
CTTCCCTTGCCTCCAGACACATTCACAAAACTGTTGGTTTTGTGGACATG
AGTCAGAGAATTTACAGGAGTTCAAAGTACACAGCCACACTCTTCCCACC
ACAAAACGGACTCTCTCTGATTCCCCAGAAGACAAGCAAGAAGGCATTCA
CCCTGTCGGCAGATCGCCTCCAGAAATGGAAACCATCCTCCAAAAAGAGG
GTTCCTTGGGAATTCTATCCCGGTGACTGACGCTGGGATTTCTTCCAACT
CCTCCACCCACTCCATTAGTTCACCTTGCCCTGTTTTGTAAAGATGGGCT
GGGGTAGCCCCAACCTGGGGTGGGCAGTGTTGATGGAGGGCAATCACTAC
TGGGGTGAAAGCCAGTCACTTAGGCATGAGTATGCCACTGCTGTCCCCCC
AGCAGGGTAATTCAGACGGCACCAGAGTGGTGGGAGGCAGAGGACAGAAA
```

-continued

```
CCCGGGGTTGAGGCATGCGTTAAGGGACCTGGAGCCTCCAGCCCAATTAG

AAGACTTTCCCTCCAGGCTATGATTGGGCCAGAACAGCAGGCAGCCCAGG

CCAGGACACTAGGCCCAAGGCCAAGATGGCATGGACAACTCCCTGTGAGA

GGCAGCCCCAGAGGGACTGTCCCACTGACCCCTTAAGAGGGGCAACTGAG

CCCCACACAGGGCCTGGAATGGAGCCTGGAACTTCTGGGGCCTTCCCCAA

GACAAGACAGTGTGGATACATCAGACCTCTCTCCAATCGCTCTCTTGAAT

TCCCAGATGATCCAGAGCGGCCGGTTGACTTTGCCGGCCCACCCTACACC

TTCCGCTCCGCCGCCTCCAGCTGCGCGGCCGGTGCCGGAGGCTCAGACT
```

Primers used:

```
Forward primer sequence:   CCTGCCTCCTCATCGTCTTC
Reverse primer sequence:   AGCACATGAGGATGACATCAGTG
```

Amplicon length: 195
Amplicon sequence:

```
CCTGCCTCCTCATCGTCTTCAGCAAGGATCAGTTTCCGGAGGTCTACG

TCCCTACTGTCTTTGAGAACTATATTGCGGACATTGAGGTGGACGGCA

AGCAGGTGGAGCTGGCTCTGTGGGACACAGCAGGGCAGGAAGACTATG

ATCGACTGCGGCCTCTCTCCTACCCGGACACTGATGTCATCCTCATGT

GCT
```

17. AE Binding Protein 1 (AEBP1)
Accession number: NM_001129
Sequence:

```
CGGCTATCCGCGCGGGAGTGCGCCACGCGGGGCCGGAGCGCCTATTAG

CCGCCAGGACCTCGGAGCGCCCCGACCACCCCTGAGCCCCTCTGGCTT

CGGAGCCCCCAGCACCCCTTCCCGGGTCCCCTCGCCCACCCTAATCC

ACTCTCCCTCCCTTTCCCGGATTCCCTCGCTCACCCCATCCTCTCTCC

CGCCCCTTCCTGGATTCCCTCACCCGTCTCGATCCCCTCTCCGCCCTT

TCCCAGAGACCCAGAGCCCCTGACCCCCCGCGCCCTCCCCGGAGCCCC

CCGCGCGTGCCGCGGCCATGGCGGCCGTGCGCGGGGCGCCCCTGCTCA

GCTGCCTCCTGGCGTTGCTGGCCCTGTGCCCTGGAGGGCGCCCGCAGA

CGGTGCTGACCGACGACGAGATCGAGGAGTTCCTCGAGGGCTTCCTGT

CAGAGCTAGAACCTGAGCCCCGGGAGGACGACGTGGAGGCCCCGCCGC

CTCCCGAGCCCACCCCGCGGGTCCGAAAAGCCCAGGCGGGGGCAAGC

CAGGGAAGCGGCCAGGGACGGCCGCAGAAGTGCCTCCGGAAAAGACCA

AAGACAAAGGGAAGAAAGGCAAGAAAGACAAAGGCCCCAAGGTGCCCA

AGGAGTCCTTGGAGGGGTCCCCCAGGCCGCCCAAGAAGGGGAAGGAGA

AGCCACCCAAGGCCACCAAGAAGCCCAAGGAGAAGCCACCTAAGGCCA

CCAAGAAGCCCAAGGAGAAGCCACCCAAGGCCACCAAGAAGCCCAAAG

AGAAGCCACCCAAGGCCACCAAGAAGCCCCCGTCAGGGAAGAGGCCCC

CCATTCTGGCTCCCTCAGAAACCCTGGAGTGGCCACTGCCCCCACCCC

CCAGCCCTGGCCCCGAGGAGCTACCCCAGGAGGGGAGGGGCGCCCCTCT

CAAATAACTGGCAGAATCCAGGAGAGGAGACCCATGTGGAGGCACGGG

AGCACCAGCCTGAGCCGGAGGAGGAGACCGAGCAACCCACACTGGACT

ACAATGACCAGATCGAGAGGGAGGACTATGAGGACTTTGAGTACATTC

GGCGCCAGAAGCAACCCAGGCCACCCCCAAGCAGAAGGAGGAGGCCCG

AGCGGGTCTGGCCAGAGCCCCTGAGGAGAAGGCCCCGGCCCCAGCCC

CGGAGGAGAGGATTGAGCCTCCTGTGAAGCCTCTGCTGCCCCCGCTGC

CCCCTGACTATGGTGATGGTTACGTGATCCCCAACTACGATGACATGG

ACTATTACTTTGGGCCTCCTCCGCCCCAGAAGCCCGATGCTGAGCGCC

AGACGGACGAAGAAGGAGGAGCTGAAGAAACCCAAAAAGGAGGACA

GCAGCCCCAAGGAGGAGACCGACAAGTGGGCAGTGGAGAAGGGCAAGG

ACCACAAAGAGCCCCGAAAGGGCGAGGAGTTGGAGGAGGAGTGGACGC

CTACGGAGAAAGTCAAGTGTCCCCCCATTGGGATGGAGTCACACCGTA

TTGAGGACAACCAGATCCGAGCCTCCTCCATGCTGCGCCACGGCCTGG

GGGCACAGCGCGGCCGGCTCAACATGCAGACCGGTGCCACTGAGGACG

ACTACTATGATGGTGCGTGGTGTGCCGAGGACGATGCCAGGACCCAGT

GGATAGAGGTGGACACCAGGAGGACTACCCGGTTCACAGGCGTCATCA

CCCAGGGCAGAGACTCCAGCATCCATGACGATTTTGTGACCACCTTCT

TCGTGGGCTTCAGCAATGACAGCCAGACATGGGTGATGTACACCAACG

GCTATGAGGAAATGACCTTTCATGGGAACGTGGACAAGGACACACCCG

TGCTGAGTGAGCTCCCAGAGCCGGTGGTGGCTCGTTTCATCCGCATCT

ACCCCACTCACCTGGAATGGCAGCCTGTGCATGCGCCTGGAGGTGCTGG

GGTGCTCTGTGGCCCCTGTCTACAGCTACTACGCACAGAATGAGGTGG

TGGCCACCGATGACCTGGATTTCCGGCACCACAGCTACAAGGACATGC

GCCAGCTCATGAAGGTGGTGAACGAGGAGTGCCCCACCATCACCCGCA

CTTACAGCCTGGGCAAGAGCTCACGAGGCCTCAAGATCTATGCCATGG

AGATCTCAGACAACCCTGGGGAGCATGAACTGGGGGAGCCCGAGTTCC

GCTACACTGCTGGGATCCATGGCAACGAGGTGCTGGGCCGAGAGCTGT

TGCTGCTGCTCATGCAGTACCTGTGCCGAGAGTACCGCGATGGGAACC

CACGTGTGCGCAGCCTGGTGCAGGACACACGCATCCACCTGGTGCCCT

CACTGAACCCTGATGGCTACGAGGTGGCAGCGCAGATGGGCTCAGAGT

TTGGGAACTGGGCGCTGGGACTGTGGACTGAGGAGGGCTTTGACATCT

TTGAAGATTTCCCGGATCTCAACTCTGTGCTCTGGGGAGCTGAGGAGA

GGAAATGGGTCCCCTACCGGGTCCCCAACAATAACTTGCCCATCCCTG

AACGCTACCTTTCGCCAGATGCCACGGTATCCACGGAGGTCCGGGCCA

TCATTGCCTGGATGGAGAAGAACCCCTTCGTGCTGGGAGCAAATCTGA

ACGGCGGCGAGCGGCTAGTATCCTACCCCTACGATATGGCCCGCACGC

CTACCCAGGAGCAGCTGCTGGCCGCAGCCATGGCAGCAGCCCGGGGGG

AGGATGAGGACGAGGTCTCCGAGGCCCAGGAGACTCCAGACCACGCCA

TCTTCCGGTGGCTTGCCATCTCCTTCGCCTCCGCACACCTCACCTTGA
```

```
CCGAGCCCTACCGCGGAGGCTGCCAAGCCCAGGACTACACCGGCGGCA

TGGGCATCGTCAACGGGGCCAAGTGGAACCCCCGGACCGGGACTATCA

ATGACTTCAGTTACCTGCATACCAACTGCCTGGAGCTCTCCTTCTACC

TGGGCTGTGACAAGTTCCCTCATGAGAGTGAGCTGCCCCGCGAGTGGG

AGAACAACAAGGAGGCGCTGCTCACCTTCATGGAGCAGGTGCACCGCG

GCATTAAGGGGTGGTGACGGACGAGCAAGGCATCCCCATTGCCAACG

CCACCATCTCTGTGAGTGGCATTAATCACGGCGTGAAGACAGCCAGTG

GTGGTGATTACTGGCGAATCTTGAACCCGGGTGAGTACCGCGTGACAG

CCCACGCGGAGGGCTACACCCCGAGCGCCAAGACCTGCAATGTTGACT

ATGACATCGGGGCCACTCAGTGCAACTTCATCCTGGCTCGCTCCAACT

GGAAGCGCATCCGGGAGATCATGGCCATGAACGGGAACCGGCCTATCC

CACACATAGACCCATCGCGCCCTATGACCCCCAACAGCGACGCCTGC

AGCAGCGACGCCTACAACACCGCCTGCGGCTTCGGGCACAGATGCGGC

TGCGGCGCCTCAACGCCACCACCACCCTAGGCCCCCACACTGTGCCTC

CCACGCTGCCCCCTGCCCCTGCCACCACCCTGAGCACTACCATAGAGC

CCTGGGCCTCATACCGCCAACCACCGCTGGCTGGGAGGAGTCGGAGA

CTGAGACCTACACAGAGGTGGTGACAGAGTTTGGGACCGAGGTGGAGC

CCGAGTTTGGGACCAAGGTGGAGCCCGAGTTTGAGACCCAGTTGGAGC

CTGAGTTTGAGACCCAGCTGGAACCCGAGTTTGAGGAAGAGGAGGAGG

AGGAGAAAGAGGAGGAGATAGCCACTGGCCAGGCATTCCCCTTCACAA

CAGTAGAGACCTACACAGTGAACTTTGGGGACTTCTGAGATCAGCGTC

CTACCAAGACCCCAGCCCAACTCAAGCTACAGCAGCAGCACTTCCCAA

GCCTGCTGACCACAGTCACATCACCCATCAGCACATGGAAGGCCCCTG

GTATGGACACTGAAAGGAAGGGCTGGTCCTGCCCCTTTGAGGGGTGC

AAACATGACTGGGACCTAAGAGCCAGAGGCTGTGTAGAGGCTCCTGCT

CCACCTGCCAGTCTCGTAAGAGATGGGGTTGCTGCAGTGTTGGAGTAG

GGGCAGAGGGAGGGAGCCAAGGTCACTCCAATAAAACAAGCTCATGGC

AAAAAAAAAAAAAAAAAAAAAAAAAAAAAAAAAAAAAAAAAAAAA
```
Primers used:

```
        Forward primer sequence:
        AAAGGGCGAGGAGTTGGAG

Reverse primer sequence:
        GAGGCTCGGATCTGGTTGT Amplicon length: 105
```
Amplicon sequence:

```
    AAAGGGC GAGGAGTTGG AGGAGGAGTG GACGCCTACG

GAGAAAGTCA AGTGTCCCCC CATTGGGATG GAGTCACACC

GTATTGAGGA CAACCAGATC CGAGCCTC
```
18. Beta 2 Microglobulin (B2M)
Accession number: NM_004048
Sequence:

```
AATATAAGTGGAGGCGTCGCGCTGGCGGGCATTCCTGAAGCTGACAGC

ATTCGGGCCGAGATGTCTCGCTCCGTGGCCTTAGCTGTGCTCGCGCTA
```

```
CTCTCTCTTTCTGGCCTGGAGGCTATCCAGCGTACTCCAAAGATTCAG

GTTTACTCACGTCATCCAGCAGAGAATGGAAAGTCAAATTTCCTGAAT

TGCTATGTGTCTGGGTTTCATCCATCCGACATTGAAGTTGACTTACTG

AAGAATGGAGAGAGAATTGAAAAAGTGGAGCATTCAGACTTGTCTTTC

AGCAAGGACTGGTCTTTCTATCTCTTGTACTACACTGAATTCACCCCC

ACTGAAAAAGATGAGTATGCCTGCCGTGTGAACCATGTGACTTTGTCA

CAGCCCAAGATAGTTAAGTGGGATCGAGACATGTAAGCAGCATCATGG

AGGTTTGAAGATGCCGCATTTGGATTGGATGAATTCCAAATTCTGCTT

GCTTGCTTTTTAATATTGATATGCTTATACACTTACACTTTATGCACA

AAATGTAGGGTTATAATAATGTTAACATGGACATGATCTTCTTTATAA

TTCTACTTTGAGTGCTGTCTCCATGTTTGATGTATCTGAGCAGGTTGC

TCCACAGGTAGCTCTAGGAGGGCTGGCAACTTAGAGGTGGGGAGCAGA

GAATTCTCTTATCCAACATCAACATCTTGGTCAGATTTGAACTCTTCA

ATCTCTTGCACTCAAAGCTTGTTAAGATAGTTAAGCGTGCATAAGTTA

ACTTCCAATTTACATACTCTGCTTAGAATTTGGGGGAAAATTTAGAAA

TATAATTGACAGGATTATTGGAAATTTGTTATAATGAATGAAACATTT

TGTCATATAAGATTCATATTTACTTCTTATACATTTGATAAAGTAAGG

CATGGTTGTGGTTAATCTGGTTTATTTTTGTTCCACAAGTTAAATAAA

TCATAAAACTTGATGTGTTATCTCTTA
```
Primers used:

```
        Forward primer sequence:
        AGGCTATCCAGCGTACTCCAA

Reverse primer sequence:
        AATGCGGCATCTTCAAACC
```
Amplicon length: 337
Amplicon sequence:

```
AGGCTATCCAGCGTACTCCAAAGATTCAGGTTTACTCACGTCATCCAG

CAGAGAATGGAAAGTCAAATTTCCTGAATTGCTATGTGTCTGGGTTTC

ATCCATCCGACATTGAAGTTGACTTACTGAAGAATGGAGAGAGAATTG

AAAAAGTGGAGCATTCAGACTTGTCTTTCAGCAAGGACTGGTCTTTCT

ATCTCTTGTACTACACTGAATTCACCCCCACTGAAAAAGATGAGTATG

CCTGCCGTGTGAACCATGTGACTTTGTCACAGCCCAAGATAGTTAAGT

GGGATCGAGACATGTAAGCAGCATCATGGAGGTTTGAAGATGCCGCA

TT
```
19. Superoxide Dismutase 2, Mitochondrial (SOD2)
Accession number: NM_001024465.
Sequence:

```
GCGGTGCCCTTGCGGCGCAGCTGGGGTCGCGGCCCTGCTCCCCGCGCT

TTCTTAAGGCCCGCGGGCGGCGCAGGAGCGGCACTCGTGGCTGTGGTG

GCTTCGGCAGCGGCTTCAGCAGATCGGCGGCATCAGCGGTAGCACCAG
```

-continued

```
CACTAGCAGCATGTTGAGCCGGGCAGTGTGCGGCACCAGCAGGCAGCT
GGCTCCGGTTTTGGGGTATCTGGGCTCCAGGCAGAAGCACAGCCTCCC
CGACCTGCCCTACGACTACGGCGCCCTGGAACCTCACATCAACGCGCA
GATCATGCAGCTGCACCACAGCAAGCACCACGCGGCCTACGTGAACAA
CCTGAACGTCACCGAGGAGAAGTACCAGGAGGCGTTGGCCAAGGGAGA
TGTTACAGCCCAGATAGCTCTTCAGCCTGCACTGAAGTTCAATGGTGG
TGGTCATATCAATCATAGCATTTTCTGGACAAACCTCAGCCCTAACGG
TGGTGGAGAACCCAAAGGGGAGTTGCTGGAAGCCATCAAACGTGACTT
TGGTTCCTTTGACAAGTTTAAGGAGAAGCTGACGGCTGCATCTGTTGG
TGTCCAAGGCTCAGGTTGGGGTTGGCTTGGTTTCAATAAGGAACGGGG
ACACTTACAAATTGCTGCTTGTCCAAATCAGGATCCACTGCAAGGAAC
AACAGGCCTTATTCCACTGCTGGGGATTGATGTGTGGGAGCACGCTTA
CTACCTTCAGTATAAAAATGTCAGGCCTGATTATCTAAAAGCTATTTG
GAATGTAATCAACTGGGAGAATGTAACTGAAAGATACATGGCTTGCAA
AAAGTAAACCACGATCGTTATGCTGATCATACCCTAATGATCCCAGCA
AGATAATGTCCTGTCTTCTAAGATGTGCATCAAGCCTGGTACATACTG
AAAACCCTATAAGGTCCTGGATAATTTTTGTTTGATTATTCATTGAAG
AAACATTTATTTTCCAATTGTGTGAAGTTTTTGACTGTTAATAAAAGA
ATCTGTCAACCATCAAAAAAAAAAAAA
```

Primers used:

```
Forward primer sequence:
AACCTCAGCCCTAACGGTG

Reverse primer sequence:
AGCAGCAATTTGTAAGTGTCCC
```

Amplicon length: 180
Amplicon sequence:

```
AACCTCAGCCCTAACGGTGGTGGAGAACCCAAAGGGGAGTTGCTGGAA
GCCATCAAACGTGACTTTGGTTCCTTTGACAAGTTTAAGGAGAAGCTG
ACGGCTGCATCTGTTGGTGTCCAAGGCTCAGGTTGGGGTTGGCTTGGT
TTCAATAAGGAACGGGGACACTTACAAATTGCTCT
```

20. Nicotinamide Phosphoribosyltransferase (PBEF1)
Accession number: NM_005746
Sequence:

```
GCTGCCGCGCCCCGCCCTTTCTCGGCCCCGGAGGGTGACGGGGTGAA
GGCGGGGGAACCGAGGTGGGGAGTCCGCCAGAGCTCCCAGACTGCGAG
CACGCGAGCCGCCGCAGCCGTCACCCGCGCCGCGTCACGGCTCCCGGG
CCCGCCCTCCTCTGACCCCTCCCCTCTCTCCGTTTCCCCCTCTCCCCC
TCCTCCGCCGACCGAGCAGTGACTTAAGCAACGGAGCGCGGTGAAGCT
CATTTTTCTCCTTCCTCGCAGCCGCGCCAGGGAGCTCGCGGCGCGCGG
CCCCTGTCCTCCGGCCCGAGATGAATCCTGCGGCAGAAGCCGAGTTCA
ACATCCTCCTGGCCACCGACTCCTACAAGGTTACTCACTATAAACAAT
ATCCACCCAACACAAGCAAAGTTTATTCCTACTTTGAATGCCGTGAAA
AGAAGACAGAAAACTCCAAATTAAGGAAGGTGAAATATGAGGAAACAG
TATTTTATGGGTTGCAGTACATTCTTAATAAGTACTTAAAAGGTAAAG
TAGTAACCAAAGAGAAAATCCAGGAAGCCAAAGATGTCTACAAAGAAC
ATTTCCAAGATGATGTCTTTAATGAAAAGGGATGGAACTACATTCTTG
AGAAGTATGATGGGCATCTTCCAATAGAAATAAAAGCTGTTCCTGAGG
GCTTTGTCATTCCCAGAGGAAATGTTCTCTTCACGGTGGAAAACACAG
ATCCAGAGTGTTACTGGCTTACAAATTGGATTGAGACTATTCTTGTTC
AGTCCTGGTATCCAATCACAGTGGCCACAAATTCTAGAGAGCAGAAGA
AAATATTGGCCAAATATTTGTTAGAAACTTCTGGTAACTTAGATGGTC
TGGAATACAAGTTACATGATTTTGGCTACAGAGGAGTCTCTTCCCAAG
AGACTGCTGGCATAGGAGCATCTGCTCACTTGGTTAACTTCAAAGGAA
CAGATACAGTAGCAGGACTTGCTCTAATTAAAAAATATTATGGAACGA
AAGATCCTGTTCCAGGCTATTCTGTTCCAGCAGCAGAACACAGTACCA
TAACAGCTTGGGGAAAGACCATGAAAAAGATGCTTTTGAACATATTG
TAACACAGTTTTCATCAGTGCCTGTATCTGTGGTCAGCGATAGCTATG
ACATTTATAATGCGTGTGAGAAAATATGGGGTGAAGATCTAAGACATT
TAATAGTATCAAGAAGTACACAGGCACCACTAATAATCAGACCTGATT
CTGGAAACCCTCTTGACACTGTGTTAAAGGTTTTGGAGATTTTAGGTA
AGAAGTTTCCTGTTACTGAGAACTCAAAGGGTTACAAGTTGCTGCCAC
CTTATCTTAGAGTTATTCAAGGGGATGGAGTAGATATTAATACCTTAC
AAGAGATTGTAGAAGGCATGAAACAAAAAATGTGGAGTATTGAAAATA
TTGCCTTCGGTTCTGGTGGAGGTTTGCTACAGAAGTTGACAAGAGATC
TCTTGAATTGTTCCTTCAAGTGTAGCTATGTTGTAACTAATGGCCTTG
GGATTAACGTCTTCAAGGACCCAGTTGCTGATCCCAACAAAAGGTCCA
AAAAGGGCCGATTATCTTTACATAGGACGCCAGCAGGGAATTTTGTTA
CACTGGAGGAAGGAAAAGGAGACCTTGAGGAATATGGTCAGGATCTTC
TCCATACTGTCTTCAAGAATGGCAAGGTGACAAAAAGCTATTCATTTG
ATGAAATAAGAAAAAATGCACAGCTGAATATTGAACTGGAAGCAGCAC
ATCATTAGGCTTTATGACTGGGTGTGTTGTGTATGTAATACATA
ATGTTTATTGTACAGATGTGTGGGGTTTGTGTTTTATGATACATTACA
GCCAAATTATTTGTTGGTTTATGGACATACTGCCCTTTCATTTTTTT
CTTTTCCAGTGTTTAGGTGATCTCAAATTAGGAAATGCATTTAACCAT
GTAAAAGATGAGTGCTAAAGTAAGCTTTTTAGGGCCCTTTGCCAATAG
GTAGTCATTCAATCTGGTATTGATCTTTTCACAAATAACAGAACTGAG
AAACTTTTATATATAACTGATGATCACATAAAACAGATTTGCATAAAA
TTACCATGATTGCTTTATGTTTATATTTAACTTGTATTTTTGTACAAA
CAAGATTGTGTAAGATATATTTGAAGTTTCAGTGATTTAACAGTCTTT
CCAACTTTTCATGATTTTTATGAGCACAGACTTTCAAGAAAATACTTG
```

-continued

```
AAAATAAATTACATTGCCTTTTGTCCATTAATCAGCAAATAAAACATG
GCCTTAACAAAGTTGTTTGTGTTATTGTACAATTTGAAAATTATGTCG
GGACATACCCTATAGAATTACTAACCTTACTGCCCCTTGTAGAATATG
TATTAATCATTCTACATTAAAGAAAATAATGGTTCTTACTGGAATGTC
TAGGCACTGTACAGTTATTATATATCTTGGTTGTTGTATTGTACCAGT
GAAATGCCAAATTTGAAAGGCCTGTACTGCAATTTTATATGTCAGAGA
TTGCCTGTGGCTCTAATATGCACCTCAAGATTTTAAGGAGATAATGTT
TTTAGAGAGAATTTCTGCTTCCACTATAGAATATATACATAAATGTAA
AATACTTACAAAAGTGGAAGTAGTGTATTTTAAAGTAATTACACTTCT
GAATTTATTTTTCATATTCTATAGTTGGTATGACTTAAATGAATTACT
GGAGTGGGTAGTGAGTGTACTTAAATGTTTCAATTCTGTTATATTTTT
TATTAAGTTTTTAAAAAATTAAATTGGATATTAAATTGTATGGACATC
ATTTATTAATTTTAAACTGAATGCCCTCAATAAGTAATACTGAAGCAC
ATTCTTAAATGAAGATAAATTATCTCCAATGAAAAGCATGACATGTGT
TTCAATAGAAGAATCTTAAGTTGGCTAAATTCAAAGTGCTTGACATCA
AAATGTTCTAGAGTGATTAGCTACTAGATTCTGAATCATACATCACAT
CTGACTAGAGACCAGTTTCTTTCGAATGATTCTTTTATGTATGTAGAT
CTGTTCTTCTGAGGCAGCGGTTGGCCAACTATAGCCCAAAGGCCAAAT
TTGGACTTCTTTTTATAAATGCAGATTGTCTATGGCTGCTTTCCCACT
ACTCCAGCCTAAGGTAAACAGCTGCAATAGAAGCCAAATGAGAATCGC
AAAGCCCAAAATGTTTATTAACCTGCCCTTTACACAAAATTACACAAA
AAGTTTCCTGATCTCTGTTCTAAGAAAAGGAGTGTGCCTTGCATTTAA
AAGGAAATGTTGGTTTCTAGGGAAGGGAGGAGGCTAAATAATTGATAC
GGAATTTTCCTCTTTTGTCTTCTTTTTTCTCACTTAAGAATCCGATAC
TGGAAGACTGATTTAGAAAAGTTTTTAACATGACATTAAATGTGAAAT
TTTAAAAATTGAAAAGCCATAAATCATCTGTTTTAAATAGTTACATGA
GAAAATGATCACTAGAATAACCTAATTAGAAGTGTTATCTTCATTAAA
TGTTTTTTGTAAGTGGTATTAGAAAGAATATGTTTTTCAGATGGTTCT
TTAAACATGTAGTGAGAACAATAAGCATTATTCACTTTTAGTAAGTCT
TCTGTAATCCATGATATAAAATAATTTTAAAATGATTTTTTAATGTAT
TTGAGTAAAGATGAGTAGTATTAAGAAAAACACACATTTCTTCACAAA
ATGTGCTAAGGGGCGTGTAAAGAATCAAAAGAAACTATTACCAATAAT
AGTTTTGATAATCACCCATAATTTTGTGTTTAAACATTGAAATTATAG
TACAGACAGTATTCTCTGTGTTCTGTGAATTTCAGCAGCTTCAGAATA
GAGTTTAATTTAGAAATTTGCAGTGAAAAAAGCTATCTCTTTGTTCAC
AACCATAAATCAGGAGATGGAGATTAATTCTATTGGCTCTTAGTCACT
TGGAACTGATTAATTCTGACTTTCTGTCACTAAGCACTTGGTATTTGG
CCATCTCCATTCTGAGCACCAAACGGTTAACACGAATGTCCACTAGAA
CTCTGCTGTGTGTCACCCTTAAATCAGTCTAAATCTTCCAGACAAAAG
CAAATGGCATTTATGGATTTAAGTCATTAGATTTTCAACTGACATTAA
TTAATCCCTCTTGATTGATTATATCATCAAGTATTTATATCTTAAATA
```

-continued
```
GGAGGTAGGATTTCTGTGTTAAGACTCTTATTTGTACCCTATAATTAA
AGTAAAATGTTTTTTATGAGTATCCCTTGTTTTCCCTTCTTAAATTGT
TATCAAACAATTTTTATAATGAAATCTATCTTGGAAAATTAGAAAGAA
AAATGGCAAGGTATTTATTGTTCTGTTTGCCATAATTTAGAACTCACA
CTTAAGTATTTTGTAGTTTTACATTCCTTTTTAACCCATTCAGTGGAG
AATGTCAGCTTTTCTCCCAAGTTGTATGTTAAGTCTATTCTAATATGT
ACTCAACATCAAGTTATAAACATGTAATAAACATGGAAATAAAGTTTA
GCTCTATTAGTGAAGTGTTAAAAAAAAAAAAA
```

Primers used:

```
Forward primer sequence:
ATTGCCTTCGGTTCTGGTGG

Reverse primer sequence:
CGGCCCTTTTTGGACCTTTTG    Amplicon length: 155
```

Amplicon sequence:

```
ATTGCCTTCGGTTCTGGTGGAGGTTTGCTACAGAAGTTGACAAGAGAT
CTCTTGAATTGTTCCTTCAAGTGTAGCTATGTTGTAACTAATGGCCTT
GGGATTAACGTCTTCAAGGACCCAGTTGCTGATCCCAACAAAAGGTCC
AAAAAGGGCCG
```

The list of sequences given above are represented by SEQ ID No. 1 to 80, used in the present invention, which are being provided herein in PatentIn 3.5 format. The sequence listings are also being provided in hard copy as well as in electronic format on a CD_ROM. The complementary DNA sequences [cDNA] provided in the specification are complementary to the respective gene sequences and the said cDNA sequences are represented by SEQ ID Nos 41, 43, 45, 47, 49, 51, 53, 55, 57, 59, 61, 63, 65, 67, 69, 71, 73, 75, 77 and 79. It may be noted that the cDNA sequences are equivalent to mRNA sequences except that the base Thymine [T] in cDNA is replaced by the base Uracil [U] in mRNA. Further, the probe sequences for the genes useful in the detection of astrocytoma, it's grades and glioblastoma prognosis are represented by SEQ ID No. 42, 44, 46, 48, 50, 52, 54, 56, 58, 60, 62, 64, 66, 68, 70, 72, 74, 76, 78 and 80.

A ready reference for the said sequences used in the present invention is being provided here as under:
1. SEQ ID No. 1 represents forward primer of SYT1 gene
2. SEQ ID No. 2 represents reverse primer of SYT1 gene
3. SEQ ID No. 3 represents forward primer of RAB26 gene
4. SEQ ID No. 4 represents reverse primer of RAB26 gene
5. SEQ ID No. 5 represents forward primer of DIRAS2 gene
6. SEQ ID No. 6 represents reverse primer of DIRAS2 gene
7. SEQ ID No. 7 represents forward primer of RAB13 gene
8. SEQ ID No. 8 represents reverse primer of RAB13 gene
9. SEQ ID No.9 represents forward primer of IGFBP7 gene
10. SEQ ID No 10. represents reverse primer of IGFBP7 gene
11. SEQ ID No. 11 represents forward primer of COL6A1 gene
12. SEQ ID No. 12 represents reverse primer of COL6A1 gene
13. SEQ ID No. 13 represents forward primer of DCN gene
14. SEQ ID No. 14 represents reverse primer of DCN gene
15. SEQ ID No 15. represents forward primer of PLAT gene 16. SEQ ID No 16. represents reverse primer of PALT gene
17. SEQ ID No. 17 represents forward primer of LGALS3 gene
18. SEQ ID No. 18 represents reverse primer of LGALS3 gene
19. SEQ ID No. 19 represents forward primer of FABP7 gene
20. SEQ ID No. 20 represents reverse primer of FABP7 gene
21. SEQ ID No. 21 represents forward primer of LOX gene
22. SEQ ID No. 22 represents reverse primer of LOX gene
23. SEQ ID No. 23 represents forward primer of LAMB1 gene
24. SEQ ID No. 24 represents reverse primer of LAMB1 gene
25. SEQ ID No. 25 represents forward primer of IGFBP3 gene
26. SEQ ID No. 26 represents reverse primer of IGFBP3 gene
27. SEQ ID No. 27 represents forward primer of GADD45A gene
28. SEQ ID No. 28 represents reverse primer of GADD45A gene
29. SEQ ID No. 29 represents forward primer of FSTL1 gene
30. SEQ ID No. 30 represents reverse primer of FSTL1 gene
31. SEQ ID No. 31 represents forward primer of RHOC gene
32. SEQ ID No.32 represents reverse primer of RHOC gene
33. SEQ ID No. 33 represents forward primer of AEBP1 gene
34. SEQ ID No. 34 represents reverse primer of AEBP1 gene
35. SEQ ID No. 35 represents forward primer of B2M gene
36. SEQ ID No. 36 represents reverse primer of B2M gene
37. SEQ ID No. 37 represents forward primer of SOD2 gene
38. SEQ ID No.38 represents reverse primer of SOD2 gene
39. SEQ ID No.39 represents forward primer of PBEF1 gene
40. SEQ ID No. 40 represents reverse primer of PBEF1 gene
41. SEQ ID No. 41 represents cDNA of SYT1 gene
42. SEQ ID No. 42 represents an amplicon or nucleic acid probe for SYT1 gene
43. SEQ ID No.43 represents cDNA of RAB26 gene
44. SEQ ID No. 44 represents an amplicon or nucleic acid probe for RAB26 gene
45. SEQ ID No. 45 represents cDNA of DIRAS2 gene
46. SEQ ID No. 46 represents an amplicon or nucleic acid probe for DIRAS2 gene
47. SEQ ID No. 47 represents cDNA of RAB13 gene
48. SEQ ID No. 48 represents an amplicon or nucleic acid probe for RAB13 gene
49. SEQ ID No.49 represents cDNA of IGFBP7 gene
50. SEQ ID No 50 represents an amplicon or nucleic acid probe for IGFBP7 gene
51. SEQ ID No. 51 represents cDNA of COL6A1 gene
52. SEQ ID No. 52 represents an amplicon or nucleic acid probe for COL6A1 gene
53. SEQ ID No. 53 represents cDNA of DCN gene
54. SEQ ID No. 54 represents an amplicon or nucleic acid probe for DCN gene
55. SEQ ID No 55. represents cDNA of PLAT gene
56. SEQ ID No 56. represents an amplicon or nucleic acid probe for PALT gene
57. SEQ ID No. 57 represents cDNA of LGALS3 gene
58. SEQ ID No. 58 represents an amplicon or nucleic acid probe for LGALS3 gene
59. SEQ ID No. 59 represents cDNA of FABP7 gene
60. SEQ ID No. 60 represents an amplicon or nucleic acid probe for FABP7 gene
61. SEQ ID No. 61 represents cDNA of LOX gene
62. SEQ ID No. 62 represents an amplicon or nucleic acid probe for LOX gene.
63. SEQ ID No. 63 represents cDNA of LAMB 1 gene
64. SEQ ID No. 64 represents an amplicon or nucleic acid probe for LAMB 1 gene
65. SEQ ID No. 65 represents cDNA of IGFBP3 gene
66. SEQ ID No. 66 represents an amplicon or nucleic acid probe for IGFBP3 gene
67. SEQ ID No. 67 represents cDNA of GADD45A gene
68. SEQ ID No. 68 represents an amplicon or nucleic acid probe for GADD45A gene
69. SEQ ID No. 69 represents cDNA of FSTL1 gene
70. SEQ ID No. 70 represents an amplicon or nucleic acid probe for FSTL1 gene
71. SEQ ID No. 71 represents cDNA of RHOC gene
72. SEQ ID No.72 represents an amplicon or nucleic acid probe for RHOC gene
73. SEQ ID No. 73 represents cDNA of AEBP1 gene
74. SEQ ID No. 74 represents an amplicon or nucleic acid probe for AEBP1 gene
75. SEQ ID No. 75 represents cDNA of B2M gene
76. SEQ ID No. 76 represents an amplicon or nucleic acid probe for B2M gene
77. SEQ ID No. 77 represents cDNA of SOD2 gene
78. SEQ ID No.78 represents an amplicon or nucleic acid probe for SOD2 gene
79. SEQ ID No.79 represents cDNA of PBEF1 gene
80. SEQ ID No. 80 represents an amplicon or nucleic acid probe for PBEF1 gene The sample is preferably collected directly from the human subject's body. Preferred and convenient substances for sampling include blood, lymph or plasma, cerebrospinal fluid, other biopsy sample of cellular material from brain tissue. Cellular material includes any sample containing human cells, including samples of tissue, expressed tissue fluids (e.g., lymph or plasma) or tissue wash and the like. Tissue samples that can be collected include, but are not limited to, cell-containing material from the brain. This includes normal brain tissue, tumor tissue, tumor-adjacent tissue, and/or blood plasma from a site within the brain.

In accordance with the inventive methods, the tissue sample preferably contains cells that express a plurality of protein species and mRNA species, which proteins and/or mRNA species are detectably distinct from one another. "Obtaining" and "collecting" the sample are used interchangeably herein and encompass sampling, resecting, removing from in situ, aspirating, receiving, gathering, and/or transporting the tissue sample or a concentrate, sediment, precipitate, supernatant, filtrate, aspirate, or other fraction of any of these. For example, conventional biopsy methods are useful for obtaining the tissue sample. These include percutaneous biopsy, laparoscopic biopsy, surgical resection, tissue scrapes and swabs, sampling via stents, catheters, endoscopes, needles, surgical resection, and other known means. For example, to obtain a sample from inside the skull of the human subject; typically, Magnetic Resonance Imaging (MRI)-guided stereotactic techniques are employed, but other methods can be used.

The sample is alternatively derived from cultured human cells, cell-free extracts, or other specimens indirectly derived from a subject's body, as well as from substances taken directly from a subject's body. Samples may be stored before detection methods are applied (for example nucleic acid amplification and/or analysis, or immunochemical detection) by well known storage means that will preserve nucleic acids or proteins in a detectable and/or analyzable condition, such as quick freezing, or a controlled freezing regime, in the presence of a cryoprotectant, for example, dimethyl sulfoxide (DMSO), trehalose, glycerol, or propanediol-sucrose. Samples may also be pooled before or after storage for purposes of amplifying the nucleic acids specific for the said genes for analysis and detection, or for purposes of detecting the respective proteins.

The sample is used immediately or optionally pre-treated by refrigerated or frozen storage overnight, by dilution, by phenol-chloroform extraction, or by other like means, to remove factors that may inhibit various amplification reactions. The level of expression in the sample for the said proteins or their messenger ribonucleic acid (mRNA) is then detected quantitatively or semi-quantitatively.

Polynucleotides specific for the said genes, including mRNA species, are determined by base sequence similarity or homology to known nucleotide sequences. Base sequence homology is determined by conducting a base sequence similarity search of a genomics data base, such as the GenBank database of the National Center for Biotechnology Information (NCBI; www.ncbi.nlm.nih.gov/BLAST/), using a computerized algorithm, such as PowerBLAST, QBLAST, PSI-BLAST, PHI-BLAST, gapped or ungapped BLAST, or the "Align" program through the Baylor College of Medicine server (www.hgsc.bcm.tmc.edu/seq_clata). (Altchul, et al., 1997; Zhang and Madden, 1997; Madden et al., 1996; Altschul et al., 1990).

Preferably, polynucleotide sequences specific to the said genes, including an mRNA sequence, is at least 5 to 30 contiguous nucleotides long, more preferably at least 6 to 15 contiguous nucleotides long, and most preferably at least 7 to 10 contiguous nucleotides long. mRNA specific to any of the said genes can be, but is not necessarily, an mRNA species containing a nucleotide sequence that encodes a functional version of the said genes or fragments thereof. Also included among mRNAs specific to the said genes are splice variants.

Quantitative detection of levels of mRNAs specific to the said genes or their proteins, or of other proteins or mRNA species of interest in accordance with the present invention is done by any known method that provides a quantitative or semi-quantitative determination of expression. A quantitative method can be absolute or relative. An absolute quantitation provides an absolute value for the amount or level of expression in comparison to a standard, which amount or level is typically a mole, mass, or activity value normalized in terms of a specified mass of protein, mass of nucleic acid, number or mass of cells, body weight, or the like. Additionally, the quantitative or absolute value is optionally normalized in terms of a specified time period, i.e., expression level as a rate. A relative detection method provides a unitless relative value for the amount or level of expression, for example, in terms of a ratio of expression in a given sample relative to a control, such as normal tissue or the expression of a selected "housekeeping" gene. The skilled artisan is aware of other examples of quantitative and semi-quantitative detection methods.

In accordance with the inventive methods, the expression level of the proteins encoded by the said genes is optionally detected by immunochemical means, such as, but not limited to, enzyme-linked immunosorbent assay (ELISA), immunofluorescent assay (IFA), immunoelectrophoresis, immunochromatographic assay or immunohistochemical staining, employing polyclonal or monoclonal antibodies or antibody fragments against the said gene products. Antibodies or antibody fragments that target the said proteins are available commercially or can be produced by conventional means.

Similarly, the expression levels of other proteins of interest, in accordance with the inventive methods, can be detected by conventional immunochemical means as described above. Most preferably, quantitative or semi-quantitative detection of the expression level of mRNA species is accomplished by any of numerous methods of nucleic acid amplification (e.g., amplification of specific nucleic acid segments) in the form of RNA or cDNA, which RNA or cDNA amplification product is ultimately measured after amplification. The final amplification product of RNA or cDNA is measured by any conventional means, such as, but not limited to, densitometry, fluorescence detection, or any other suitable biochemical or physical assay system. Before amplification, it is preferable to extract or separate mRNA from genomic DNA in the sample and to amplify nucleic acids remaining in that fraction of the sample separated from the DNA, to avoid false positives that are caused by amplification of contaminating genomic DNA in the original specimen.

Histopathological means of classifying malignant tumors into grades are known for various kinds of malignant tumor, including astrocytomas. (Daumas-Duport et al., 1988).

The present inventive method can be used to diagnose astrocytoma, wherein a higher level of expression of RAB13 or a lower level of expression of any or a combination of genes from the group consisting of, but not limited to SYT1, RAB26 and DIRAS2 is indicative of the presence of astrocytoma (See FIG. 1).

The present inventive method can be used to diagnose malignant astrocytoma (AA, GBM), wherein a higher level of expression of IGFBP7 is indicative of the presence of malignant astrocytoma. (See FIG. 2)

The present inventive method can be used to diagnose the presence of glioblastoma, since GBMs generally over-express any or a combination of genes from the group consisting of, but not limited to, COL6A1, DCN, PLAT, LGALS3, FABP7, LOX, LAMB1, IGFBP3, GADD45A, FSTL1, RHOC, B2M and PBEF1. (See FIG. 3). Primary and secondary GBMs are frequently indistinguishable with conventional histopathological methods, but using the inventive method, these types are readily distinguished, since primary GBMs generally over express any or a combination of genes from the group consisting of, but not limited to AEBP1 and SOD2. (See FIG. 4).

In a preferred embodiment the above identified genes are used in combination with known markers such as EGFR, p53 and Ki-67 for determining the presence of astrocytoma.

Further, present invention method can also be used for the prognosis of glioblastoma in human subjects where in higher expression of PBEF1 indicates the poorer survival of the human subject from which the test sample has been obtained (FIG. 11)

The foregoing descriptions of the methods of the present invention are only illustrative and by no means exhaustive. When these features of the present invention are employed, diagnostic and treatment decisions can be more appropriately optimized for the individual astrocytoma and glioblastoma patient, and the prospects for his or her survival can be enhanced.

Transcriptome Analysis of Astrocytomas

We analyzed the expression profile of 18981 human genes using 19k cDNA microarrays for twenty five samples of diffusely infiltrating astrocytoma comprising four diffuse astrocytoma (DA; Gr II), five AA (Gr. III) and sixteen GBM (Gr IV; six secondary and ten primary). 14,929 genes for which the data was available for more than 50% of the samples within each grade were only considered for subsequent analysis. The data obtained from image analysis was filtered, normalized and log 2 transformed before being used for further studies. To identify the significantly differentially regulated genes between normal and astrocytoma samples as well as between different grades of astrocytoma, the data were subjected to Significance Analysis of Microarrays using the one-class and two-class option as required.

SAM Analysis Identifies Grade Specific Genes

Examination of 14,929 genes data set derived from 25 astrocytoma samples through SAM analysis found 385 to be up regulated and 911 genes to be down regulated in all groups of astrocytoma in comparison to normal brain sample. DAs (Gr. II) are diffusely infiltrating low-grade astrocytoma which progress over to malignant grade III anaplastic astrocytoma and grade IV GBM over period of 5-10 yrs (4, 5, 12). AAs (Gr. III) are less malignant than GBMs with AA patients having a mean survival of 2-3 years in comparison to GBM patients whose mean survival is less than a year (3, 5, 13, 14). To identify the genes which are differentially regulated between GBM and lower-grade astrocytoma (LGA) i.e., DA and AA, we subjected the data obtained from 9 of the later group (4 DA and 5 AA) and 16 GBM (10 primary and 6 secondary) through SAM analysis. We found 41 genes up regulated in LGA (DA & AA) as against GBM and 37 genes up regulated in GBM as against LGA. Since secondary GBM progresses from lower grades, i.e.; DA or AA, it is likely that these tumors share an expression profile with DA or AA as against primary GBM. Thus to obtain the expression profile specific to progressive astrocytoma (DA, AA, Secondary GBM) as against primary GBM (de novo GBM), we compared the data obtained from 15 samples belonging to progressive astrocytoma (4 DA, 5 AA and 6 secondary GBM) and 10 samples belonging to primary GBM through SAM analysis. We found 20 genes up regulated in progressive astrocytoma as against primary GBM and 45 genes up regulated in primary GBM as against progressive astrocytoma.

Real-Time RT-Quantitative PCR Validation of SAM Identified Genes

In order to identify genes whose differential expression characterize astrocytomas, malignant astrocytomas (AA, GBM) or primary glioblastomas, we critically analyzed the data obtained from SAM analysis and some of the interesting genes were selected for further validation. Expression pattern of the selected was confirmed by real-time RT-quantitative PCR analysis on independent set of 100 samples of different grades of astrocytomas and glioblastoma. Sample set includes 5 DAs, 31 AAs, 20 secondary GBMs, 35 primary GBMs and 9 normal brain samples. Statistical significance of expression pattern of a gene was examined by Mann-Whitney test. P value of equal to or less than 0.05 was considered statistically significant.

Identification of Down- or Up-Regulated, Genes in Astrocytoma

Using SAM analysis and subsequent RT-qPCR analysis, we have identified the genes SYT1, RAB26, DIRAS2 to be down-regulated in all grades of astrocytoma where as RAB13 is up-regulated in all grades of astrocytoma.

Synaptotagmin I (SYT1) was found to be down regulated by more than 4 fold in DAs(5/5; 100%), AAs (25/31; 80%), secondary GBMs (17/20; 85%) and primary GBMs (31/35; 88.5%) but not in normal brain samples (0/9; 0%). P value found to be statistically significant between Normal and all grades of astrocytoma viz., Normal vs. DA (0.001), Normal vs. AA(<0.001), Normal vs. secondary GBM (<0.001), Normal vs. primary GBM (<0.001) (FIG. 1. A).

RAB26, member RAS oncogene family (RAB26) was found to be down regulated by more than 4 fold in DAs (5/5; 100%), AAs (21/30; 70%), secondary GBMs (19/20; 95%) and primary GBMs (31/35; 88.5%) but not in normal brain samples (0/9; 0%). P value found to be statistically significant between Normal and all grades of astrocytoma viz., Normal vs. DA (0.001), Normal vs. AA (<0.001), Normal vs. secondary GBM (<0.001), Normal vs. primary GBM (<0.001) (FIG. 1. B).

DIRAS family, GTP-binding RAS-like 2 (DIRAS2) was found to be down regulated by more than 4 fold in DAs (4/5; 80%), AAs (19/31; 61.2%), secondary GBMs (20/20; 100%) and primary GBMs (29/35; 82.8%) but not in normal brain samples (0/9; 0%). P value found to be statistically significant between Normal and all grades of astrocytoma viz., Normal vs. DA (0.001), Normal vs. AA (<0.001), Normal vs. secondary GBM (<0.001), Normal vs. primary GBM (<0.001) (FIG. 1. C).

RAB13, member RAS oncogene family (RAB13) was found to be down regulated by more than 4 fold in majority of DAs (4/5; 80%), AAs(24/30; 80%), secondary GBMs (17/20; 85%) and primary GBMs (34/35; 97.1%) but not in normal brain samples (1/9; 11.1%). P value found to be statistically significant between Normal and all grades of astrocytoma viz., Normal vs. DA (0.059), Normal vs. AA (<0.001), Normal vs. secondary GBM (<0.001), Normal vs. primary GBM (<0.001) (FIG. 1. D).

Identification of Up-Regulated Gene(s) in Malignant Astrocytoma (AA &GBM)

Insulin-like growth factor binding protein 7 (IGFBP7) was found to be up-regulated mainly in malignant astrocytomas (AA, GBM). Over-expression in malignant astrocytomas in comparison to controls is found to be statistically significant—Normal vs. AA (P=0.002), Normal vs. secondary GBM (P=0.01), Normal vs. primary GBM (P<0.001)—but not in benign astrocytomas (Normal vs. DA (P=0.297). IGFBP7 is found to be up-regulated by more than 4 fold majority of AAs (25/31; 80%), secondary GBMs (14/20; 70%) and primary GBMs (32/35; 91%) but not in controls (2/9; 22%), and DAs (3/5; 60%) (FIG. 2).

In addition, protein expression pattern of IGFBP7 was analyzed by immunohistochemistry. In the normal brain, neurons and glial cells were negative for IGFBP-7. There was a faint to moderate staining of parenchymal and leptomeningeal vessels {data not shown}. Only 1/9 of DAs and 40% (4/10) cases of AA showed positive staining of tumor cell cytoplasm. Among GBMs, 80% (12/15) cases of secondary GBM and 100% (19/19) of primary GBMs showed positive staining for IGFBP-7 in the tumor cells (FIG. 5).

Identification of GBM Specific Genes

Using SAM analysis and subsequent RT-qPCR analysis, the genes COL6A1, DCN, PLAT, LGALS3, FABP7, LOX, LAMB1, IGFBP3, GADD45A, FSTL1, RHOC, B2M were found to be over-expressed mainly in GBMs. Their over-expression in GBMs in comparison to controls as well as lower-grade samples (LGA), i.e., DA and AA was found to be statistically significant.

Collagen, type VI, alpha 1 (COL6A1) is found to be up-regulated by more than 3 fold in majority of GBMs (31/55; 54.5%) but in fewer no. of controls (1/9; 11%) and LGAs (11/36; 30.5%). P value obtained from Mann-Whitney U test for the comparison of GBM vs. Normal is <0.001 and for the comparison of GBM vs. LGA is 0.009 (FIG. 3. A).

Decorin (DCN) is found to be up-regulated by more than 4 fold in majority of GBMs (43/54; 79.6%) but in fewer no. of controls (4/9; 44%) and in LGAs (14/36; 38.9%). P value obtained from Mann-Whitney U test for the comparison of GBM vs. Normal is 0.003 and for the comparison of GBM vs. LGA is <0.001 (FIG. 3. B).

Plasminogen activator, tissue (PLAT) is found to be up-regulated by more than 4 fold in approximately half the no. of GBMs (28/54; 51.8%) but in none of the controls (0/9; 0%) and in very few LGAs (4/36; 11.1%). P value obtained from Mann-Whitney U test for the comparison of GBM vs. Normal is 0.001 and for the comparison of GBM vs. LGA is <0.001 (FIG. 3. C).

Lectin, galactoside-binding, soluble, 3 (LGALS3) is found to be up-regulated by more than 4 fold in majority of GBMs (37/55; 67.2%) but in fewer no. of controls (1/9; 11%) and LGAs (6/36; 16.7%). P value obtained from Mann-Whitney U test for the comparison of GBM vs. Normal is 0.001 and for the comparison of GBM vs. LGA is <0.001 (FIG. 3. D).

Fatty acid binding protein 7, brain (FABP7) is found to be up-regulated by more than 4 fold in majority of GBMs (35/55; 63.6%) but in fewer no. of controls (1/9; 11%) and in none of LGAs (0/36; 0%). P value obtained from Mann-Whitney U test for the comparison of GBM vs. Normal is 0.04 and for the comparison of GBM vs. LGA is <0.001 (FIG. 3. E).

Lysyl oxidase (LOX) is found to be up-regulated by more than 4 fold in majority of GBMs (34/55; 61.8%) but in fewer no. of controls (2/9; 22%) and LGAs (10/36; 27.8%). P value obtained from Mann-Whitney U test for the comparison of GBM vs. Normal is 0.03 and for the comparison of GBM vs. LGA is <0.001 (FIG. 3. F).

Laminin, beta 1 (LAMB1) is found to be up-regulated by more than 2 fold in majority of GBMs (46/55; 83.6%) but in fewer no. of controls (1/9; 11%) and LGAs (5/36; 13.9%). P value obtained from Mann-Whitney U test for the comparison of GBM vs. Normal is <0.001 and for the comparison of GBM vs. LGA is <0.001 (FIG. 3. G).

Insulin-like growth factor binding protein 3 (IGFBP3) is found to be up-regulated by more than 4 fold in majority of GBMs (34/55; 61.8%) but in fewer no. of controls (0/9; 0%) and LGAs (8/36; 22.2%). P value obtained from Mann-Whitney U test for the comparison of GBM vs. Normal is <0.001 and for the comparison of GBM vs. LGA is <0.001 (FIG. 3.11). In addition to this, protein expression pattern of IGFBP-3 was analyzed by immunohistochemistry. In the normal brain, IGFBP-3 showed a faint cytoplasmic labeling (1+) of the neurons. The astrocytes, oligodendrocytes and blood vessels were not labeled {data not shown}. Among astrocytomas, 33.33% (3/9) of DAs and 80.0% (8/10) of AAs showed positive staining. Among GBMs, 86.66% (13/15) of secondary GBMs and 100% (19/19) of primary GBMs showed positive staining for IGFBP-3. (FIG. 6)

Growth arrest and DNA-damage-inducible, alpha (GADD45A) is found to be up-regulated by more than 4 fold in majority of GBMs (32/55; 58.2%) but in fewer no. of controls (0/9; 0%) and LGAs (8/36; 22.2%). P value obtained from Mann-Whitney U test for the comparison of GBM vs. Normal is <0.001 and for the comparison of GBM vs. LGA is <0.001 (FIG. 3. I). We also analyzed the expression pattern of GADD45A by immunohistochemical staining (FIG. 7). Among primary and secondary GBM samples tested, 58.0% (7/12) and 50.0% (3/6) of them respectively showed strong positive cytoplasmic staining for GADD45A. The percentage positively for GADD45A staining in AA (Gr. and DA (Gr. II) was found to be 14.0% (1/7) and 00% (0/3) respectively. The average percent positive tumor cells were found to be higher among primary GBM samples (30.0%) followed by 25.0% and 20.0% among secondary GBM and AA respectively. Analysis of five normal brain samples showed glial cells to be negative for GADD45A staining.

Follistatin-like 1 (FSTL1) is found to be up-regulated by more than 4 fold in majority of GBMs (39/55; 70.9%) but in fewer no. of controls (0/9; 0%) and LGAs (4/36; 11.1%). P value obtained from Mann-Whitney U test for the comparison of GBM vs. Normal is <0.001 and for the comparison of GBM vs. LGA is <0.001 (FIG. 3.1). Immunohistochemical analysis revealed that 85.0% (18/21) and 86.0% (9/15) of primary and secondary GBM respectively are positive for FSTL1 protein staining (FIG. 8). As expected, reduced positively was found among AA (30.0%; 3/10) and DA (0.0%; 0/10). Staining of normal brain revealed glial cells to be negative for FSTL1 staining. The average percent positive tumor cells was found to be higher among primary GBM and secondary GBM (31.0 and 24% respectively) as against only 13.0% among AA cases suggesting the fact FSTL1 is expressed in very high levels among GBMs.

Ras homolog gene family, member C(RHOC) is found to be up-regulated by more than 2 fold in majority of GBMs (37/55; 67.3%) but in fewer no. of controls (1/9; 11.1%) and LGAs (16/36; 44.4%). P value obtained from Mann-Whitney U test for the comparison of GBM vs. Normal is <0.001 and for the comparison of GBM vs. LGA is 0.021 (FIG. 3. K).

Beta-2-microglobulin (B2M) is found to be up-regulated by more than 4 fold in majority of GBMs (34/55; 61.8%) but in fewer no. of controls (1/9; 11.1%) and LGAs (17/36; 47.2%). P value obtained from Mann-Whitney U test for the comparison of GBM vs. Normal is 0.004 and for the comparison of GBM vs. LGA is 0.022 (FIG. 3.L). Immunohistochemical staining for the expression of B2M confirmed the mRNA expression pattern (FIG. 9). While most GBM samples tested positive for a strong cytoplasmic staining (82.3%; 14/17), only 28.57% of anaplastic astrocytoma (2/7) and none of diffuse astrocytoma samples (0/3) showed positive staining.

PBEF1 transcript levels were up regulated more than three fold (Log 2 ratio=1.585) in majority of GBMs (63.60%; 35/55 with a mean log 2 ratio of 2.48) in comparison to AAs (9.60%; 3/31 with a mean log 2 ratio of 0.44), DAs (0.00%; 0/5 with a mean log 2 ratio of 0.50) and normal brain samples (0.00%; 0/9) with a P value <0.001 (FIG. 3 M). Statistical significance was assessed by Mann-Whitney test using GraphPad PRISM software. The staining pattern of PBEF1 was generally found to be granular and diffuse cytoplasmic. We found a vast majority of GBMs (72.22%; 26/36) found to be positive for PBEF1 staining (FIG. 10 E, F). As expected, reduced percentage of samples among AAs (40.00%; 4/10) and DAs (20.00%; 2/10) showed PBEF1 positive staining (FIG. 10 B, C). Further, the average percent positive tumor cells were+found to be high among GBMs (37.50%) as against 22.00% and 8.50% among AAs and DAs respectively suggesting the fact that PBEF1 is expressed in very high levels among GBMs. The staining of normal brain revealed that the glial cells are negative for PBEF1 staining (FIG. 10 A).

Identification of Primary GBM Specific Genes

Using SAM analysis and subsequent RT-qPCR analysis, we have also found two genes, namely, AEBP1 and SOD2 whose over-expression is characteristic to primary GBM.

AE binding protein 1 (AEBP1) is found to be up-regulated by more than 2 fold in majority of primary GBMs (29/35; 82.8%) but in fewer no. of controls (1/9; 11.1%), DAs (2/5; 40%), AAs (9/31; 29%) and secondary GBMs (9/20; 45%). The difference in transcript levels between primary GBM and all other groups is statistically significant: primary GBM vs. controls (P=0.002); primary GBM vs. DAs (P=0.043); primary GBM vs. AAs (P<0.001) and primary GBM vs. secondary GBMs (P=0.027) (FIG. 4. A).

Superoxide dismutase 2, mitochondrial (SOD2) is found to be up-regulated by more than 4 fold in majority of primary GBMs (25/35; 71.4%) but in fewer no. of controls (0/9; 0%), DAs (0/5; 0%), AAs (5/31; 16.1%) and secondary GBMs (4/20; 20%). The difference in transcript levels between primary GBM and all other groups is statistically significant: primary GBM vs. controls (P=0.001); primary GBM vs. DAs (P=0.012); primary GBM vs. AAs (P<0.001) and primary GBM vs. secondary GBMs (P=0.001) (FIG. 4. B).

Survival Value of PBEF1

To analyze the survival value of PBEF1, we subjected a different set of 51 retrospective GBM cases where follow up was available, for expression of PBEF1. In GBM patients, while the prognostic significance of clinical variables in predicting survival have been clearly defined, altered protein expression of the well known genetic alteration found in these tumors, like over-expression of p53 and EGFR expression, have individually failed to give a clear cut prognostic significance, with confounding results in different studies. Therefore, for the purpose of multivariate analysis, we immunostained the sections to study the expression of p53 and EGFR in order to analyze the significance of their co-expression with PBEF1 with respect to patient survival.

Correlating the expression of PBEF1 with survival among GBM patients, in univariate analysis, the median survival of the group which was positive for PBEF1 was lesser than that of the group negative for PBEF1, albeit with lack of statistical significance (12 months vs. 16 months respectively, p=0.16; FIG. 11 A). In multivariate analysis, while PBEF-1 expression by itself did not correlate with survival, its co-expression with p53 showed a trend towards poorer survival. The median survival of the group positive for both the markers was 8 months (red line), as compared to 14 months (green line) of the group negative for both or either of them (P=0.08; FIG. 11 B). We also noted that radiotherapy, KPS at presentation and p53 expression were significant independent predictors of survival at all steps in the multivariate analysis (data not shown). The data put together suggest that PBEF1 is a potential prognostic marker amongst GBM patients particularly in combination with aberrant p53 expression.

Accordingly the present invention comprises the determination of level of expression of single or combination of genes selected from the group comprising of SYT1, RAB26, DIRAS2 and RAB13 in a test sample of brain tissue cells obtained from said human subject and in a control sample of known normal brain tissue cells, wherein a higher level of expression of RAB13 in the test sample or a lower level of expression of SYT1, RAB26, DIRAS2 in the test sample, as compared to the control sample, indicates the presence of astrocytoma in the human subject from which the test sample is obtained.

In an embodiment of the present invention, the expression level of said genes is determined by checking the level of RNA transcripts of the said genes by employing an oligonucleotide in nucleic acid-based detection methods such as in situ hybridization, RT-PCR analysis etc. or optionally the expression level of said genes is determined by checking the level of respective proteins of said genes by employing an antibody in protein-based detection methods such as immunohistochemistry, western blot analysis and ELISA etc.

Accordingly the present invention, the present invention also provides a kit for characterizing astrocytoma in a human subject, wherein the said kit comprising:
a) reagent capable of specifically detecting the presence or absence of a single or combination of, said genes such as SYT1, RAB26, DIRAS2 and RAB13.
b) instructions for using said kit for detecting the presence of astrocytoma in said human subject.

In another embodiment kit for detecting the presence of astrocytoma in a human subject, wherein the said kit comprises:
[a] reagents capable of specifically detecting the level of expression of single or combination of genes selected from the group comprising of SYT1, RAB26, DIRAS2 and RAB13;
[b] instructions for using said kit for characterizing astrocytoma in said human subject. The reagents used in such kits preferably comprise of an amplicon or nucleic acid probe represented by SEQ ID No. 42, 44, 46 and 48.

In another embodiment, the present invention also provides a kit for identifying the malignant astrocytoma (AA, GBM) in a human subject, wherein the said kit comprising:
a) a reagent capable of specifically detecting the level of expression of a the gene IGFBP7.
b) instructions for using said kit for identifying the malignant astrocytoma (AA, GBM) in said human subject. The reagents used in such kits preferably comprise of an amplicon or nucleic acid probe represented by SEQ ID No. 50.

The present invention also provides a kit for detecting the presence of malignant astrocytoma in a human subject, wherein the said kit comprises:
a) reagent comprises an antibody that specifically binds to proteins encoded by the said genes.
b) instructions for using said kit for characterizing astrocytoma in said human subject In another embodiment, the present invention also provides a kit for detecting the presence of glioblastoma (GBM) in a human subject, wherein the said kit comprising:
a) reagent capable of specifically detecting the level of expression of a single or combination of said genes such as COL6A1, DCN, PLAT, LGALS3, FABP7, LOX, LAMB1, IGFBP3, GADD45A, FSTL1, RHOC, B2M and PBEF1
b) instructions for using said kit for detecting the presence of glioblastoma in said human subject. The reagents used in such kits preferably comprise of an amplicon or nucleic acid probe represented by SEQ ID No. 52, 54, 56, 58, 60, 62, 64, 66, 68, 70, 72, 76 and 80.

The present invention also provides a kit for detecting the presence of glioblastoma in a human subject, wherein the said kit comprises:
a) reagent comprises an antibody that specifically binds to proteins encoded by the said genes.
b) instructions for using said kit for detecting the presence of glioblastoma in said human subject In yet other embodiment, the present invention provides a kit for identifying the type of glioblastoma in a human subject, wherein the said kit comprising:
a) reagent capable of specifically detecting the level of expression of a single or the combination of said, genes such as AEBP1, SOD2.
b) instructions for using said kit for identifying the type of glioblastoma in said human subject. The reagents used in such kits preferably comprise of an amplicon or nucleic acid probe represented by SEQ ID No. 74 and 78.

The present invention also provides a kit for identifying the type of glioblastoma in a human subject, wherein the said kit comprises:
a) the reagent comprises an antibody that specifically binds to proteins encoded by the said genes.
b) instructions for using said kit for identifying the type of glioblastoma in said human subject The present invention also provides a kit to determine the prognosis of glioblastoma in a human subject, wherein the said kit comprising:
a) reagent capable of specifically detecting the presence or absence of a PBEF1.
b) instructions for using said kit to determine the prognosis of glioblastoma in said human subject.

The present invention also provides a kit for determining the prognosis of glioblastoma in a human subject, wherein the said kit comprises:
[a] reagent capable of specifically detecting the level of expression of the gene PBEF1;

[b] instructions for using said kit for determining the prognosis of glioblastoma in said human subject. The reagents used in such kits preferably comprise an amplicon or nucleic acid probe represented by SEQ ID No. 80.

BRIEF DESCRIPTION OF FIGURES

FIG. 1. Scatter plots of the genes that are differentially regulated in astrocytoma in comparison to normal brain tissue.

Log 2-transformed gene expression ratios obtained from real-time quantitative PCR analysis are plotted for SYT1 i.e FIG. 1A, RAB26 i.e FIG. 1B, DIRAS2 i.e FIG. 1C and RAB13 i.e FIG. 1D. Each dot represents a data derived from one sample. Horizontal bar represents the median log 2 ratio of the corresponding group.

Figure 2:
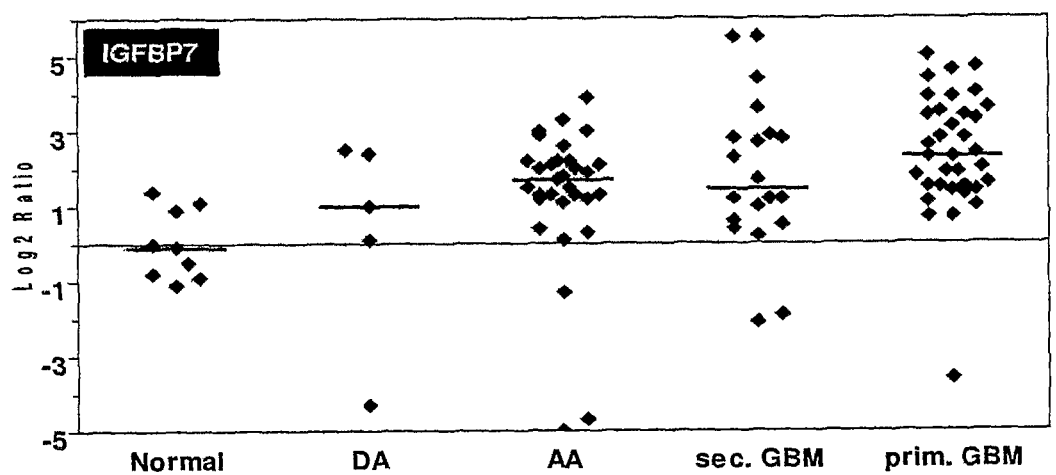

FIG. 2. Scatter plots of the genes that are up-regulated in malignant astrocytoma (AA, GBM) in comparison to normal brain tissue.

Log 2-transformed gene expression ratios obtained from real-time quantitative PCR analysis are plotted for IGFBP7. Each dot represents a data derived from one sample. Horizontal bar represents the median log 2 ratio of the corresponding group.

FIG. 3. Scatter plots of glioblastoma specific genes.

Figure 3A:
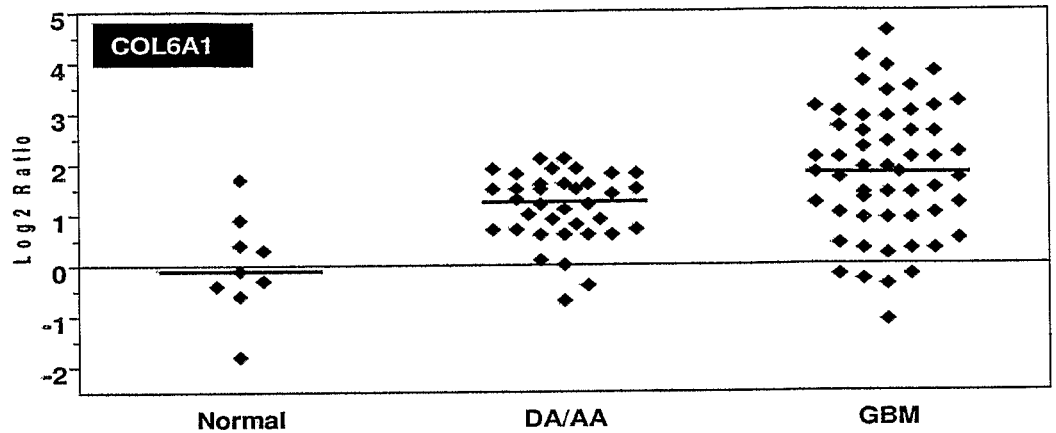
Figure 3B:
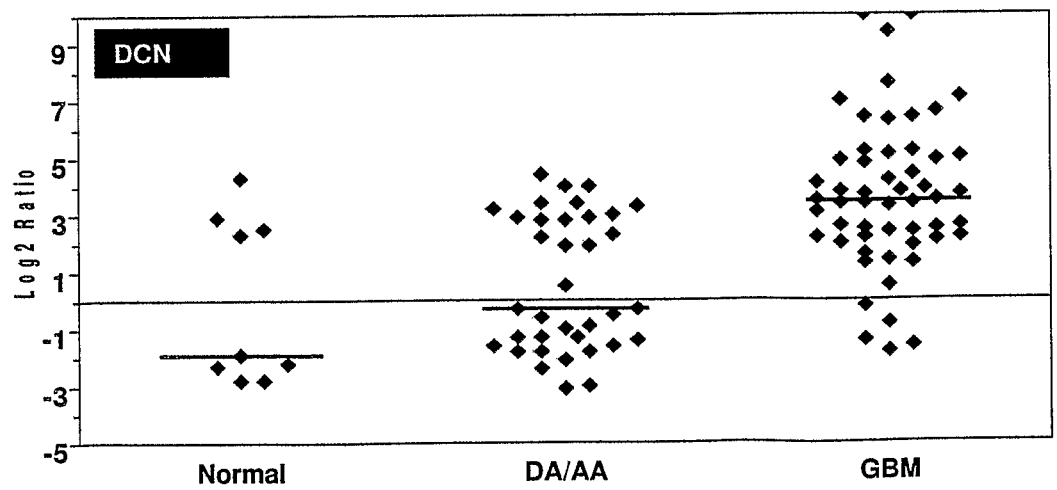
Figure 3C:
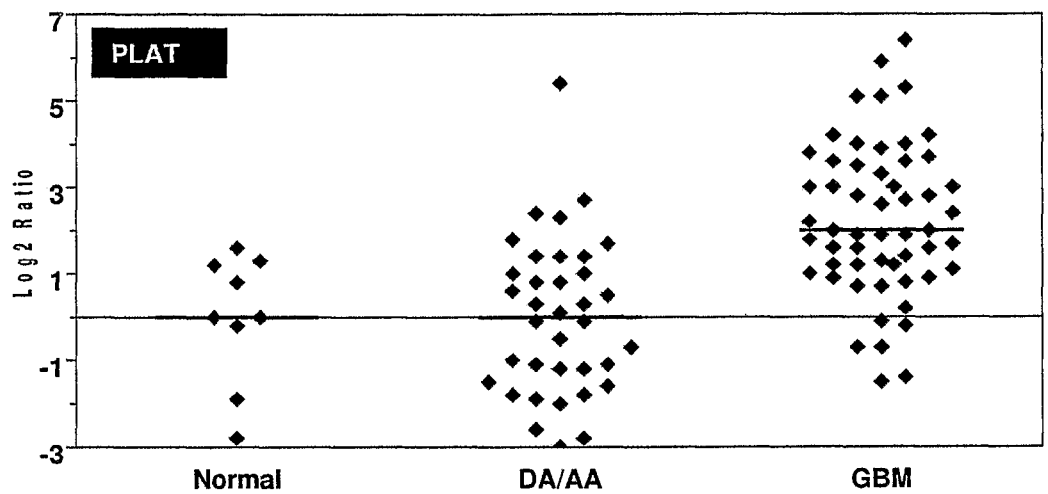
Figure 3D:
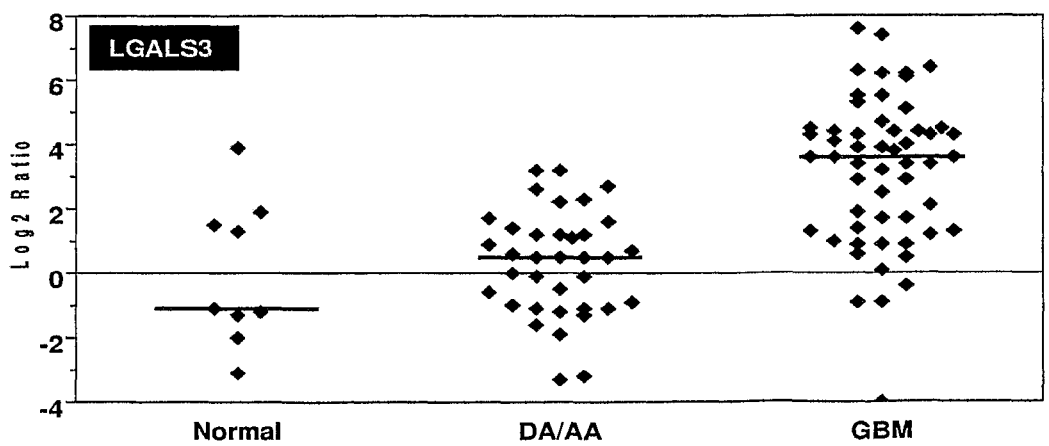
Figure 3E:
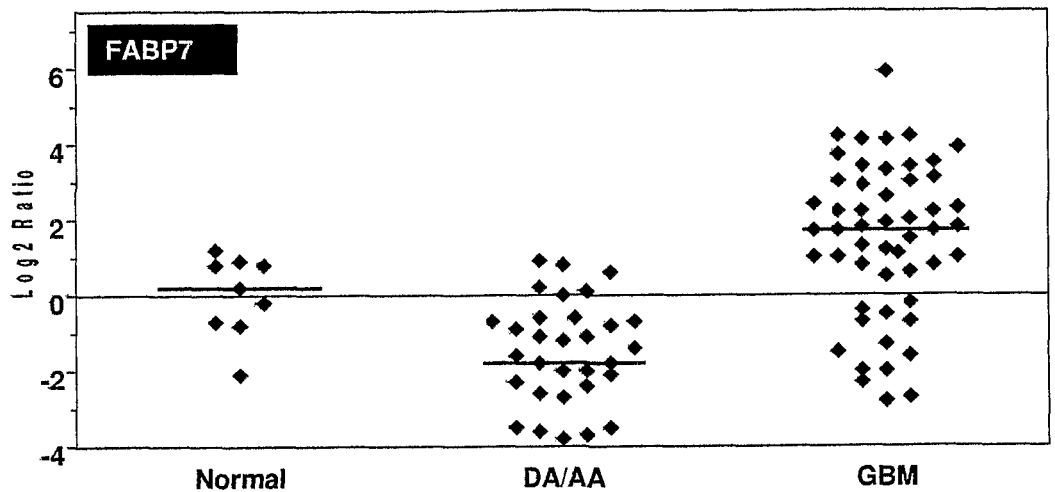
Figure 3F:
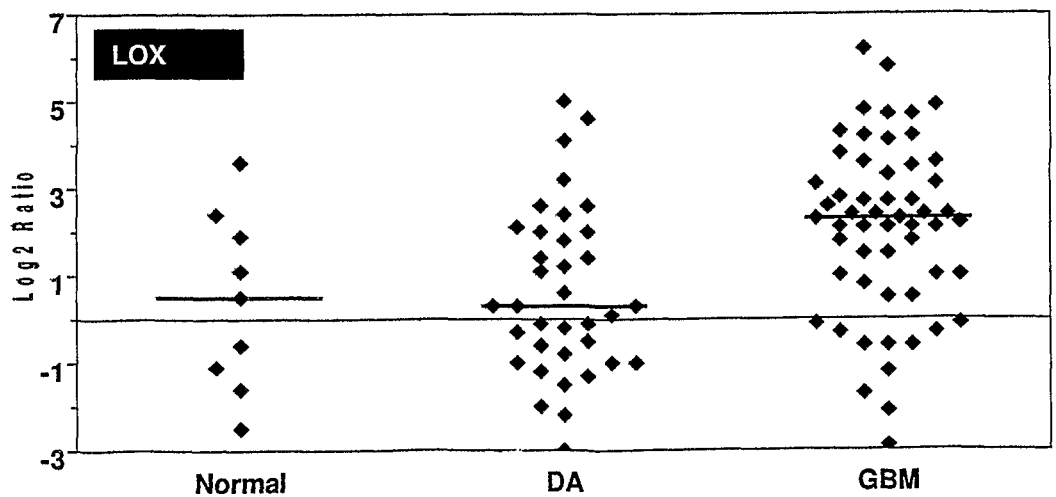
Figure 3G:
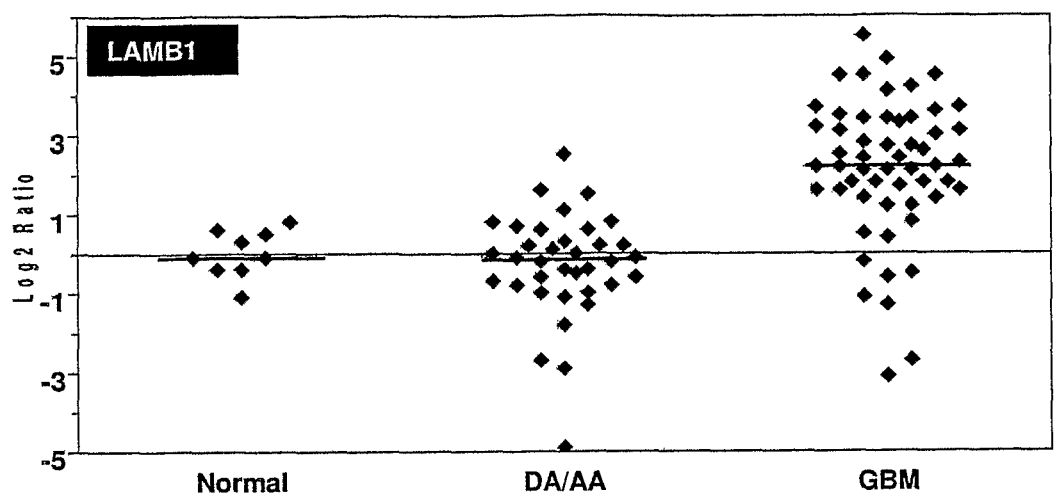
Figure 3H:
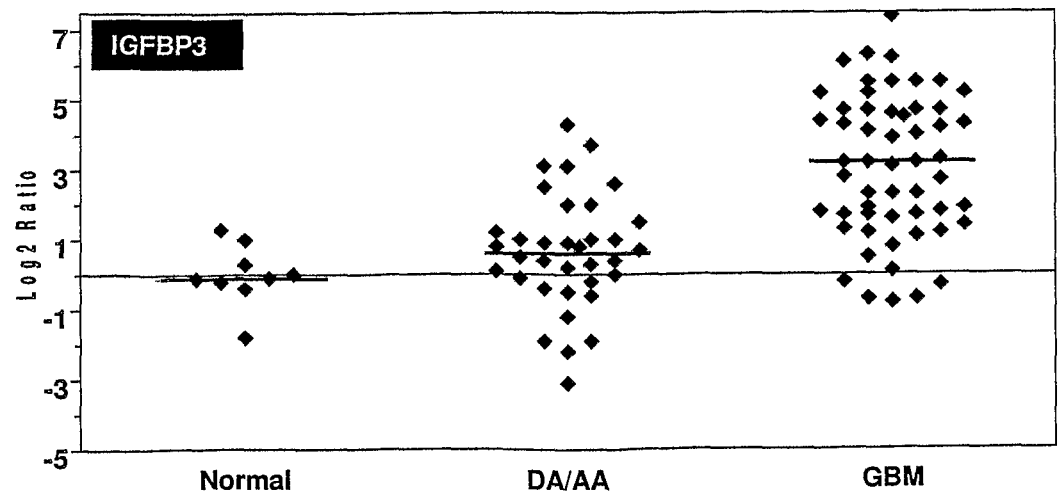
Figure 3I:
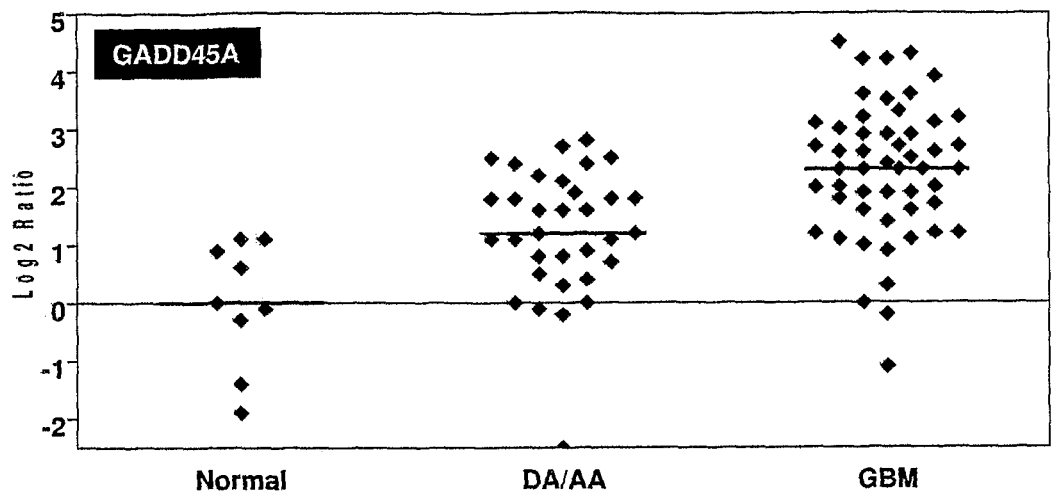
Figure 3J:
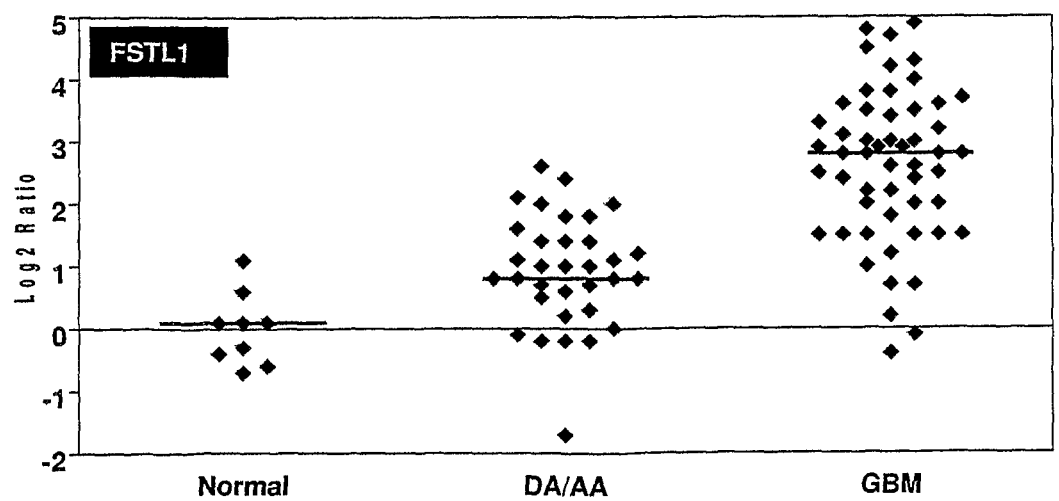
Figure 3K:
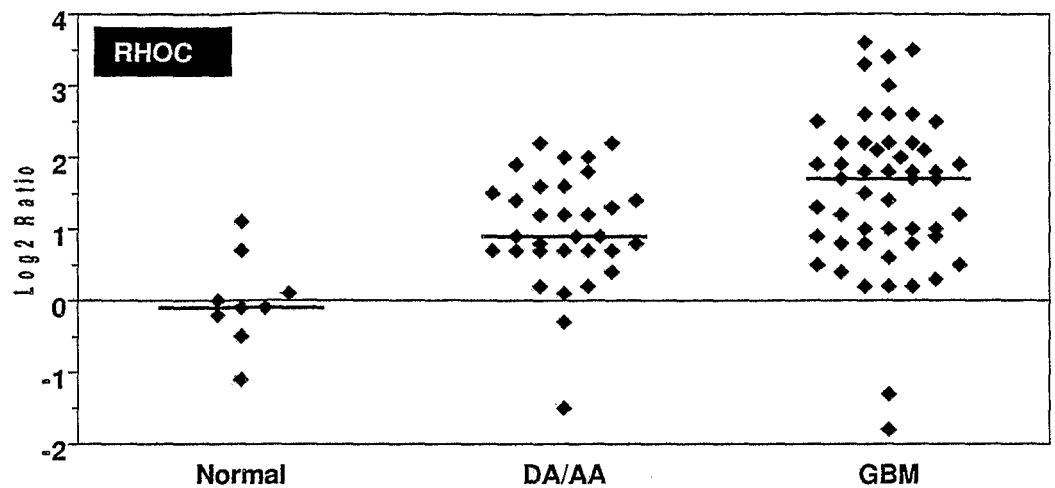
Figure 3L:
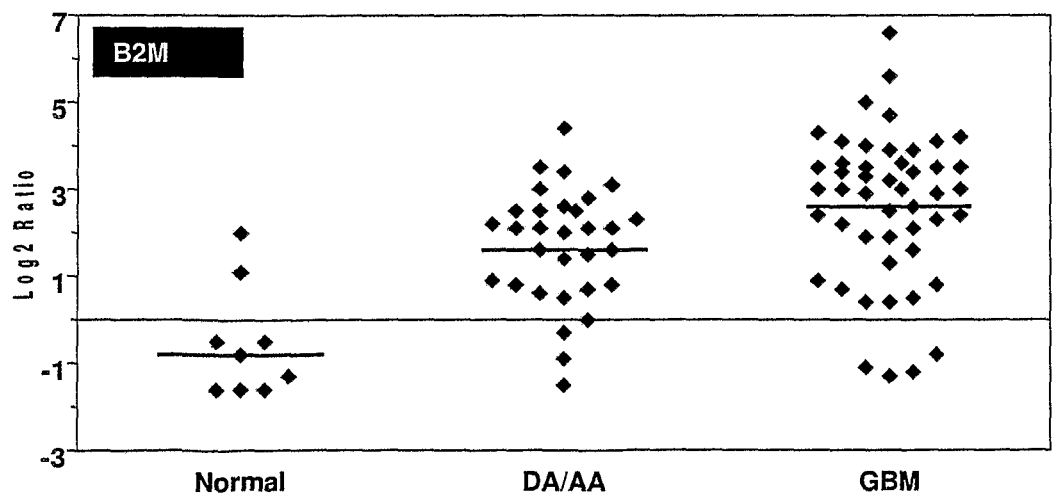
Figure 3M:
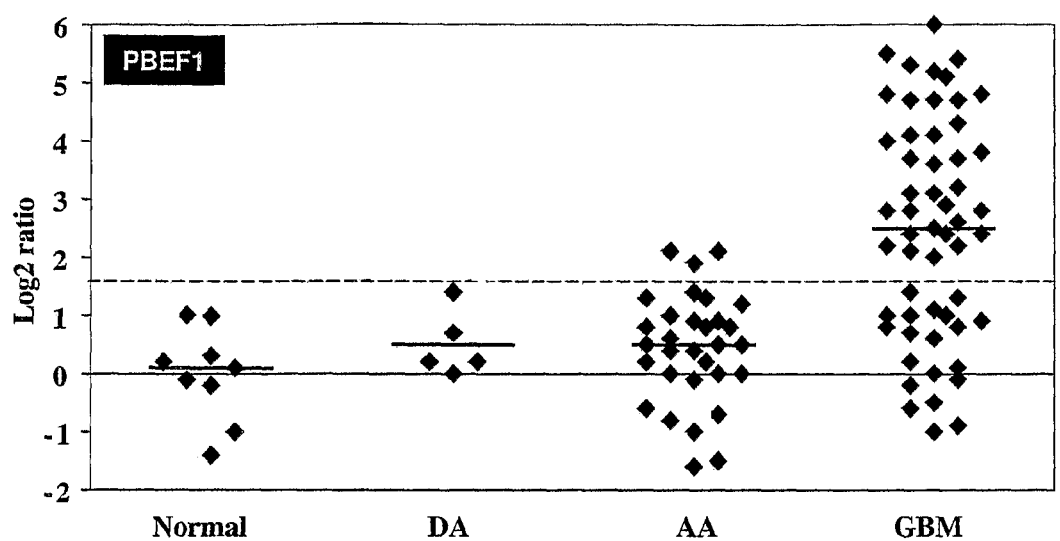

Log 2-transformed gene expression ratios obtained from real-time quantitative PCR analysis are plotted for COL6A1 i.e. FIG. 3A, DCN i.e. FIG. 3B, PLAT i.e FIG. 3C, LGALS3 i.e 3D, FABP7 i.e FIG. 3E, LOX i.e FIG. 3F, LAMB1 i.e FIG. 3G, IGFBP3 i.e FIG. 3H, GADD45A i.e FIG. 3I, FSTL1 i.e FIG. 3J, RHOC i.e FIG. 3K, B2M i.e FIG. 3L and PBEF1 i.e FIG. 3M. Each dot represents a data derived from one sample. Horizontal bar represents the median log 2 ratio of the corresponding group.

FIG. 4. Scatter plots of primary glioblastoma specific genes.

Figure 4A:
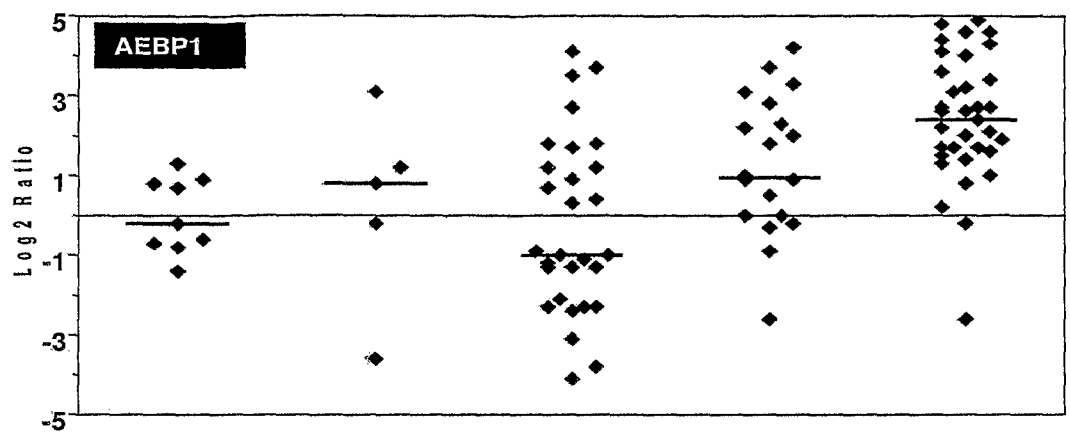
Figure 4B:
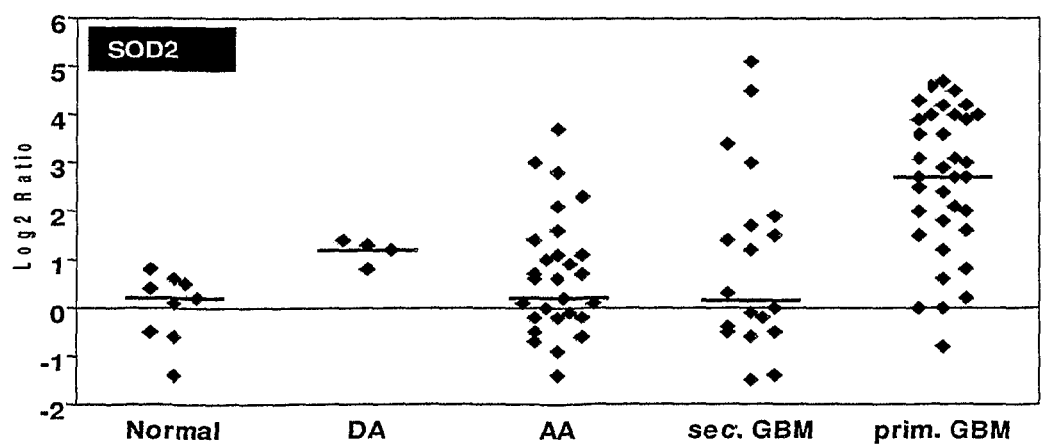

Log 2-transformed gene expression ratios obtained from real-time quantitative PCR analysis are plotted for AEBP1 i.e FIG. 4A and SOD2 i.e FIG. 4B. Each dot represents a data derived from one sample. Horizontal bar represents the median log 2 ratio of the corresponding group.

FIG. 5(Q-T). Immunohistochemical validation of IGFBP7.

Representative micrographs showing IGFBP-7 staining in diffusely infiltrating astrocytomas (DA, AA, s/p GBM). This isoform shows staining in malignant astrocytomas (AA, GBM). IGFBP-7 staining is shown in panels Q, R, S and T. A few tumor cells are labeled in DA (Q). Gradual increase in the number of labeled cells is seen in AA (R), secondary GBM (S), primary GBM (T).

FIG. 6(E-H). Immunohistochemical validation of IGFBP3.

Representative micrographs showing IGFBP-3 staining in diffusely infiltrating astrocytomas (DA, AA, s/p GBM). This isoform shows maximal staining pattern in GBMs. IGFBP-3 staining is shown in panels E, F, G and H. A moderate number of tumor cells show cytoplasmic staining in DA (E) and AA (F) while secondary GBM (G) and primary GBM (H) show strong (3+) cytoplasmic staining of several tumor cells.

FIG. 7(A-E). Immunohistochemical validation of GADD45A.

Immuno-histochemical validation of GADD45A overexpression in glioblastoma. Sections from normal brain—negative for staining (A), DA—negative for staining (B), AA—negative for staining (C), secondary GBMs—positive for staining (D); Primary GBM—positive for staining (E) were stained for GADD45A.

FIG. 8(A-E). Immunohistochemical validation of FSTL1.

Immunohistochemical validation of FSTL1 overexpression in glioblastoma. Sections from normal brain—negative for staining (A), DA—negative for staining (B), AA—negative for staining (C), secondary—positive for staining GBMs (D); Primary GBMs—positive for staining (E) were stained for FSTL1.

FIG. 9(A-E). Immunohistochemical validation of B2M.

Immunohistochemical validation of B2M overexpression in glioblastoma. Sections from normal brain-whitematter (A), DA (B) and AA (C) are negatively stained for B2M while Secondary GBM (D) and Primary GBM (E, F) are positively stained. Note that few parenchymal venules in normal brain (A) and in DA (B) are faintly labeled.

FIG. 10. Immunohistochemical validation of PBEF1.

Sections from normal brain—negative for staining (A), DA—negative for staining (B), AA—negative for staining (C), AA—positive for staining (D), GBMs—positive for staining (E and F) were stained for PBEF1

FIG. 11. PBEF1 expression and survival of patients with GBM.

Kaplan-Meier survival estimates for 51 GBM patients are calculated for p53, EGFR1 and PBEF1 staining. (A) Survival curves for the groups positive and negative for PBEF1 in univariate analysis. The cases which are positive for PBEF1 (red line) had a poorer survival than the cases which were negative (green line) (P=0.16), (B) Survival curves for the groups positive and negative for co-expression of p53 and PBEF1, in multivariate analysis. The group positive for both the markers (red line) had a poor survival as compared to the group negative for both or either of them (green line).

EXAMPLES

The following examples are given by way of illustration of the present invention and therefore should not be construed to limit the scope of the present invention.

Example 1

Tissue Collection

Astrocytoma tissue samples were collected from patients, who underwent surgery at Sri Satya Sai Institute of Higher Medical Sciences and Manipal Hospital, Bangalore, India at the time of surgical resection. Controls comprised non-tumrous brain tissue samples (temporal lobe) collected from patients who underwent surgery for intractable epilepsy. A total of thirty-seven astrocytoma samples of different grades were used in this study. Tissues were bisected and one half was snap-frozen in liquid nitrogen and stored at −80° C. until RNA isolation. The other half was fixed in formalin and processed for paraffin sections and these were used to identify the histopathological grade and the type of astrocytoma.

Example 2

RNA Isolation

Total RNA was extracted from the frozen tissue by a combination of the TRIzol method (Invitrogen, USA) and RNeasy Midi kit (Qiagen) according to the manufacturer's instructions. The RNA samples were quantified by measuring the absorbance using a spectrophotometer and visualized on a MOPS-Formaldehyde gel for quantity and quality assurance.

Example 3

Quantitative RT-PCR

The relative quantitation of expression levels of selected genes was carried out using a two-step strategy: in the first step, cDNA was generated from RNA derived from different tissue samples using the High-capacity cDNA archive kit (ABI PRISM); subsequently real-time quantitative PCR was carried out with the cDNA as template using the following gene-specific primer sets and DyNAmo HS SYBR Green qPCR kit (Finnzymes, Finland): All the primers used were designed using the Primer Express software Version 2.0.0 from Applied Biosystems.

The list of primer pairs is given below.

| Sl. NO: | Gene | Forward Primer (5' to 3') | Reverse Primer (5' to 3') |
|---|---|---|---|
| 1 | SYT1 | GGTTGGCTGTTTCCCAGTAAAAC | TTTTAAGAAGTACGGACCATCGG |
| 2 | RAB26 | GTCTGCTGGTGCGATTCAAG | GCATGGGTAACACTGCGGA |
| 3 | DIRAS2 | CTGGTGTTGAGGTTTGTGAAAGG | CCGTCGTGTCGGTGATCTG |
| 4 | RAB13 | ATAACTACTGCCTACTACCGTGG | CCATGTCACATTTGTTCCCCAG |
| 5 | IGFBP7 | GGTCCTTCCATAGTGACGCC | TCTGAATGGCCAGGTTGTCC |
| 6 | COL6A1 | ACAGTGACGAGGTGGAGATCA | GATAGCGCAGTCGGTGTAGG |
| 7 | DCN | AGTTGGAACGACTTTATCTGTCC | GTGCCCAGTTCTATGACAATCA |
| 8 | PLAT | ACTGCCGGAATCCTGATGG | TGTGCTTGGCAAAGATGGC |
| 9 | LGALS3 | TGCTGATAACAATTCTGGGCAC | TGAAGCGTGGGTTAAAGTGGA |
| 10 | FABP7 | CTCTCAGCACATTCAAGAACACG | GCGAACAGCAACCACATCAC |
| 11 | LOX | CAGGGTGCTGCTCAGATTTCC | GGTAATGTTGATGACAACTGTGC |
| 12 | LAMB1 | ACAAGCCCGAACCCTACTGTA | GACCACATTTTCAATGAGATGGC |
| 13 | IGFBP3 | AGAGCACAGATACCCAGAACT | TGAGGAACTTCAGGTGATTCAGT |
| 14 | GADD45A | GAGAGCAGAAGACCGAAAGGA | CACAACACCACGTTATCGGG |
| 15 | FSTL1 | CAACCACTGTGAACTGCATCG | CCTTTAGAGAACCAGCCATCTG |
| 16 | RHOC | CCTGCCTCCTCATCGTCTTC | AGCACATGAGGATGACATCAGTG |
| 17 | AEBP1 | AAAGGGCGAGGAGTTGGAG | GAGGCTCGGATCTGGTTGT |
| 18 | B2M | AGGCTATCCAGCGTACTCCAA | AATGCGGCATCTTCAAACC |
| 19 | SOD2 | AACCTCAGCCCTAACGGTG | AGCAGCAATTTGTAAGTGTCCC |
| 20 | PBEF1 | ATTGCCTTCGGTTCTGGTGG | CGGCCCTTTTTGGACCTTTTG |

Real-time quantitative PCR was carried out in ABI PRISM 7900 (Applied Biosystems) sequence detection system with the cDNA as template using gene specific primer sets and Dynamo kit containing SYBR green dye (Finnzyme, Finland). All measurements were made in triplicate. The genes RPL35A (ribosomal protein L35a), AGPAT1 (1-acylglycerol-3-phosphate O-acyltransferase 1), ATP5G1 (ATP synthase, H+ transporting, mitochondrial F0 complex, subunit C1 (subunit 9)) and GARS (glycyl-tRNA synthetase) were used as internal controls as their expression levels were found to be unaltered in the array experiments. Normal brain tissue samples from nine different epilepsy patients were used as reference. For each sample, fold change in gene expression is calculated over its mean expression in normal brain sample. Statistical significance was tested by Mann-Whitney test using GraphPad PRISM® software. For each gene, depending on its expression, a suitable threshold fold change was used to calculate the percentage of regulated samples.

Example 4

Histopathology and Immunohistochemistry (IHC)

Histological sections of normal brain and tumor tissues were examined by light microscopy using hematoxylin and eosin (H&E) preparation. Tumor sections of diffusely infiltrating astrocytomas were graded using the WHO grading scheme (11). Paraffin sections (4 µm) from the tumor tissue and controls were collected on silane coated slides for IHC. The primary antibodies used are as follows: 1. IGFBP7 (H-102, SC-3095, diluted to 1:25); 2. IGFBP3 (H-98, SC-9028, diluted to 1:50); 3. GADD45A (Santa cruz, clone C-20, rabbit polyclonal-1:50 dilution); 4. F STL1 (Rabbit polyclonal antibody against purified GST-FSTL1, 1:100 dilution); 5. B2M (Santa cruz, mouse monoclonal, 1:50 dilution); 6. PBEF1 (Rabbit polyclonal antibody against purified GST-PBEF1; 1:1000 dilution). Microwave antigen retrieval was done at 400 watt for 18 minutes in 10 mM citrate buffer, pH 6.0. The antibodies used mainly for the purpose of sub-classifying GBM cases were p53 (monoclonal: DO-7, Biogenix-USA, diluted to 1:200) and EGFR (monoclonal: E-30, Biogenix-USA, diluted to 1:50). For p53, antigen retrieval was performed by heat treatment of the deparaffinized sections in a microwave oven for 25-35 minutes at 700 W in citrate buffer (10 mM, Ph 6.0). For EGFR staining, the sections were pre-treated with Tris-EDTA pH9.0 at 600 W for 30 minutes. All sections were further treated with methanol and 5% hydrogen peroxide to block endogenous peroxidase followed by washes with PBS buffer (pH 7.6). Skimmed milk powder (5%) was used to block background staining for 45 minutes. The sections were incubated with the primary antibody overnight at 4° C. This was followed by incubation with super-sensitive non-biotin HRP detection system (QD440-XAK, Biogenex). "3,3'-Diaminobenzidine" (Sigma) was used as the chromogenic substrate.

Brain tumor samples previously characterized for over-expression of p53 and EGFR were used as positive controls. p53 and EGFR immunoreactivity was considered positive when more than 20% of tumor cells stained positively (nuclear and membrane cytoplasmic labeling respectively). GBMs were classified as primary and secondary, taking into consideration the clinical profile of patients, expression of EGFR and p53 (5). The mean age of patients with primary GBM was 50.6 years and mean duration of symptoms was 2.7 months. Uniform staining for EGFR was evident in all cases and five revealed additionally p53 expression. Among secondary GBMs, the mean age of the patients was 33.8 years and mean duration of symptoms was 5.3 months. p53 immunoreactivity was uniformly evident in all cases and two revealed additionally EGFR over-expression.

ADVANTAGES

The advantages of the present invention are:
1. It provides a useful method for diagnosing the presence of astrocytoma.
2. It provides a useful method for diagnosing the presence of malignant astrocytoma (AA or GBM).
3. It provides a useful method for identifying the type of Glioblastoma—namely primary and secondary.
4. It provides a useful method to determine the prognosis of glioblastoma.
5. The method is useful both before and after clinical symptoms have appeared.
6. The method can also be applied to monitor the effectiveness of anti-cancer treatments.

We claim:

1. A method of identifying and grading glioma in a human subject comprising determining the level of expression of a combination of genes including SYT1, RAB26, DIRAS2, RAB13, IGFBP7, COL6A1, DCN, PLAT, LGALS3, FABP7, LOX, LAMB1, IGFBP3, GADD45A, FSTL1, RHOC, B2M, PBEF1, AEBP1,and SOD2 in a test sample of brain tissue cells obtained from the human subject, wherein the level of expression of said combination of genes is determined by using the primer pairs:

SEQ ID NO: 1 as a Forward Primer of SYT1 gene:
5' GGTTGGCTGTTTCCCAGTAAAAC 3';

SEQ ID NO: 2 as a Reverse Primer of SYT1 gene:
5' TTTTAAGAAGTACGGACCATCGG 3';

SEQ ID NO: 3 as a Forward Primer of RAB26 gene:
5' GTCTGCTGGTGCGATTCAAG 3';

SEQ ID NO: 4 as a Reverse Primer of RAB26 gene:
5' GCATGGGTAACACTGCGGA 3';

SEQ ID NO: 5 as a Forward Primer of DIRAS2 gene:
5' CTGGTGTTGAGGTTTGTGAAAGG 3'

SEQ ID NO: 6 as a Reverse Primer of DIRAS2 gene:
5' CCGTCGTGTCGGTGATCTG 3';

SEQ ID NO: 7 as a Forward Primer of RAB13 gene:
5' ATAACTACTGCCTACTACCGTGG 3';

SEQ ID NO: 8 as a Reverse Primer of RAB13 gene:
5' CCATGTCACATTTGTTCCCCAG 3';

SEQ ID NO: 9 as a Forward Primer of IGFBP7 gene:
5' GGTCCTTCCATAGTGACGCC 3';

SEQ ID No 10 as a Reverse Primer of IGFBP7 gene:
5' TCTGAATGGCCAGGTTGTCC 3';

SEQ ID NO: 11 as a Forward Primer of COL6A1 gene:
5' ACAGTGACGAGGTGGAGATCA 3';

SEQ ID NO: 12 as a Reverse Primer of COL6A1 gene:
5' GATAGCGCAGTCGGTGTAGG 3';

SEQ ID NO: 13 as a Forward Primer of DCN gene:
5' AGTTGGAACGACTTTATCTGTCC 3';

SEQ ID NO: 14 as a Reverse Primer of DCN gene:
5' GTGCCCAGTTCTATGACAATCA 3';

SEQ ID No 15 as a Forward Primer of PLAT gene:
5' ACTGCCGGAATCCTGATGG 3';

SEQ ID No 16. as a Reverse Primer of PALT gene:
5' TGTGCTTGGCAAAGATGGC 3';

SEQ ID NO: 17 as a Forward Primer of LGALS3 gene:
5' TGCTGATAACAATTCTGGGCAC 3';

SEQ ID NO: 18 as a Reverse Primer of LGALS3 gene:
5' TGAAGCGTGGGTTAAAGTGGA 3';

-continued

SEQ ID NO: 19 as a Forward Primer of FABP7 gene:
5' CTCTCAGCACATTCAAGAACACG 3';

SEQ ID NO: 20 as a Reverse Primer of FABP7 gene:
5' GCGAACAGCAACCACATCAC 3';

SEQ ID NO: 21 as a Forward Primer of LOX gene:
5' CAGGGTGCTGCTCAGATTTCC 3';

SEQ ID NO: 22 as a Reverse Primer of LOX gene:
5' GGTAATGTTGATGACAACTGTGC 3';

SEQ ID NO: 23 as a Forward Primer of LAMB1 gene:
5' ACAAGCCCGAACCCTACTGTA 3';

SEQ ID NO: 24 as a Reverse Primer of LAMB1 gene:
5' GACCACATTTTCAATGAGATGGC 3';

SEQ ID NO: 25 as a Forward Primer of IGFBP3 gene:
5' AGAGCACAGATACCCAGAACT 3';

SEQ ID NO: 26 as a Reverse Primer of IGFBP3 gene:
5' TGAGGAACTTCAGGTGATTCAGT 3';

SEQ ID NO: 27 as a Forward Primer of GADD45A gene:
5' GAGAGCAGAAGACCGAAAGGA 3';

SEQ ID NO: 28 as a Reverse Primer of GADD45A gene:
5' CACAACACCACGTTATCGGG 3';

SEQ ID NO: 29 as a Forward'rimer of FSTL1 gene:
5' CAACCACTGTGAACTGCATCG 3';

SEQ ID NO: 30 as a Reverse Primer of FSTL1 gene:
5' CCTTTAGAGAACCAGCCATCTG 3';

SEQ ID NO: 31 as a Forward Primer of RHOC gene:
5' CCTGCCTCCTCATCGTCTTC 3';

SEQ ID NO: 32 as a Reverse Primer of RHOC gene:
5' AGCACATGAGGATGACATCAGTG 3';

SEQ ID NO: 33 as a Forward Primer of AEBP1 gene:
5' AAAGGGCGAGGAGTTGGAG 3';

SEQ ID NO: 34 as a Reverse Primer of AEBP1 gene:
5' GAGGCTCGGATCTGGTTGT 3';

-continued

SEQ ID NO: 35 as a Forward Primer of B2M gene:
5' AGGCTATCCAGCGTACTCCAA 3';

SEQ ID NO: 36 as a Reverse Primer of B2M gene:
5' AATGCGGCATCTTCAAACC 3';

SEQ ID NO: 37 as a Forward Primer of S002 gene:
5' AACCTCAGCCCTAACGGTG 3';

SEQ ID NO: 38 as a Reverse Primer of S002 gene:
5' AGCAGCAATTTGTAAGTGTCCC 3';

SEQ ID NO: 39 as a Forward Primer of PBEF1 gene:
5' ATTGCCTTCGGTTCTGGTGG 3'; and SEQ ID NO: 40 as a Reverse Primer of PBEF1 gene:
5' CGGCCCTTTTTGGACCTTTTG 3'.

2. The method of claim 1, wherein a higher level of expression of RAB13 in the test sample or a lower level of expression of SYT1, RAB26, and/or DIRAS2 in the test sample as compared to a control sample indicates the presence of astrocytoma in the human subject and a higher level of expression of IGFBP7 in the test sample as compared to a control sample indicates the presence of malignant astrocytoma in the human subject.

3. The method of claim 2, wherein a higher level of expression of COL6A1, DCN, PLAT, LGALS3, FABP7, LOX, LAMB1, IGFBP3, GADD45A, FSTL1, RHOC, B2M, and/or PBEF1 in the test sample as compared to a control sample indicates the presence of glioblastoma in the human subject and a higher level of expression of AEBP1 and/or SOD2 in the test sample as compared to a control sample indicates the presence of primary glioblastoma in the human subject and a higher level of expression of PBEF1 in the test sample, as compared to a control sample indicates a poor prognosis for survival of the human subject.

4. The method of claim 1, wherein determining the level of gene expression comprises RT-PCR analysis.

5. The method of claim 1, further comprising detecting the presence or levels of EGFR, p53, and/or Ki-67 proteins.

* * * * *

SEQUENCE LISTING

```
<160> NUMBER OF SEQ ID NOS: 80

<210> SEQ ID NO 1
<211> LENGTH: 23
<212> TYPE: DNA
<213> ORGANISM: Artificial
<220> FEATURE:
<223> OTHER INFORMATION: Synthetic primer

<400> SEQUENCE: 1
ggttggctgt ttcccagtaa aac                                            23

<210> SEQ ID NO 2
<211> LENGTH: 23
<212> TYPE: DNA
<213> ORGANISM: Artificial
<220> FEATURE:
<223> OTHER INFORMATION: Synthetic primer

<400> SEQUENCE: 2
ttttaagaag tacggaccat cgg                                            23

<210> SEQ ID NO 3
<211> LENGTH: 20
<212> TYPE: DNA
<213> ORGANISM: Artificial
<220> FEATURE:
<223> OTHER INFORMATION: Synthetic primer

<400> SEQUENCE: 3
gtctgctggt gcgattcaag                                                20

<210> SEQ ID NO 4
<211> LENGTH: 19
<212> TYPE: DNA
<213> ORGANISM: Artificial
<220> FEATURE:
<223> OTHER INFORMATION: Synthetic primer

<400> SEQUENCE: 4
gcatgggtaa cactgcgga                                                 19

<210> SEQ ID NO 5
```

<211> LENGTH: 23
<212> TYPE: DNA
<213> ORGANISM: Artificial
<220> FEATURE:
<223> OTHER INFORMATION: Synthetic primer

<400> SEQUENCE: 5
ctggtgttga ggtttgtgaa agg    23

<210> SEQ ID NO 6
<211> LENGTH: 19
<212> TYPE: DNA
<213> ORGANISM: Artificial
<220> FEATURE:
<223> OTHER INFORMATION: Synthetic primer

<400> SEQUENCE: 6
ccgtcgtgtc ggtgatctg    19

<210> SEQ ID NO 7
<211> LENGTH: 23
<212> TYPE: DNA
<213> ORGANISM: Artificial
<220> FEATURE:
<223> OTHER INFORMATION: Synthetic primer

<400> SEQUENCE: 7
ataactactg cctactaccg tgg    23

<210> SEQ ID NO 8
<211> LENGTH: 22
<212> TYPE: DNA
<213> ORGANISM: Artificial
<220> FEATURE:
<223> OTHER INFORMATION: Synthetic primer

<400> SEQUENCE: 8
ccatgtcaca tttgttcccc ag    22

<210> SEQ ID NO 9
<211> LENGTH: 20
<212> TYPE: DNA
<213> ORGANISM: Artificial
<220> FEATURE:
<223> OTHER INFORMATION: Synthetic primer

<400> SEQUENCE: 9
ggtccttcca tagtgacgcc    20

<210> SEQ ID NO 10
<211> LENGTH: 20
<212> TYPE: DNA
<213> ORGANISM: Artificial
<220> FEATURE:
<223> OTHER INFORMATION: Synthetic primer

<400> SEQUENCE: 10
tctgaatggc caggttgtcc    20

<210> SEQ ID NO 11
<211> LENGTH: 21
<212> TYPE: DNA
<213> ORGANISM: Artificial
<220> FEATURE:
<223> OTHER INFORMATION: Synthetic primer

<400> SEQUENCE: 11
acagtgacga ggtggagatc a                                                21

<210> SEQ ID NO 12
<211> LENGTH: 20
<212> TYPE: DNA
<213> ORGANISM: Artificial
<220> FEATURE:
<223> OTHER INFORMATION: Synthetic primer

<400> SEQUENCE: 12
gatagcgcag tcggtgtagg                                                  20

<210> SEQ ID NO 13
<211> LENGTH: 23
<212> TYPE: DNA
<213> ORGANISM: Artificial
<220> FEATURE:
<223> OTHER INFORMATION: Synthetic primer

<400> SEQUENCE: 13
agttggaacg actttatctg tcc                                              23

<210> SEQ ID NO 14
<211> LENGTH: 22
<212> TYPE: DNA
<213> ORGANISM: Artificial
<220> FEATURE:
<223> OTHER INFORMATION: Synthetic primer

<400> SEQUENCE: 14
gtgcccagtt ctatgacaat ca                                               22

<210> SEQ ID NO 15
<211> LENGTH: 19
<212> TYPE: DNA
<213> ORGANISM: Artificial
<220> FEATURE:
<223> OTHER INFORMATION: Synthetic primer

<400> SEQUENCE: 15
actgccggaa tcctgatgg                                                   19

<210> SEQ ID NO 16
<211> LENGTH: 19
<212> TYPE: DNA
<213> ORGANISM: Artificial
<220> FEATURE:
<223> OTHER INFORMATION: Synthetic primer

<400> SEQUENCE: 16
tgtgcttggc aaagatggc                                                   19

<210> SEQ ID NO 17
<211> LENGTH: 22
<212> TYPE: DNA
<213> ORGANISM: Artificial
<220> FEATURE:
<223> OTHER INFORMATION: Synthetic primer

<400> SEQUENCE: 17
tgctgataac aattctgggc ac                                               22

<210> SEQ ID NO 18
<211> LENGTH: 21
<212> TYPE: DNA
<213> ORGANISM: Artificial
<220> FEATURE:
<223> OTHER INFORMATION: Synthetic primer

<400> SEQUENCE: 18
tgaagcgtgg gttaaagtgg a                                          21

<210> SEQ ID NO 19
<211> LENGTH: 23
<212> TYPE: DNA
<213> ORGANISM: Artificial
<220> FEATURE:
<223> OTHER INFORMATION: Synthetic primer

<400> SEQUENCE: 19
ctctcagcac attcaagaac acg                                        23

<210> SEQ ID NO 20
<211> LENGTH: 20
<212> TYPE: DNA
<213> ORGANISM: Artificial
<220> FEATURE:
<223> OTHER INFORMATION: Synthetic primer

<400> SEQUENCE: 20
gcgaacagca accacatcac                                            20

<210> SEQ ID NO 21
<211> LENGTH: 21
<212> TYPE: DNA
<213> ORGANISM: Artificial
<220> FEATURE:
<223> OTHER INFORMATION: Synthetic primer

<400> SEQUENCE: 21
cagggtgctg ctcagatttc c                                          21

<210> SEQ ID NO 22
<211> LENGTH: 23
<212> TYPE: DNA
<213> ORGANISM: Artificial
<220> FEATURE:
<223> OTHER INFORMATION: Synthetic primer

<400> SEQUENCE: 22
ggtaatgttg atgacaactg tgc                                        23

<210> SEQ ID NO 23
<211> LENGTH: 21
<212> TYPE: DNA
<213> ORGANISM: Artificial
<220> FEATURE:
<223> OTHER INFORMATION: Synthetic primer

<400> SEQUENCE: 23
acaagcccga accctactgt a                                          21

<210> SEQ ID NO 24
<211> LENGTH: 23
<212> TYPE: DNA
<213> ORGANISM: Artificial
<220> FEATURE:

```
<223> OTHER INFORMATION: Synthetic primer

<400> SEQUENCE: 24
gaccacattt tcaatgagat ggc                                       23

<210> SEQ ID NO 25
<211> LENGTH: 21
<212> TYPE: DNA
<213> ORGANISM: Artificial
<220> FEATURE:
<223> OTHER INFORMATION: Synthetic primer

<400> SEQUENCE: 25
agagcacaga tacccagaac t                                         21

<210> SEQ ID NO 26
<211> LENGTH: 23
<212> TYPE: DNA
<213> ORGANISM: Artificial
<220> FEATURE:
<223> OTHER INFORMATION: Synthetic primer

<400> SEQUENCE: 26
tgaggaactt caggtgattc agt                                       23

<210> SEQ ID NO 27
<211> LENGTH: 21
<212> TYPE: DNA
<213> ORGANISM: Artificial
<220> FEATURE:
<223> OTHER INFORMATION: Synthetic primer

<400> SEQUENCE: 27
gagagcagaa gaccgaaagg a                                         21

<210> SEQ ID NO 28
<211> LENGTH: 20
<212> TYPE: DNA
<213> ORGANISM: Artificial
<220> FEATURE:
<223> OTHER INFORMATION: Synthetic primer

<400> SEQUENCE: 28
cacaacacca cgttatcggg                                           20

<210> SEQ ID NO 29
<211> LENGTH: 21
<212> TYPE: DNA
<213> ORGANISM: Artificial
<220> FEATURE:
<223> OTHER INFORMATION: Synthetic primer

<400> SEQUENCE: 29
caaccactgt gaactgcatc g                                         21

<210> SEQ ID NO 30
<211> LENGTH: 22
<212> TYPE: DNA
<213> ORGANISM: Artificial
<220> FEATURE:
<223> OTHER INFORMATION: Synthetic primer

<400> SEQUENCE: 30
cctttagaga accagccatc tg                                        22
```

```
<210> SEQ ID NO 31
<211> LENGTH: 20
<212> TYPE: DNA
<213> ORGANISM: Artificial
<220> FEATURE:
<223> OTHER INFORMATION: Synthetic primer

<400> SEQUENCE: 31
cctgcctcct catcgtcttc                                               20

<210> SEQ ID NO 32
<211> LENGTH: 23
<212> TYPE: DNA
<213> ORGANISM: Artificial
<220> FEATURE:
<223> OTHER INFORMATION: Synthetic primer

<400> SEQUENCE: 32
agcacatgag gatgacatca gtg                                           23

<210> SEQ ID NO 33
<211> LENGTH: 19
<212> TYPE: DNA
<213> ORGANISM: Artificial
<220> FEATURE:
<223> OTHER INFORMATION: Synthetic primer

<400> SEQUENCE: 33
aaagggcgag gagttggag                                                19

<210> SEQ ID NO 34
<211> LENGTH: 19
<212> TYPE: DNA
<213> ORGANISM: Artificial
<220> FEATURE:
<223> OTHER INFORMATION: Synthetic primer

<400> SEQUENCE: 34
gaggctcgga tctggttgt                                                19

<210> SEQ ID NO 35
<211> LENGTH: 21
<212> TYPE: DNA
<213> ORGANISM: Artificial
<220> FEATURE:
<223> OTHER INFORMATION: Synthetic primer

<400> SEQUENCE: 35
aggctatcca gcgtactcca a                                             21

<210> SEQ ID NO 36
<211> LENGTH: 19
<212> TYPE: DNA
<213> ORGANISM: Artificial
<220> FEATURE:
<223> OTHER INFORMATION: Synthetic primer

<400> SEQUENCE: 36
aatgcggcat cttcaaacc                                                19

<210> SEQ ID NO 37
<211> LENGTH: 19
<212> TYPE: DNA
<213> ORGANISM: Artificial
```

```
<220> FEATURE:
<223> OTHER INFORMATION: Synthetic primer

<400> SEQUENCE: 37
aacctcagcc ctaacggtg                                                19

<210> SEQ ID NO 38
<211> LENGTH: 22
<212> TYPE: DNA
<213> ORGANISM: Artificial
<220> FEATURE:
<223> OTHER INFORMATION: Synthetic primer

<400> SEQUENCE: 38
agcagcaatt tgtaagtgtc cc                                            22

<210> SEQ ID NO 39
<211> LENGTH: 20
<212> TYPE: DNA
<213> ORGANISM: Artificial
<220> FEATURE:
<223> OTHER INFORMATION: Synthetic primer

<400> SEQUENCE: 39
attgccttcg gttctggtgg                                               20

<210> SEQ ID NO 40
<211> LENGTH: 21
<212> TYPE: DNA
<213> ORGANISM: Artificial
<220> FEATURE:
<223> OTHER INFORMATION: Synthetic primer

<400> SEQUENCE: 40
cggccctttt tggaccttt g                                              21

<210> SEQ ID NO 41
<211> LENGTH: 4427
<212> TYPE: DNA
<213> ORGANISM: homo sapiens

<400> SEQUENCE: 41
accaccaaga ataaaatagt tgtttgtccc ctacagtaga acaagtttgc ccattcatcc    60
ttgtgataga tatgcatgca aaaccaaaat gaaatcaaat ccccacagat ggctcgtaag   120
tcaaaaacac tgtttaattc tttcactgca tcccttgggg aagcctggcc cttgaaaaac   180
agaataattc tgaaagaaag aaaacaaaga aaaacatact ccagaattcc taatagaaca   240
cttcacctga acctaaaatg gtgagcgaga gtcaccatga ggccctggca gccccgcctg   300
tcaccactgt cgcgactgtt ctgccaagca acgccacaga gccagccagt cctggagaag   360
gaaaggaaga tgcattttct aagctgaagg agaagtttat gaatgagttg cataaaattc   420
cattgccacc gtgggcctta attgcaatag ccatagtcgc agtccttttta gtcctgacct   480 gctgcttttg tatctgtaag aaatgtttgt tcaaaaagaa aacaagaag aagggaaagg    540 aaaaggagg gaagaatgcc attaacatga agatgtaaaa agacttaggg aagacgatga   600
aagatcaggc cctcaaggat gatgatgctg aaactggatt gacagatgga gaagaaaaag   660
aagaacccaa agaagaggag aaactgggaa aacttcagta ttcactggat tatgatttcc   720
aaaataacca gctgctggta gggatcattc aggctgccga actgcccgcc ttggacatgg   780
ggggcacatc tgatcccttac gtgaaagtgt ttctgctacc tgataagaag aagaaatttg   840
```

```
agacaaaagt ccaccgaaaa acccttaatc ctgtcttcaa tgagcaattt actttcaagg    900
taccatactc ggaattgggt ggcaaaaccc tagtgatggc tgtatatgat tttgatcgtt    960
tctctaagca tgacatcatt ggagaattta aagtccctat gaacacagtg gattttggcc   1020
atgtaactga ggaatggcgt gacctgcaaa gtgctgagaa ggaagagcaa gagaaattgg   1080
gtgatatctg cttctccctt cgctacgtac ctactgctgg taagctgact gttgtcattc   1140
tggaggcaaa gaacctgaag aagatggatg tgggtggctt atccgatcct tatgtgaaga   1200
ttcatctgat gcagaatggt aagaggctga agaagaaaaa gacaacaatt aaaagaaca    1260
cacttaaccc ctactacaat gagtcattca gctttgaagt accttttgaa caaatccaga   1320
aagtgcaggt ggtggtaact gttttggact atgacaagat tggcaagaac gatgccatcg   1380
gcaaagtctt tgtgggctac aacagcaccg gcgcggagct gcgacactgg tcagacatgc   1440
tggccaaccc caggcgacct attgcccagt ggcacaccct gcaggtagag gaggaagttg   1500
atgccatgct ggccgtcaag aagtaaagga agaagaagc ctttctgcat tgcccatat    1560
agtgctcttt agccagtatc tgtaaatacc tcagtaatat gggtcctttc attttccag    1620
ccatgcattc ctaacacaat tcagtggtac ttggaatcct gttttaattt gcacaaattt   1680
aaaatgtagag agccctaag tccttcatca taccactgcc ctccaaatct actcttcttt   1740
taagcaatat gatgtgtaga tagagcatga atgaaattat ttattgtatc acactgttgt   1800
atataccagt atgctaaaga tttatttcta gtttgtgtat ttgtatgttg taagcgtttc   1860
ctaatctgtg tatatctaga tgtttttaat aagatgttct attttaaact atgtaaattg   1920
actgagatat aggagagctg ataatatatt atacggtaaa tatagtatcg tctgcattcc   1980
agcaaaaata tcaactcgta aggcactagt acagttaaac tgacatctta aaggacaact   2040
taaacctgag ctttctattg aatcatttga gtaccaagat aaacttacac cacatacttg   2100
gtgggtgaat ccaattttgt agaattccta cacaggcaaa atagcatgat ctgagcagca   2160
gcatccaggc tgacctcaag gaagcatagc cacaaaacag aatagcacct gtctgtacat   2220
atttacaaag ctaaataat ggcttcactc ttatatttga ggaagcaact gaacaggagt    2280
caatgatttc atattactgc atatagaata acaacaaggt gttccgtgtg tgtgtgtgtg   2340
tgtgtgtgtg tgtgtgtgtg cacatttgtt tggggatggg ggagaagaag ctaaggggag   2400
aagtcaacat ttatgaaata ttgcctgact attttaaaag aaaaaagtag ctctccatta   2460
tcacctttat acaaaatgta catcctgtga attctgttcc agatttcaca cctacaataa   2520
ttccaaaagg tttgcacatt agagtttgta acaaaatatt ttattatata aaaccaggtt   2580
agaaggaatg caggatattt ttaacacaac aatctgtgct tattacacaa aattactttg   2640
tggtaaacag acagtattgt aatcccatca aagatgaaa gaaaacaaa acaaaaaacc    2700
aacaacaatt agccatagtt ctgaatgcac ttcaattaag ccaaaacaga cagctagtga   2760
tcttttttata tgctctttttt acttaagttt taatttgtcc tttaaaaaaa ggtgaaacaa   2820
accaagaaca agttctagaa aactgaagca acctcttatg tatactagat gcttgattta   2880
ggaggagttt ttaaacgttt tcaatgttat tatgtagtaa atgacactat tatgaagcta   2940
ctagtcattc cataagagtc ttaaaggact gctctgtgta acactgtgac tgccgtgtgt   3000
gcttagaccc gtagtttcct cagtggatag cactcaattt attccgtagt gatattgtaa   3060
caatactgcc attcccttct actgcactgc ccaaggtgtg tgtagcacaa acagttctca   3120
ttacaaagga ccaattcaga actgaaaagc tatgcatagg acaaggaaga tacatagaat   3180
ggggtggaac acagcatttt gtcaagcact gtgcaatatt ccatattttt ccccactatg   3240
```

```
gtagacaacc atttcgtgga agggcagcct attatcccac actgcatcta gccttttgtc    3300
ccattcactt ctgtgatcca ttttaatttc caggccacaa gacagtagtg atgctctgaa    3360
atgaaagttt gtcttcacaa atatcaaaac aaaatggagg aaaactaagc attggcctca    3420
tgttcagtct tcaggatatc acaccacgtc ttttcaaaaa ctaaagagaa ttcaaaaagg    3480
gctgatggta ggctttgaac atggggttgg ctgtttccca gtaaaactgg aattcctgtc    3540
gttactgttt ccttatcaaa gaaggggcaa gctcttttgc cttttaggcc agacatagca    3600
aacgctttat aattggcata gacataaagg ataaaggaa ataaccgtc tgccgatggt    3660 ccgtacttct taaaaaacat aggtaataga aaatatacac aagtcagaat gtgaaattaa    3720
ataatggttt gaacagaaaa ttcaaacaag actctttcca atttaaaggg ccaaaccccta    3780 ccaaagagag ggagttgact ggcttttaaa aagtatttaa ataccacaaa tgacatttaa    3840
tttcactgta ttcagcttta agttgttcac aatgaaacca cactttcaaa caagcaggtt    3900
caagctgctg aatagacatt atttcttgca ttaaaatacc actaatgcat tctcttgcaa    3960
cactgccaga catgggattg tcaccataga attagttggt actatgccat ctttcactct    4020
ttcacaagtc agtgatggaa cctgctttat gaccaagatt catcctcaaa taagccacat    4080
gtacccttct gacaaagctg tgtaaagtat tagaatctga tgctctagaa agatcctagt    4140
tgcctttgtg tatatttact gcctgcttga gtgtttctat gtgtgggttt tccctgtatc    4200
ttgtagaaat gttggggtgt tttcctctgc catatggctc gtggcctgcg agccaactat    4260
ttcagctgta ttttaccttc attttttgatg aggtgattta aattttgttt cacttttgtgt    4320 agtgaattcc acagtagttt tctgattgtt gttaaaaatg acttaacata ttacacagat    4380
attcaataaa aatgttttat ttcctgttga aaaaaaaaaa aaaaaaa                  4427

<210> SEQ ID NO 42
<211> LENGTH: 171
<212> TYPE: DNA
<213> ORGANISM: Homo sapiens

<400> SEQUENCE: 42
ggttggctgt ttcccagtaa aactggaatt cctgtcgtta ctgtttcctt atcaaagaag      60
gggcaagctc ttttgccttt taggccagac atagcaaacg ctttataatt ggcatagaca     120
taaaggataa aaggaaaata accgtctgcc gatggtccgt acttcttaaa a              171

<210> SEQ ID NO 43
<211> LENGTH: 1641
<212> TYPE: DNA
<213> ORGANISM: Homo sapiens

<400> SEQUENCE: 43
gccgccgccg ccgccgccgc cgccgccgcc gccaggggaa gggttcgggt ccgggtcggg      60
ctcggcgggc gcggggtgcg ggacggccca gggcacggcg gctgcagcgg gagcacactg     120
agcgcccgcc cgccatgtcc aggaagaaga cccccaagag caagggggcc agcaccccccg    180 ctgcctccac gctgcccacc gccaacgggg cccgaccggc gcgctccggg actgcgcttt     240
ccggccccga cgcgccgccc aacgggccct tgcagcccgg ccggccctcg cttggcggcg     300
gtgtcgactt ctacgacgtc gccttcaagg tcatgctggt gggggactcg ggtgtgggga     360
agacctgtct gctggtgcga ttcaaggatg gtgcttccct ggcggggacc ttcatctcca     420
ccgtaggcat tgacttccgg aacaaagttc tggacgtgga tggtgtgaag gtgaagctgc     480
```

| | |
|---|---|
| agatgtggga cacagctggt caggagcggt tccgcagtgt acccatgcc tactaccggg | 540 |
| atgctcatgc tctgctgctg ctctacgatg tcaccaacaa ggcctccttt gacaacatcc | 600 |
| aggcctggct gaccgagatc cacgagtacg cccagcacga cgtggcgctc atgctgctgg | 660 |
| ggaacaaggt ggactctgcc catgagcgtg tggtgaagag ggaggacggg gagaagctgg | 720 |
| ccaaggagta tggactgccc ttcatggaga ccagcgccaa gacgggcctc aacgtggact | 780 |
| tggccttcac agccatagca aaggagttga agcagcgctc catgaaggct cccagcgagc | 840 |
| cgcgcttccg gctgcatgat tacgttaaga gggagggtcg aggggcctcc tgctgccgcc | 900 |
| cttgaacctg gctgagctca gtcctctgga ggaagccgcc cagtccctag aaggctggac | 960 |
| agagggtctc caggcccttc tgactttgtt gcccagtggc caacgcccga gtgtctgttt | 1020 |
| tcaggagccc caggtcaagc cttgtccctt cctcctccca gcaacagtcc caacaagcag | 1080 |
| gcttctgaga gcccgtggcc gcacactggc cgccacggaa aagcagtctt ctgcacggga | 1140 |
| cggggagcgg caagtggaca gactttgcca cggtgctctg ctgcccctc ctgggcacgt | 1200 |
| ccaggtgagg gagggctggg gctggcacca cgcacagtgc ctaaccctag aaaagccatg | 1260 |
| tcttcagccg cacatgctca ggcagctaag ggaggacgcc tgcccacgcc tgggacagaa | 1320 |
| ggcttcactc ctaatcacat cgtgcatctg tgtgtcctgg gagctgcctg ctcccggccc | 1380 |
| accctctagg aggctctggc tcaaacagca tagggtctt cctcactgac cttggaggat | 1440 |
| gcctgtggcc ttgtgataaa atgtgggaaa tcacagaaaa caccagaaac aacaactgcc | 1500 |
| agcccggcct ggccacaggt gaggtctgtg atttccgagc acgctccacc ttgcactcaa | 1560 |
| cttggccttt tgattgcaca agcctttgtt ttcagtccta gtgaataaag ttgtgttttc | 1620 |
| tggaaaaaaa aaaaaaaaa a | 1641 |

<210> SEQ ID NO 44
<211> LENGTH: 163
<212> TYPE: DNA
<213> ORGANISM: Homo sapiens

<400> SEQUENCE: 44

| | |
|---|---|
| gtctgctggt gcgattcaag gatggtgctt tcctggcggg gaccttcatc tccaccgtag | 60 |
| gcattgactt ccggaacaaa gttctggacg tggatggtgt gaaggtgaag ctgcagatgt | 120 |
| gggacacagc tggtcaggag cggttccgca gtgttaccca tgc | 163 |

<210> SEQ ID NO 45
<211> LENGTH: 4107
<212> TYPE: DNA
<213> ORGANISM: Homo sapiens

<400> SEQUENCE: 45

| | |
|---|---|
| acacaccctg cgctgccctg tcctgcgcga gtggagctct gaagaagctc tgagcggagt | 60 |
| tgtgttcttc cccaggtgcg tcctggctga gagttggagc tctccagcaa catgcctgag | 120 |
| cagagtaacg attaccgggt ggccgtgttt ggggctggcg tgttggcaa gagctccctg | 180 |
| gtgttgaggt ttgtgaaagg cacattccgg gagagctaca tcccgacggt ggaagacacc | 240 |
| taccggcaag tgatcagctg tgacaagagc atatgcacat tgcagatcac cgacacgacg | 300 |
| gggagccacc agttcccggc catgcagcgg ctgtccatct ccaaagggca cgccttcatc | 360 |
| ctggtgtact ccattaccag ccgacagtcc ttggaggagc tcaagcccat ctacgaacaa | 420 |
| atctgcgaga tcaaggggga cgtggagagc atccccatca tgctggtggg gaacaagtgt | 480 |
| gatgagagcc ccagccgcga ggtgcagagc agcgaggcgg aggccttggc ccgcacatgg | 540 |

```
aagtgtgcct tcatggagac ctcagccaag ctcaaccata acgtgaagga gcttttccag    600
gagctgctca acctggagaa gcgcaggacc gtgagtctcc agatcgacgg gaaaaagagc    660
aagcagcaga aaaggaaaga gaagctcaaa ggcaagtgcg tgatcatgtg aaggcccttc    720
ctgcgggagg agcagctgtg tgtccccggc acctcactcc cccaaaatga cacccaccgt    780
cgtcagggta gcatgtataa tgcccacgtg ttaaacattg catttaatcg agatgcgtcc    840
tattgtcctt aagagggcgt ttcacaccac caacagtaag ccaccactc tggagtcaca     900 gaatctgcca ggcggttcaa gtgaaaacca acacactcag catccctggg aactgagagg    960
tgccagcaat tgctgaaggt ggcgatgaac acccgaaggt gggagggagg actggtaccc   1020
acaaagcaac atgtaccgag aggactaaat gtcatctacg tgcatgtgag agcgtgttaa   1080
cctagagtta cctgcaccaa ccccagacag aagccaatca catctttggg ggaggggagg   1140
ggcaggaaga ggtgagaaga tcagatggtc caaagtggac cacacttggt ccattttaca   1200 ctttttttaaa ggggattaaa aaacacagcc tctcccccaa agggtgtccg ttcttaattc   1260
ccacctggcc tgttaggagc cttgctaccc tgagggatg tgttcacctt acctagacct    1320
agttaggaag tatcatttta agctattaga gtatttatct tcatgtgcag ggataagtgc   1380
actaacagtg tgctgctctg tcggaagttc ttcagttttt aagtgaggat atcgtgacag   1440
tattaaaaca tcgcaataat gttcctgtgt gttatacatc gagggtttta gaaatgtgat   1500
tttcttcttt tgacctgtga ggagtataac ttctttcagc cctcagattt taaatacaag   1560
caaataaact cactattttt agacgttttt ttcctccaag gtggttttct tctcttaaat   1620
aactcgatct gtacccagct gggtagcagc cagcaaaggc catcagacaa ccagaagcac   1680
atccattttt gtagtgtcac aaacatgtat atgccacact ttgcacctta atgaaatact   1740
ttgaaacaga agttattcac tgtgttttg atgatctatc tgtattggaa atatgttcct    1800
ggaaaatgca tttaaataat agtaaattct cttgcatgtt ccattatacg tgtcttctaa   1860
gagctgttca atacagtatt cactctagaa acaattatct ttttctctta atgatttttgt  1920 gtgcatcttt aatcttttcaa gccaaattac agctatttca ggtttcctgt gttagcttgg  1980
ggataggatg gtggctggag acaggcaggc ttctctgccc tgggaagagc ccactcagct   2040
taattgctct gccatcgtag agcctggttg gacttggctt cctgaaaact cccactgata   2100
gtgcctgtta gatctcctgt ttgtttcagt tggcagaaca tttactggcc caactgtgg    2160 catcatcctc tcagcagtct tcctgtcacc cgcctggcag gcagaaggag ctgcagtcct   2220
acgtgggcct gcctggggggg gtgggggctg catggctgtt gggtggcagt gtcagcacag   2280
ggagggctta agttggggat gtttgaccag gccacctcct gcaactgctg tttctcctgt   2340
ccctcctatg cagggcttgc agcagcagca gtgtggccat ctccatcccc caaagcacac   2400
ttgctctctc aatatgtcct agttttcttc agccttttct ggttcagttc ccttgtcctg   2460
atctcatcct ctctggtctc ccaataactc acccttggga tgtgtttaga gcgtgggagg   2520
tgcctttgag aactgcttga ctccatgatc tcctagaaca aaaccgccct gactttacag   2580
ggggaacact catgctgagc tgagaaagca gagaagtggc gtgggagcca gctgggggtg   2640
aagagcattt gggccagtcc cgtggccccc ttcagattcc tcaagcagga ttgttctgtt   2700
ctaaaaagct gttgcacagc attcgcaatg agatctttag ttggcggatt ttctggaaca   2760 tttgttttc aacttgtccc gacatttttt ttctgtttct attctgagag agagatgatc    2820
aagttttaat ttgggtatag gttaaatgga agaagaaaca gaacttcatg gccaaagtag   2880
```

| | |
|---|---:|
| acctatagat tttgattggg ttctttgtta acagtagaat gcgatctttg ccactgactg | 2940 |
| tagtattaat aaggttttaa tgtgagatat tcctgcaaac catcccattt ctactgattg | 3000 |
| taagtcagaa tttcttttat cccttcaaa tcagtttcta catgtttaag tgttcagggc | 3060 |
| ttcatcagca tgagaagttt gtaattactg aaagtctgat ttcattcagg acacattttt | 3120 |
| tccttcatat ttttctgtg aatttatagg ctaggaaggc tattgaagcc tcaattatgg | 3180 |
| gtcttcattt tgagatcgtt ttctatgagc tgaactgagg atatcaatgg ttatctcaaa | 3240 |
| atcgtctttt aggagatccc caattgactc agagtttgag gagttagtat cacagaatta | 3300 |
| gatttttta aagcatttgt acgtttccat tcccaaatat gtagctgtgg ttcttgaaaa | 3360 |
| cacatcctac attgcatatg ggcatagcag ttttgaccc aggcagaata agttaatatt | 3420 |
| taattaaata ttgctttgaa gatggcgctc tgggcatgag catggggctc catgacttcc | 3480 |
| cttctatccc catgagcccc tcctccatcc agcgacaagc catgggcatg catacaatgc | 3540 |
| agcaagacca acacaagagc aatattgaat tgttcattct atctaaaatt acatgtatat | 3600 |
| aaaatatata atttatcttc ctgcattttt gaagtataaa gtcataaatt gtacatatct | 3660 |
| gtaagctagt atatttgttt cactgtttgt aatatttaag aaatgctcat tctttgtaga | 3720 |
| acaaaaatgt attaaatatt ttaaaaattg ctctgtgata cttaattttt ttccccaaaa | 3780 |
| tttgtaatgt gttgcttcta cataagttct ctggaaatat ctacaactaa taggacacat | 3840 |
| gtaaatcctt gaagacacat cctggaattc atacccacaca aggacagtgt gtatacaaag | 3900 |
| tatttgcaga gcatgacttt tatatgtgtg ggatatcaat gtgtatattt atatttaaag | 3960 |
| tgtatttatt gttacaagtc tattctctat tatattttat ttactctgcg gttataaaaa | 4020 |
| tcacccttgc atacaagttt ctagttgcca gtgatgttct ggaaataatg ggagatatta | 4080 |
| caataaagct acagttatga caccctg | 4107 |

```
<210> SEQ ID NO 46
<211> LENGTH: 124
<212> TYPE: DNA
<213> ORGANISM: Homo sapiens

<400> SEQUENCE: 46
```

| | |
|---|---:|
| ctggtgttga ggtttgtgaa aggcacattc cgggagagct acatcccgac ggtggaagac | 60 |
| acctaccggc aagtgatcag ctgtgacaag agcatatgca cattgcagat caccgacacg | 120 |
| acgg | 124 |

```
<210> SEQ ID NO 47
<211> LENGTH: 1211
<212> TYPE: DNA
<213> ORGANISM: Homo sapiens

<400> SEQUENCE: 47
```

| | |
|---|---:|
| ctgggctccg tgccgctctg tttgccaacc gtccagtccc gcctaccagt gccgggcgct | 60 |
| ccccacccct ccccccggctc ccccggtgtc cgccatggcc aaagcctacg accacctctt | 120 |
| caagttgctg ctgatcgggg actcgggggt gggcaagact tgtctgatca ttcgctttgc | 180 |
| agaggacaac ttcaacaaca cttacatctc caccatcgga attgatttca gatccgcac | 240 |
| tgtggatata gaggggaaga gatcaaaact acaagtctgg gacacggctg ccaagagcg | 300 |
| gttcaagaca ataactactg cctactaccg tggagccatg ggcattatcc tagtatacga | 360 |
| catcacggat gagaaatctt tcgagaatat tcagaactgg atgaaaagca tcaaggagaa | 420 |
| tgcctcggct ggggtggagc gcctcttgct ggggaacaaa tgtgacatgg aggccaagag | 480 |

```
gaaggtgcag aaggagcagg ccgataagtt ggctcgagag catggaatcc gattttttcga    540 aactagtgct aaatccagta tgaatgtgga tgaggctttt agttccctgg cccgggacat    600
cttgctcaag tcaggaggcc ggagatcagg aaacggcaac aagcctccca gtactgacct    660
gaaaacttgt gacaagaaga acaccaacaa gtgctccctg gctgaggac cctttcttgc     720 ctccccaccc cggaagctga acctgaggga acaacggca agggagtga gcagggaga      780 aatagcagag gggcttggag ggtcacatag gtagatggta aagagaatga ggagaaaaag    840
gagaaagggg aaaagcagaa aggaaaaaaa ggaagagaga ggaagggaga agggagagga    900
atgaattgag gaagtgaaag aaggcaagga ggtaggaaga gagggaggag gaaaggaagg    960
agagatgcct caggcttcag accttacctg ggttttcagg gcaaacataa atgtaaatac    1020
actgatttat tctgttacta gatcaggttt tagggtcctg caaaaggcta gctcggcact    1080
acactaggga atttgctcct gttctgtcac ttgtcatggt cttctcttggt attaaaggcc    1140 accatttgca caaaaaaaaa aaaaaaaaaa aaaaaaaaaa aaaaaaaaaa aaaaaaaaaa    1200
aaaaaaaaaa a                                                         1211

<210> SEQ ID NO 48
<211> LENGTH: 160
<212> TYPE: DNA
<213> ORGANISM: Homo sapiens

<400> SEQUENCE: 48
ataactactg cctactaccg tggagccatg ggcattatcc tagtatacga catcacggat     60
gagaaatctt tcgagaatat tcagaactgg atgaaaagca tcaaggagaa tgcctcggct    120
ggggtggagc gcctcttgct ggggaacaaa tgtgacatgg                          160

<210> SEQ ID NO 49
<211> LENGTH: 1124
<212> TYPE: DNA
<213> ORGANISM: Homo sapiens

<400> SEQUENCE: 49
gccgctgcca ccgcaccccg ccatggagcg gccgtcgctg cgcgccctgc tcctcggcgc     60
cgctgggctg ctgctcctgc tcctgccccct ctcctcttcc tcctcttcgg acacctgcgg    120
cccctgcgag ccggcctcct gcccgcccct gccccgctg gctgcctgc tgggcgagac      180 ccgcgacgcg tgcggctgct gccctatgtg cgcccgcggc gagggcgagc cgtgcggggg    240
tggcggcgcc ggcaggggggt actgcgcgcc gggcatggag tgcgtgaaga ccgcaagag     300 gcggaagggt aaagccgggg cagcagccgg cggtccgggt gtaagcggcg tgtgcgtgtg    360
caagagccgc tacccggtgt gcggcagcga cggcaccacc tacccgagcg gctgccagct    420
gcgcgccgcc agccagaggg ccgagagccg cggggagaag gccatcaccc aggtcagcaa    480
gggcacctgc gagcaaggtc cttccatagt gacgcccccc aaggacatct ggaatgtcac    540
tggtgcccag gtgtacttga gctgtgaggt catcggaatc ccgacacctg tcctcatctg    600
gaacaaggta aaaagggggtc actatggagt tcaaaggaca gaactcctgc ctggtgaccg    660
ggacaacctg gccattcaga cccggggtgg cccagaaaag catgaagtaa ctggctgggt    720
gctggtatct cctctaagta aggaagatgc tggagaatat gagtgccatg catccaattc    780
ccaaggacag gcttcagcat cagcaaaaat tacagtggtt gatgccttac atgaaatacc    840
agtgaaaaaa ggtgaaggtg ccgagctata aacctccaga atattattag tctgcatggt    900
```

```
taaaagtagt catggataac tacattacct gttcttgcct aataagtttc ttttaatcca      960
atccactaac actttagtta tattcactgg ttttacacag agaaatacaa aataaagatc     1020
acacatcaag actatctaca aaatttatt atatatttac agaagaaaag catgcatatc     1080
attaaacaaa taaatactt tttatcacaa aaaaaaaaaa aaaa                       1124

<210> SEQ ID NO 50
<211> LENGTH: 184
<212> TYPE: DNA
<213> ORGANISM: Homo sapiens

<400> SEQUENCE: 50
ggtccttcca tagtgacgcc ccccaaggac atctggaatg tcactggtgc ccaggtgtac       60
ttgagctgtg aggtcatcgg aatcccgaca cctgtcctca tctggaacaa ggtaaaaagg      120
ggtcactatg gagttcaaag gacagaactc ctgcctggtg accgggacaa cctggccatt      180
caga                                                                   184

<210> SEQ ID NO 51
<211> LENGTH: 4246
<212> TYPE: DNA
<213> ORGANISM: homo sapiens

<400> SEQUENCE: 51
gctctcactc tggctgggag cagaaggcag cctcggtctc tgggcggcgg cggcggccca       60
ctctgccctg gccgcgctgt gtggtgaccg caggccccag acatgagggc ggcccgtgct      120
ctgctgcccc tgctgctgca ggcctgctgg acagccgcgc aggatgagcc ggagaccccg      180
agggccgtgg ccttccagga ctgccccgtg gacctgttct tgtgctggac cacctctgag      240
agcgtggccc tgaggctgaa gccctacggg ccctcgtgg acaaagtcaa gtccttcacc      300
aagcgcttca tcgacaacct gagggacagg tactaccgct gtgaccgaaa cctggtgtgg      360
aacgcaggcg cgctgcacta cagtgacgag gtggagatca tccaaggcct cacgcgcatg      420
cctggcggcc gcgacgcact caaaagcagc gtggacgcgg tcaagtactt tgggaagggc      480
acctacaccg actgcgctat caagaagggg ctggagcagc tcctcgtggg gggctcccac      540
ctgaaggaga ataagtacct gattgtggtg accgacgggc accccctgga gggctacaag      600
gaaccctgtg gggggctgga ggatgctgtg aacgaggcca agcacctggg cgtcaaagtc      660
ttctcggtgg ccatcacacc cgaccacctg agccgcgtc tgagcatcat cgccacggac      720
cacacgtacc ggcgcaactt cacggcggct gactggggcc agagccgcga cgcagaggag      780
gccatcagcc agaccatcga caccatcgtg gacatgatca aaaataacgt ggagcaagtg      840
tgctgctcct tcgaatgcca gcctgcaaga ggacctccgg ggctccgggg cgaccccggc      900
tttgagggag aacgaggcaa gccggggctc ccaggagaga agggagaagc cggagatcct      960
ggaagacccg gggacctcgg acctgttggg taccagggaa tgaagggaga aaaagggagc     1020 cgtgggggaga agggctccag gggacccaag ggctacaagg agagaagggg caagcgtggc     1080
atcgacgggg tggacggcgt gaaggggag atggggtacc caggcctgcc aggctgcaag     1140
ggctcgcccg gtttgacgg cattcaagga ccccctggcc caagggaga ccccggtgcc     1200 tttgactga aggagaaaa gggcgagcct ggagctgacg gggaggcggg gagaccaggg     1260
agctcgggac catctggaga cgagggccag ccgggagagc ctgggcccc cggagagaaa     1320 ggagaggcgg gcgacgaggg gaacccagga cctgacggtg cccccgggga gcggggtggc     1380
cctggagaga gaggaccacg ggggaccca ggcacgcggg gaccaagagg agaccctggt     1440
```

-continued

```
gaagctggcc cgcagggtga tcagggaaga gaaggccccg ttggtgtccc tggagacccg    1500
ggcgaggctg gccctatcgg acctaaaggc taccgaggcg atgagggtcc cccagggtcc    1560
gagggtgcca gaggagcccc aggacctgcc ggaccccctg agacccgggg ctgatgggt     1620 gaaaggggag aagacggccc cgctggaaat ggcaccgagg gcttccccgg cttcccoggg    1680 tatccgggca cagggggcgc tcccgggata acggcacga agggctaccc cggcctcaag     1740
ggggacgagg gagaagccgg ggaccccgga gacgataaca acgacattgc accccgagga    1800
gtcaaaggag caaaggggta ccggggtccc gagggccccc agggaccccc aggacaccaa    1860
ggaccgcctg ggccggacga atgcgagatt ttggacatca tcatgaaaat gtgctcttgc    1920
tgtgaatgca agtgcggccc catcgacctc ctgttcgtgc tggacagctc agagagcatt    1980
ggcctgcaga acttcgagat tgccaaggac ttcgtcgtca aggtcatcga ccggctgagc    2040
cgggacgagc tggtcaagtt cgagccaggg cagtcgtacg cgggtgtggt gcagtacagc    2100
cacagccaga tgcaggagca cgtgagcctg cgcagcccca gcatccggaa cgtgcaggag    2160
ctcaaggaag ccatcaagag cctgcagtgg atggcgggcg gcaccttcac ggggggaggcc   2220 ctgcagtaca cgcgggacca gctgctgccg cccagcccga caaccgcat cgccctggtc     2280 atcactgacg ggcgctcaga cactcagagg gacaccacac cgctcaacgt gctctgcagc    2340
cccggcatcc aggtggtctc cgtgggcatc aaagacgtgt ttgacttcat cccaggctca    2400
gaccagctca atgtcatttc ttgccaaggc ctggcaccat cccagggccg gcccggcctc    2460
tcgctggtca aggagaacta tgcagagctg ctggaggatg ccttcctgaa gaatgtcacc    2520
gcccagatct gcatagacaa gaagtgtcca gattacacct gccccatcac gttctcctcc    2580
ccggctgaca tcaccatcct gctggacggc tccgccagcg tgggcagcca caactttgac    2640
accaccaagc gcttcgccaa cgccctggcc gagcgcttcc tcacagcggg caggacggac    2700
cccgcccacg acgtgcgggt ggcggtggtg cagtacagcg gcacgggcca gcagcgccca    2760
gagcgggcgt cgctgcagtt cctgcagaac tacacggccc tggccagtgc cgtcgatgcc    2820 atggactta tcaacgacgc caccgacgtc aacgatgccc tgggctatgt gacccgcttc    2880
taccgcgagg cctcgtccgg cgctgccaag aagaggctgc tgctcttctc agatggcaac    2940
tcgcagggcg ccacgcccgc tgccatcgag aaggccgtgc aggaagccca gcgggcaggc    3000
atcgagatct tcgtggtggt cgtgggccgc caggtgaatg agccccacat ccgcgtcctg    3060
gtcaccggca agacggccga gtacgacgtg gcctacggcg agagccacct gttccgtgtc    3120
cccagctacc aggccctgct ccgcggtgtc ttccaccaga cagtctccag gaaggtggcg    3180
ctgggctagc ccaccctgca cgccggcacc aaaccctgtc ctcccacccc tccccactca    3240
tcactaaaca gagtaaaatg tgatgcgaat tttcccgacc aacctgattc gctagatttt    3300
ttttaaggaa aagcttggaa agccaggaca caacgctgct gcctgctttg tgcagggtcc    3360 tccgggctc agccctgagt tggcatcacc tgcgcagggc cctctggggc tcagccctga    3420
gctagtgtca cctgcacagg gccctctgag gctcagccct gagctggcgt cacctgtgca    3480
gggccctctg ggctcagcc ctgagctggc ctcacctggg ttccccaccc cgggctctcc    3540
tgccctgccc tcctgcccgc cctccctcct gcctgcgcag ctccttccct aggcacctct   3600
gtgctgcatc ccaccagcct gagcaagacg ccctctcggg gcctgtgccg cactagcctc    3660
cctctcctct gtcccatag ctggttttc ccaccaatcc tcacctaaca gttactttac    3720
aattaaactc aaagcaagct cttctcctca gcttggggca gccattggcc tctgtctcgt    3780
```

```
tttgggaaac caaggtcagg aggccgttgc agacataaat ctcggcgact cggccccgtc   3840
tcctgagggt cctgctggtg accggcctgg accttggccc tacagccctg gaggccgctg   3900
ctgaccagca ctgaccccga cctcagagag tactcgcagg ggcgctggct gcactcaaga   3960
ccctcgagat taacggtgct aaccccgtct gctcctccct cccgcagaga ctggggcctg   4020
gactggacat gagagcccct tggtgccaca gagggctgtg tcttactaga acaacgcaa    4080 acctctcctt cctcagaata gtgatgtgtt cgacgtttta tcaaaggccc cctttctatg   4140
ttcatgttag ttttgctcct tctgtgtttt tttctgaacc atatccatgt tgctgacttt   4200
tccaaataaa ggttttcact cctctaaaaa aaaaaaaaa aaaaaa                   4246

<210> SEQ ID NO 52
<211> LENGTH: 122
<212> TYPE: DNA
<213> ORGANISM: Homo sapiens

<400> SEQUENCE: 52
acagtgacga ggtggagatc atccaaggcc tcacgcgcat gcctggcggc cgcgacgcac     60
tcaaaagcag cgtggacgcg gtcaagtact tgggaaggg cacctacacc gactgcgcta    120
tc                                                                  122

<210> SEQ ID NO 53
<211> LENGTH: 2305
<212> TYPE: DNA
<213> ORGANISM: Homo sapiens

<400> SEQUENCE: 53
gaatctacaa taagacaaat ttcaaatcaa gttgctccac tatactgcat aagcagttta     60
gaatcttaag cagatgcaaa aagaataaag caaatgggga gaaaaaaaag gccgataaag    120
tttctggcta caatacaaga gacatatcat taccatatga tctaatgtgg gtgtcagccg    180
gattgtgttc attgagggaa accttatttt ttaactgtgc tatggagtag aagcaggagg    240
ttttcaacct agtcacagag cagcacctac cccctcctcc tttccacacc tgcaaactct    300
tttacttggg ctgaatattt agtgtaatta catctcagct ttgagggctc ctgtggcaaa    360
ttcccggatt aaaaggttcc ctggttgtga aaatacatga gataaatcat gaaggccact    420
atcatcctcc ttctgcttgc acaagtttcc tgggctggac cgtttcaaca gagaggctta    480
tttgacttta tgctagaaga tgaggcttct gggataggcc cagaagttcc tgatgaccgc    540
gacttcgagc cctccctagg cccagtgtgc cccttccgct gtcaatgcca tcttcgagtg    600
gtccagtgtt ctgatttggg tctggacaaa gtgccaaagg atcttccccc tgacacaact    660
ctgctagacc tgcaaaacaa caaaataacc gaaatcaaag atggagactt taagaacctg    720
aagaaccttc acgcattgat tcttgtcaac aataaaatta gcaaagttag tcctggagca    780
tttacacctt tggtgaagtt ggaacgactt tatctgtcca agaatcagct gaaggaattg    840
ccagaaaaaa tgcccaaaac tcttcaggag ctgcgtgccc atgagaatga gatcaccaaa    900
gtgcgaaaag ttactttcaa tggactgaac cagatgattg tcatagaact gggcaccaat    960
ccgctgaaga gctcaggaat tgaaaatggg gctttccagg gaatgaagaa gctctcctac   1020
atccgcattg ctgataccaa tatcaccagc attcctcaag gtcttcctcc ttcccttacg   1080
gaattacatc ttgatggcaa caaaatcagc agagttgatg cagctagcct gaaaggactg   1140
aataatttgg ctaagttggg attgagtttc aacagcatct ctgctgttga caatggctct   1200
ctggccaaca cgcctcatct gagggagctt cacttggaca acaacaagct taccagagta   1260
```

```
cctggtgggc tggcagagca taagtacatc caggttgtct accttcataa caacaatatc    1320
tctgtagttg gatcaagtga cttctgccca cctggacaca acaccaaaaa ggcttcttat    1380
tcgggtgtga gtcttttcag caacccggtc cagtactggg agatacagcc atccaccttc    1440
agatgtgtct acgtgcgctc tgccattcaa ctcggaaact ataagtaatt ctcaagaaag    1500
ccctcatttt tataacctgg caaaatcttg ttaatgtcat tgctaaaaaa taaataaaag    1560
ctagatactg gaaacctaac tgcaatgtgg atgttttacc cacatgactt attatgcata    1620
aagccaaatt tccagtttaa gtaattgcct acaataaaaa gaaatttttgc ctgccatttt    1680 cagaatcatc ttttgaagct ttctgttgat gttaactgag ctactagaga tattcttatt    1740
tcactaaatg taaaatttgg agtaaatata tatgtcaata tttagtaaag cttttctttt    1800
ttaatttcca ggaaaaaata aaaagagtat gagtcttctg taattcattg agcagttagc    1860
tcatttgaga taaagtcaaa tgccaaacac tagctctgta ttaatcccca tcattactgg    1920
taaagcctca tttgaatgtg tgaattcaat acaggctatg taaaattttt actaatgtca    1980
ttattttgaa aaaataaatt taaaaataca ttcaaaatta ctattgtata caagcttaat    2040
tgttaatatt ccctaaacac aatttttatga agggagaaga cattggtttg ttgacaataa    2100
cagtacatct tttcaagttc tcagctattt cttctacctc tccctatctt acatttgagt    2160
atggtaactt atgtcatcta tgttgaatgt aagcttataa agcacaaagc atacatttcc    2220
tgactggtct agagaactga tgtttcaatt taccctctg ctaaataaat attaaaacta    2280
tcatgtgaaa aaaaaaaaaa aaaaa                                          2305

<210> SEQ ID NO 54
<211> LENGTH: 160
<212> TYPE: DNA
<213> ORGANISM: Homo sapiens

<400> SEQUENCE: 54
agttggaacg actttatctg tccaagaatc agctgaagga attgccagaa aaaatgccca     60
aaactcttca ggagctgcgt gcccatgaga atgagatcac caaagtgcga aaagttactt    120
tcaatggact gaaccagatg attgtcatag aactgggcac                          160

<210> SEQ ID NO 55
<211> LENGTH: 3173
<212> TYPE: DNA
<213> ORGANISM: Homo sapiens

<400> SEQUENCE: 55
atggccctgt ccactgagca tcctcccgcc acacagaaac ccgcccagcc ggggccaccg     60
accccacccc ctgcctggaa acttaaagga ggccggagct gtgggagct cagagctgag    120 atcctacagg agtccagggc tggagagaaa acctctgcga ggaaagggaa ggagcaagcc    180
gtgaatttaa gggacgctgt gaagcaatca tggatgcaat gagagaggg ctctgctgtg    240 tgctgctgct gtgtggagca gtcttcgttt cgcccagcca ggaaatccat gcccgattca    300
gaagaggagc cagatcttac caagtgatct gcagagatga aaaaacgcag atgatatacc    360
agcaacatca gtcatggctg cgccctgtgc tcagaagcaa ccgggtggaa tattgctggt    420
gcaacagtgg cagggcacag tgccactcag tgcctgtcaa agttgcagc gagccaaggt    480 gtttcaacgg gggcacctgc cagcaggccc tgtacttctc agatttcgtg tgccagtgcc    540
ccgaaggatt tgctgggaag tgctgtgaaa tagataccag ggccacgtgc tacgaggacc    600
```

```
agggcatcag ctacaggggc acgtggagca cagcggagag tggcgccgag tgcaccaact    660
ggaacagcag cgcgttggcc cagaagccct acagcgggcg gaggccagac gccatcaggc    720
tgggcctggg gaaccacaac tactgcagaa acccagatcg agactcaaag ccctggtgct    780
acgtctttaa ggcggggaag tacagctcag agttctgcag caccctgcc tgctctgagg     840 gaaacagtga ctgctacttt gggaatgggt cagcctaccg tggcacgcac agcctcaccg    900
agtcgggtgc ctcctgcctc ccgtggaatt ccatgatcct gataggcaag gtttacacag    960
cacagaaccc cagtgcccag gcactgggcc tgggcaaaca taattactgc cggaatcctg   1020
atggggatgc caagccctgg tgccacgtgc tgaagaaccg caggctgacg tgggagtact   1080
gtgatgtgcc ctcctgctcc acctgcggcc tgagacagta cagccagcct cagtttcgca   1140
tcaaaggagg gctcttcgcc gacatcgcct cccacccctg gcaggctgcc atctttgcca   1200
agcacaggag gtcgcccgga gagcggttcc tgtgcggggg catactcatc agctcctgct   1260
ggattctctc tgccgcccac tgcttccagg agaggtttcc gccccaccac ctgacggtga   1320
tcttgggcag aacataccgg gtggtccctg gcgaggagga gcagaaattt gaagtcgaaa   1380
aatacattgt ccataaggaa ttcgatgatg acacttacga caatgacatt gcgctgctgc   1440
agctgaaatc ggattcgtcc cgctgtgccc aggagagcag cgtggtccgc actgtgtgcc   1500
ttcccccggc ggacctgcag ctgccggact ggacggagtg tgagctctcc ggctacggca   1560
agcatgaggc cttgtctcct ttctattcgg agcggctgaa ggaggctcat gtcagactgt   1620
acccatccag ccgctgcaca tcacaacatt tacttaacag aacagtcacc gacaacatgc   1680
tgtgtgctgg agacactcgg agcggcgggc cccaggcaaa cttgcacgac gcctgccagg   1740
gcgattcggg aggccccctg gtgtgtctga cgatggccg catgactttg gtgggcatca    1800
tcagctgggg cctgggctgt ggacagaagg atgtcccggg tgtgtacacc aaggttacca   1860
actacctaga ctggattcgt gacaacatgc gaccgtgacc aggaacaccc gactcctcaa   1920
aagcaaatga gatcccggcc tttcttcttc agaagacact gcaaaggcgc agtgcttctc   1980
tacagacttc tccagaccca ccacaccgca gaagcgggac gagacctac aggagaggga    2040 agagtgcatt ttcccagata cttcccattt tggaagtttt caggacttgg tctgatttca   2100
ggatactctg tcagatggga agacatgaat gcacactagc ctctccagga atgcctcctc   2160
cctgggcaga aagtggccat gccaccctgt tttcagctaa agcccaacct cctgacctgt   2220
caccgtgagc agctttggaa acaggaccac aaaaatgaaa gcatgtctca atagtaaaag   2280
ataacaagat cttctcagga aagacggattg cattagaaat agacagtata tttatagtca   2340
caagagccca gcagggcctc aaagttgggg caggctggct ggcccgtcat gttcctcaaa   2400
agcacccttg acgtcaagtc tccttcccct ttccccactc cctggctctc agaaggtatt   2460 cctttttgtgt acagtgtgta aagtgtaaat cctttttctt tataaacttt agagtagcat   2520
gagagaattg tatcatttga caactaggc ttcagcatat ttatagcaat ccatgttagt    2580
ttttactttc tgttgccaca accctgtttt atactgtact aataaattc agatatattt     2640 ttcacagttt ttccaaaatc agagtggaat ggttttgtta tagatgctgt atcccactct   2700
ttattcatgt tcatttta aaatcatttg gaattctgct tcactcgctt aacatataca     2760
caacacctgt aacatacaag gcaatgggct aggtgctcca gaccgggaaa aggagggaca   2820
ggaatgcttg gtctgatggg ctaatatggc atttagagaa gtaccaaggt acagtggagc   2880
cggtcacaaa agggcagact tgtagtagaa ttcagttgca agagggattg gggaatctta   2940 aggaaaaaaat agaatcttaa ggaaaaaata actgggtgag acgtggactg tggacaggtg   3000
```

```
tggaaaaggc actctccatg gaggtatgaa tatgtagagg gccaagagag gggagtacag    3060
ggagaaatga gttgagcttg tctgaagtga acttcaggaa gaggaacata ggctggaatt    3120
tagattatgg gggctctgaa caccaaactg agtttggact taattgactt ctg           3173
```

<210> SEQ ID NO 56
<211> LENGTH: 201
<212> TYPE: DNA
<213> ORGANISM: Homo sapiens

<400> SEQUENCE: 56

```
actgccggaa tcctgatggg gatgccaagc cctggtgcca cgtgctgaag aaccgcaggc      60
tgacgtggga gtactgtgat gtgccctcct gctccacctg cggcctgaga cagtacagcc    120
agcctcagtt tcgcatcaaa ggagggctct tcgccgacat cgcctcccac ccctggcagg    180
ctgccatctt tgccaagcac a                                              201
```

<210> SEQ ID NO 57
<211> LENGTH: 1080
<212> TYPE: DNA
<213> ORGANISM: Homo sapiens

<400> SEQUENCE: 57

```
ggagaggact ggctgggcag gggcgccgcc ccgcctcggg agaggcgggc cgggcggggc      60
tgggagtatt tgaggctcgg agccaccgcc ccgccggcgc ccgcagcacc tcctcgccag    120
cagccgtccg gagccagcca acgagcgaaa aatggcagac aattttttcgc tccatgatgc    180 gttatctggg tctggaaacc caaaccctca aggatggcct ggcgcatggg ggaaccagcc    240
tgctggggca gggggctacc caggggcttc ctatcctggg gcctaccccg ggcaggcacc    300
cccaggggct tatcctggac aggcacctcc aggcgcctac cctggagcac ctggagctta    360
tcccggagca cctgcacctg gagtctaccc agggccaccc agcggccctg ggcctaccc     420 atcttctgga cagccaagtg ccaccggagc ctaccctgcc actggcccct atggcgcccc    480
tgctgggcca ctgattgtgc cttataacct gcctttgcct gggggagtgg tgcctcgcat    540
gctgataaca attctgggca cggtgaagcc caatgcaaac agaattgctt tagatttcca    600
aagagggaat gatgttgcct tccactttaa cccacgcttc aatgagaaca acaggagagt    660
cattgtttgc aatacaaagc tggataataa ctggggaagg gaagaaagac agtcggtttt    720
cccatttgaa agtgggaaac cattcaaaat acaagtactg gttgaacctg accacttcaa    780
ggttgcagtg aatgatgctc acttgttgca gtacaatcat cgggttaaaa aactcaatga    840
aatcagcaaa ctgggaattt ctggtgacat agacctcacc agtgcttcat ataccatgat    900
ataatctgaa agggcagat taaaaaaaaa aaagaatct aaaccttaca tgtgtaaagg    960
tttcatgttc actgtgagtg aaaatttta cattcatcaa tatccctctt gtaagtcatc    1020
tacttaataa atattacagt gaattacctg tctcaatatg tcaaaaaaaa aaaaaaaaa    1080
```

<210> SEQ ID NO 58
<211> LENGTH: 102
<212> TYPE: DNA
<213> ORGANISM: Homo sapiens

<400> SEQUENCE: 58

```
tgctgataac aattctgggc acggtgaagc ccaatgcaaa cagaattgct ttagatttcc      60
aaagagggaa tgatgttgcc ttccacttta acccacgctt ca                       102
```

<210> SEQ ID NO 59
<211> LENGTH: 1005
<212> TYPE: DNA
<213> ORGANISM: Homo sapiens

<400> SEQUENCE: 59

| | | | | | |
|---|---|---|---|---|---|
| gaggattggg | aggaactcga | cctactccgc | taacccagtg | gcctgagcca | atcacaaaga | 60 |
| ggattggagc | ctcactcgag | cgctccttcc | cttctcctct | ctctgtgaca | gcctcttgga | 120 |
| aagagggaca | ctggaggggt | gtgtttgcaa | tttaaatcac | tggattttg | cccaccctct | 180 |
| ttccaaataa | gaaggcagga | gctgcttgct | gaggtgtaaa | gggtcttctg | agctgcagtg | 240 |
| gcaattagac | cagaagatcc | ccgctcctgt | ctctaaagag | gggaaagggc | aaggatggtg | 300 |
| gaggctttct | gtgctacctg | gaagctgacc | aacagtcaga | actttgatga | gtacatgaag | 360 |
| gctctaggcg | tgggctttgc | cactaggcag | gtgggaaatg | tgaccaaacc | aacggtaatt | 420 |
| atcagtcaag | aaggagacaa | agtggtcatc | aggactctca | gcacattcaa | gaacacggag | 480 |
| attagtttcc | agctgggaga | agagtttgat | gaaaccactg | cagatgatag | aaactgtaag | 540 |
| tctgttgtta | gcctggatgg | agacaaactt | gttcacatac | agaaatggga | tggcaaagaa | 600 |
| acaaattttg | taagagaaat | taaggatggc | aaaatggtta | tgacccttac | ttttggtgat | 660 |
| gtggttgctg | ttcgccacta | tgagaaggca | taaaaatgtt | cctggtcggg | gcttggaaga | 720 |
| gctcttcagt | ttttctgttt | cctcaagtct | cagtgctatc | ctattacaac | atggctgatc | 780 |
| attaattaga | aggttatcct | tggtgtggag | gtggaaatg | tgatttaaa | aacttgttac | 840 |
| tccaagcaac | ttgcccaatt | ttaatctgaa | aatttatcat | gttttataat | ttgaattaaa | 900 |
| gttttgtccc | cccccccctt | tttttataa | acaagtgaat | acattttata | atttcttttg | 960 |
| gaatgtaaat | caaatttgaa | taaaaatctt | acacgtgaaa | aaaaa | | 1005 |

<210> SEQ ID NO 60
<211> LENGTH: 221
<212> TYPE: DNA
<213> ORGANISM: Homo sapiens

<400> SEQUENCE: 60

| | | | | | |
|---|---|---|---|---|---|
| ctctcagcac | attcaagaac | acggagatta | gtttccagct | gggagaagag | tttgatgaaa | 60 |
| ccactgcaga | tgatagaaac | tgtaagtctg | ttgttagcct | ggatggagac | aaacttgttc | 120 |
| acatacagaa | atgggatggc | aaagaaacaa | attttgtaag | agaaattaag | gatggcaaaa | 180 |
| tggttatgac | ccttactttt | ggtgatgtgg | ttgctgttcg | c | | 221 |

<210> SEQ ID NO 61
<211> LENGTH: 3925
<212> TYPE: DNA
<213> ORGANISM: Homo sapiens

<400> SEQUENCE: 61

| | | | | | |
|---|---|---|---|---|---|
| attacgtgaa | caaatagctg | aggggcggcc | gggccagaac | ggcttgtgta | actttgcaaa | 60 |
| cgtgccagaa | agtttaaaat | ctctcctcct | tccttcactc | cagacactgc | ccgctctccg | 120 |
| ggactgccgc | gccgctcccc | gttgccttcc | aggactgaga | aaggggaaag | ggaagggtgc | 180 |
| cacgtccgag | cagccgccct | gactggggaa | gggtctgaat | cccacccttg | gcattgcttg | 240 |
| gtggagactg | agatacccgt | gctccgctcg | cctccttggt | tgaagatttc | tccttccctc | 300 |
| acgtgatttg | agcccgttt | ttattttctg | tgagccacgt | cctcctcgag | cggggtcaat | 360 |
| ctggcaaaag | gagtgatgcg | cttcgcctgg | accgtgctcc | tgctcgggcc | tttgcagctc | 420 |

```
tgcgcgctag tgcactgcgc ccctcccgcc gccggccaac agcagccccc gcgcgagccg    480
ccggcggctc cgggcgcctg gcgccagcag atccaatggg agaacaacgg gcaggtgttc    540
agcttgctga gcctgggctc acagtaccag cctcagcgcc gccgggaccc gggcgccgcc    600
gtccctggtg cagccaacgc ctccgcccag cagccccgca ctccgatcct gctgatccgc    660
gacaaccgca ccgccgcggc gcgaacgcgg acggccggct catctggagt caccgctggc    720
cgccccaggc ccaccgcccg tcactggttc aagctggct  actcgacatc tagagcccgc    780
gaagctggcg cctcgcgcgc ggagaaccag acagcgccgg agaagttcc  tgcgctcagt    840 aacctgcggc cgcccagccg cgtggacggc atggtgggcg acgcccctta caaccccctac   900 aagtactctg acgacaaccc ttattacaac tactacgata cttatgaaag gcccagacct    960
gggggcaggt accggcccgg atacggcact ggctacttcc agtacggtct cccagacctg   1020
gtggccgacc cctactacat ccaggcgtcc acgtacgtgc agaagatgtc catgtacaac   1080
ctgagatgcg cggcggagga aaactgtctg gccagtacag catacagggc agatgtcaga   1140
gattatgatc acagggtgct gctcagattt ccccaaagag tgaaaaacca agggacatca   1200
gatttcttac ccagccgacc aagatattcc tgggaatggc acagttgtca tcaacattac   1260
cacagtatgg atgagtttag ccactatgac ctgcttgatg ccaacaccca gaggagagtg   1320
gctgaaggcc acaaagcaag tttctgtctt gaagacacat cctgtgacta tggctaccac   1380
aggcgatttg catgtactgc acacacacag ggattgagtc ctggctgtta tgatacctat   1440
ggtgcagaca tagactgcca gtggattgat attacagatg taaaacctgg aaactatatc   1500
ctaaaggtca gtgtaaaccc cagctacctg gttcctgaat ctgactatac caacaatgtt   1560
gtgcgctgtg acattcgcta cacaggacat catgcgtatg cctcaggctg cacaatttca   1620
ccgtattaga aggcaaagca aaactcccaa tggataaatc agtgcctggt gttctgaagt   1680
gggaaaaaat agactaactt cagtaggatt tatgtatttt gaaaagaga  acagaaaaca   1740 acaaagaat  ttttgtttgg actgttttca ataacaaagc acataactgg attttgaacg   1800
cttaagtcat cattacttgg gaaatttta  atgtttatta tttacatcac tttgtgaatt   1860
aacacagtgt tcaattctg  taattacata tttgactctt tcaaagaaat ccaaatttct   1920
catgttcctt ttgaaattgt agtgcaaaat ggtcagtatt atctaaatga atgagccaaa   1980
atgactttga actgaaactt ttctaaagtg ctggaacttt agtgaaacat aataataatg   2040
ggtttatata tgtcatagca tagatgaatt tagaaacaat gctcctactg tttaaataca   2100
tatggacaca tctggtgctg agaaagaaac aaacacatta ccattggtgt caagaaatat   2160
tactatatag cagagaaatg gcaatacatg tactcagata gttacatccc tatataaaaa   2220
gtatgtttac atttaaaaaa ttagtagata acttcctttc tttcaagtgc acaatttcat   2280
tttgacttga gtcaactttt gttttggaac aaattaagta agggagctgc ccaatcctgt   2340
ctgatatttc ttgaggctgc cctctatcat tttatctttc ccatgggcag agatgttgta   2400
agtgggattc ttaatatcac cattcttggg actggtatac ataaggcagc cgtgaaactg   2460
gaaagtcatt ttgatgactg atgtgataca tccagaggta aatgcatttt aaacatatta   2520
aagtatttgc caaagataca attttcttgc tgacataaaa atcacacaaa caagtccccc   2580
ccaaaccaca actgtctctc aaatagctta aaaaaattga aaaacatttt aggattttc   2640 aagttttcta gattttaaaa agatgttcag ctattagagg aatgttaaaa atttatatt   2700 atctagaaca caggaacatc atcctgggtt attcaggaat cagtcacaca tgtgtgtgtg   2760
```

```
tctgagatat agtctaaatt agcaaagcac atagtattac atacttgagg ggttggtgaa    2820
caaaggaaaa atatactttc tgcaaaacca aggactgtgc tgcgtaatga dacagctgtg    2880
atttcatttg aaactgtgaa accatgtgcc ataatagaat tttgagaatt ttgcttttac    2940
ctaaattcaa gaaaatgaaa ttacactttt aagttagtgg tgcttaagca taattttttcc   3000 tatattaacc agtattaaaa tctcaagtaa gattttccag tgccagaaca tgttaggtgg    3060
aattttaaaa gtgcctcggc atcctgtatt acatgtcata gaattgtaaa gtcaacatca    3120
attactagta atcattctgc actcactggg tgcatagcat ggttagaggg gctagagatg    3180
gacagtcatc aactggcgga tatagcggta catatgatcc ttagccacca gggcacaagc    3240
ttaccagtag acaatacaga cagagctttt gttgagctgt aactgagcta tggaatagct    3300
tctttgatgt acctctttgc cttaaattgc ttttttagttc taagattgta gaatgatcct    3360
ttcaaattgt aatctttttct aacagagata ttttaatata cttgctttct taaaaaacaa    3420
aaaaactact gtcagtatta atactgagcc agactggcat ctacagattt cagatctatc    3480
attttattga ttcttaagct tgtattaaaa actaggcaat atcatcatgg atacatagga    3540
gaagacacat ttacaatcat tcattgggcc ttttatctgt ctatccatcc atcatcattt    3600
gaaggcctaa tatatgccaa gtactcacat ggtatgcatt gagacataaa aaagactgtc    3660
tataacctca ataagtatta aaaatcccat tattacccat aaggttcatc ttatttcatt    3720
tttagggaat aaaattacat gtctatgaaa tttcaatttt aagcactatt gttttcatg     3780 accataattt attttttaaaa ataaattaaa ggttaattat atgcatgtat gtatttctaa   3840
taattaaaaa tgtgttcaat ccctgaaatg tctgcctttt aaatataaca cctactattt    3900
ggttaaaaaa aaaaaaaaaa aaaaa                                         3925

<210> SEQ ID NO 62
<211> LENGTH: 110
<212> TYPE: DNA
<213> ORGANISM: Homo sapiens

<400> SEQUENCE: 62
cagggtgctg ctcagatttc cccaaagagt gaaaaaccaa gggacatcag atttcttacc     60
cagccgacca agatattcct gggaatggca cagttgtcat caacattacc                110

<210> SEQ ID NO 63
<211> LENGTH: 5866
<212> TYPE: DNA
<213> ORGANISM: Homo sapiens

<400> SEQUENCE: 63
gggacctgga agcgccccag ccccgcagcg atcgcagatt cggctttcaa acaaaagagg     60
cgccccgggg ggtgggaccg ggacctcacc cggtcctcgc agagttgcgg ccgcccgccc    120
cttcagcccc ggctctccgt atgcgcatga gcagaggcgc ctccctctgt tcctcccaag    180
gctaaacttt ctaattccct tctttgggct cgggggctcc cggagcaggg cgagagctcg    240
cgtcgccgga aaggaagacg ggaagaaagg gcaggcggct cggcgggcgt cttctccact    300
cctctgccgc gtcccgtgg ctgcaggag ccggcatggg gcttctccag ttgctagctt      360
tcagtttctt agccctgtgc agagcccgag tgcgcgctca ggaacccgag ttcagctacg    420
gctgcgcaga aggcagctgc tatcccgcca cgggcgacct tctcatcggc cgagcacaga    480
agctttcggt gacctcgacg tgcgggctgc acaagcccga accctactgt atcgtcagcc    540
acttgcagga ggacaaaaaa tgcttcatat gcaattccca agatccttat catgagaccc    600
```

```
tgaatcctga cagccatctc attgaaaatg tggtcactac atttgctcca aaccgcctta    660
agatttggtg gcaatctgaa aatggtgtgg aaaatgtaac tatccaactg gatttggaag    720
cagaattcca ttttactcat ctcataatga ctttcaagac attccgtcca gctgctatgc    780
tgatagaacg atcgtccgac tttgggaaaa cctggggtgt gtatagatac ttcgcctatg    840
actgtgaggc ctcgtttcca ggcatttcaa ctggccccat gaaaaaagtc gatgacataa    900
tttgtgattc tcgatattct gacattgaac cctcaactga aggagaggtg atatttcgtg    960
ctttagatcc tgctttcaaa atagaagatc cttatagccc aaggatacag aatttattaa   1020
aaattaccaa cttgagaatc aagtttgtga aactgcatac tttgggagat aaccttctgg   1080
attccaggat ggaaatcaga gaaaagtatt attatgcagt ttatgatatg gtggttcgag   1140
gaaattgctt ctgctatggt catgccagcg aatgtgcccc tgtggatgga ttcaatgaag   1200
aagtggaagg aatggttcac ggacactgca tgtgcaggca taacaccaag ggcttaaact   1260
gtgaactctg catggatttc taccatgatt taccttggag acctgctgaa ggccgaaaca   1320
gcaacgcctg taaaaaatgt aactgcaatg aacattccat ctcttgtcac tttgacatgg   1380
ctgtttacct ggccacgggg aacgtcagcg gaggcgtgtg tgatgactgt cagcacaaca   1440
ccatggggcg caactgtgag cagtgcaagc cgttttacta ccagcaccca gagagggaca   1500
tccgagatcc taatttctgt gaacgatgta cgtgtgaccc agctggctct caaaatgagg   1560
gaatttgtga cagctatact gattttttcta ctggtctcat tgctggccag tgtcggtgta   1620
aattaaatgt ggaaggagaa cattgtgatg tttgcaaaga aggcttctat gatttaagca   1680
gtgaagatcc atttggttgt aaatcttgtg cttgcaatcc tctgggaaca attcctggag   1740
ggaatccttg tgattccgag acaggtcact gctactgcaa gcgtctggtg acaggacagc   1800
attgtgacca gtgcctgcca gagcactggg gcttaagcaa tgatttggat ggatgtcgac   1860
catgtgactg tgaccttggg ggagccttaa caacagttg ctttgcggag tcaggccagt   1920
gctcatgccg gcctcacatg attggacgtc agtgcaacga agtggaacct ggttactact   1980
ttgccaccct ggatcactac ctctatgaag cggaggaagc caacttgggg cctggggtta   2040
gcatagtgga gcggcaatat atccaggacc ggattccctc ctggactgga gccggcttcg   2100
tccgagtgcc tgaaggggct tatttggagt ttttcattga caacatacca tattccatgg   2160
agtacgacat cctaattcgc tacgagccac agctacccga ccactgggaa aaagctgtca   2220
tcacagtgca gcgacctgga aggattccaa ccagcagccg atgtggtaat accatccccg   2280
atgatgacaa ccaggtggtg tcattatcac caggctcaag atatgtcgtc cttcctcggc   2340
cggtgtgctt tgagaaggga acaaactaca cggtgaggtt ggagctgcct cagtacacct   2400
cctctgatag cgacgtggag agcccctaca cgctgatcga ttctcttgtt ctcatgccat   2460
actgtaaatc actggacatc ttcaccgtgg gaggttcagg agatggggtg gtcaccaaca   2520
gtgcctggga aacctttcag agataccgat gtctagagaa cagcagaagc gttgtgaaaa   2580
caccgatgac agatgtttgc agaaacatca tctttagcat ttctgccctg ttacaccaga   2640
caggcctggc ttgtgaatgc gaccctcagg gttcgttaag ttccgtgtgt gatcccaacg   2700
gaggccagtg ccagtgccgg cccaacgtgg ttggaagaac ctgcaacaga tgtgcacctg   2760
gaacttttgg cttttggccc cagtggatgca aaccttgtga gtgccatctg caaggatctg   2820
tcaatgcctt ctgcaatccc gtcactggcc agtgccactg tttccaggga gtgtatgctc   2880
ggcagtgtga tcggtgctta cctgggcact ggggcttttcc aagttgccag ccctgccagt   2940
```

```
gcaatggcca cgccgatgac tgcgacccag tgactgggga gtgcttgaac tgccaggact    3000
acaccatggg tcataactgt gaaaggtgct tggctggtta ctatggcgac cccatcattg    3060
ggtcaggaga tcactgccgc ccttgccctt gcccagatgg tcccgacagt ggacgccagt    3120
ttgccaggag ctgctaccaa gatcctgtta ctttacagct tgcctgtgtt tgtgatcctg    3180
gatacattgg ttccagatgt gacgactgtg cctcaggata ctttggcaat ccatcagaag    3240 ttgggggtc gtgtcagcct tgccagtgtc acaacaacat tgacacgaca gacccagaag    3300
cctgtgacaa ggagactggg aggtgtctca agtgcctgta ccacacggaa ggggaacact    3360
gtcagttctg ccggtttgga tactatggtg atgccctcca gcaggactgt cgaaagtgtg    3420
tctgtaatta cctgggcacc gtgcaagagc actgtaacgg ctctgactgc cagtgcgaca    3480
aagccactgg tcagtgcttg tgtcttccta atgtgatcgg gcagaactgt gaccgctgtg    3540
cgcccaatac ctggcagctg ccagtggca ctggctgtga cccatgcaac tgcaatgctg    3600
ctcattcctt cgggccatct tgcaatgagt tcacggggca gtgccagtgc atgcctgggt    3660
ttggaggccg cacctgcagc gagtgccagg aactcttctg gggagacccc gacgtggagt    3720
gccgagcctg tgactgtgac cccaggggca ttgagacgcc acagtgtgac cagtccacgg    3780
gccagtgtgt ctgcgttgag ggtgttgagg gtccacgctg tgacaagtgc acgcgagggt    3840
actcgggggt cttccctgac tgcacaccct gccaccagtg ctttgctctc tgggatgtga    3900
tcattgccga gctgaccaac aggacacaca gattcctgga gaaagccaag gccttgaaga    3960
tcagtggtgt gatcgggcct taccgtgaga ctgtggactc ggtggagagg aaagtcagcg    4020
agataaaaga catcctggcg cagagccccg cagcagagcc actgaaaaac attgggaatc    4080
tctttgagga agcagagaaa ctgattaaag atgttacaga aatgatggct caagtagaag    4140
tgaaattatc tgacacaact tcccaaagca acagcacagc caagaactg gattctctac    4200 agacagaagc cgaaagccta gacaacactg tgaaagaact tgctgaacaa ctggaattta    4260
tcaaaaactc agatattcgg ggtgccttgg atagcattac caagtatttc agatgtctc    4320 ttgaggcaga ggagagggtg aatgcctcca ccacagaacc caacagcact gtggagcagt    4380
cagccctcat gagagacaga gtagaagacg tgatgatgga gcgagaatcc cagttcaagg    4440
aaaaacaaga ggagcaggct cgcctccttg atgaactggc aggcaagcta caaagcctag    4500
acctttcagc cgctgccgaa atgacctgtg aacacccccc aggggcctcc tgttccgaga    4560
ctgaatgtgg cgggccaaac tgcagaactg acgaaggaga gaggaagtgt gggggcctg    4620 gctgtggtgg tctggttact gttgcacaca cgcctggca gaaagccatg gacttggacc    4680
aagatgtcct gagtgccctg ctgaagtgg aacagctctc caagatggtc tctgaagcaa    4740
aactgagggc agatgaggca aaacaaagtg ctgaagacat tctgttgaag acaaatgcta    4800
ccaaagaaaa aatggacaag agcaatgagg agctgagaaa tctaatcaag caaatcagaa    4860
actttttgac ccaggatagt gctgatttgg acagcattga agcagttgct aatgaagtat    4920
tgaaaatgga gatgcctagc accccacagc agttacagaa cttgacagaa gatatacgtg    4980
aacgagttga aagcctttct caagtagagg ttattcttca gcatagtgct gctgacattg    5040
ccagagctga gatgttgtta gaagaagcta aagagcaag caaagtgca acagatgtta    5100 aagtcactgc agatatggta aaggaagctc tggaagaagc agaaaaggcc caggtcgcag    5160
cagagaaggc aattaaacaa gcagatgaag acattcaagg aacccagaac ctgttaactt    5220
cgattgagtc tgaaacagca gcttctgagg aaaccttgtt caacgcgtcc cagcgcatca    5280
gcgagttaga gaggaatgtg aagaactta agcggaaagc tgcccaaaac tccggggagg    5340
```

```
cagaatatat tgaaaaagta gtatatactg tgaagcaaag tgcagaagat gttaagaaga    5400
ctttagatgg tgaacttgat gaaaagtata aaaaagtaga aaatttaatt gccaaaaaaa    5460
ctgaagagtc agctgatgcc agaaggaaag ccgaaatgct acaaaatgaa gcaaaaactc    5520
ttttagctca agcaaatagc aagctgcaac tgctcaaaga tttagaaaga aaatatgaag    5580
acaatcaaag atacttagaa gataaagctc aagaattagc aagactggaa ggagaagtcc    5640
gttcactcct aaaggatata agccagaaag ttgctgtgta tagcacatgc ttgtaacaga    5700
ggagaataaa aaatggctga ggtgaacaag gtaaacaac tacattttaa aaactgactt     5760
aatgctcttc aaaataaaac atcacctatt taatgttttt aatcacattt tgtatggagt    5820
taaataaagt acagtgcttt tgtataaaaa aaaaaaaaa aaaaaa                    5866

<210> SEQ ID NO 64
<211> LENGTH: 125
<212> TYPE: DNA
<213> ORGANISM: Homo sapiens

<400> SEQUENCE: 64
acaagcccga accctactgt atcgtcagcc acttgcagga ggacaaaaaa tgcttcatat      60
gcaattccca agatccttat catgagaccc tgaatcctga cagccatctc attgaaaatg     120
tggtc                                                                 125

<210> SEQ ID NO 65
<211> LENGTH: 2620
<212> TYPE: DNA
<213> ORGANISM: Homo sapiens

<400> SEQUENCE: 65
agatgcgagc actgcggctg ggcgctgagg atcagccgct tcctgcctgg attccacagc      60
ttcgcgccgt gtactgtcgc cccatccctg cgcgcccagc ctgccaagca gcgtgccccg     120
gttgcaggcg tcatgcagcg ggcgcgaccc acgctctggg ccgctgcgct gactctgctg     180
gtgctgctcc gcgggccgcc ggtggcgcgg gctggcgcga gctcggcggg cttgggtccc     240
gtggtgcgct gcgagccgtg cgacgcgcgt gcactggccc agtgcgcgcc tccgcccgcc     300
gtgtgcgcgg agctggtgcg cgagccgggc tgcggctgct gcctgacgtg cgcactgagc     360
gagggccagc cgtgcggcat ctacaccgag cgctgtggcc ccggccttcg ctgccagccg     420
tcgcccgacg aggcgcgacc gctgcaggcg ctgctggacg gccgcgggct ctgcgtcaac     480
gctagtgccg tcagccgcct gcgcgcctac ctgctgccag cgccgccagc tccaggaaat     540
gctagtgagt cggaggaaga ccgcagcgcc ggcagtgtgg agagcccgtc cgtctccagc     600
acgcaccggg tgtctgatcc caagttccac cccctccatt caaagataat catcatcaag     660
aaagggcatg ctaaagacag ccagcgctac aaagttgact acgagtctca gagcacagat     720
acccagaact tctcctccga gtccaagcgg agacagaat atggtccctg ccgtagagaa     780
atggaagaca cactgaatca cctgaagttc ctcaatgtgc tgagtcccag ggtgtacac      840 attcccaact gtgacaagaa gggatttttat aagaaaaagc agtgtcgccc ttccaaaggc     900
aggaagcggg gcttctgctg gtgtgtggat aagtatgggc agcctctccc aggctacacc     960
accaagggga aggaggacgt gcactgctac agcatgcaga gcaagtagac gcctgccgca    1020
aggttaatgt ggagctcaaa tatgcctat tttgcacaaa agactgccaa ggacatgacc     1080
agcagctggc tacagcctcg atttatattt ctgtttgtgg tgaactgatt ttttttaaac    1140
```

| | |
|---|---:|
| caaagtttag aaagaggttt ttgaaatgcc tatggtttct ttgaatggta aacttgagca | 1200 |
| tcttttcact ttccagtagt cagcaaagag cagtttgaat tttcttgtcg cttcctatca | 1260 |
| aaatattcag agactcgagc acagcaccca gacttcatgc gcccgtggaa tgctcaccac | 1320 |
| atgttggtcg aagcggccga ccactgactt tgtgacttag cggctgtgt tgcctatgta | 1380 |
| gagaacacgc ttcacccca ctccccgtac agtgcgcaca ggctttatcg agaataggaa | 1440 |
| aacctttaaa ccccggtcat ccggacatcc aacgcatgc tcctggagct cacagccttc | 1500 |
| tgtggtgtca tttctgaaac aagggcgtgg atccctcaac aagaagaat gtttatgtct | 1560 |
| tcaagtgacc tgtactgctt ggggactatt ggagaaaata aggtggagtc ctacttgttt | 1620 |
| aaaaaatatg tatctaagaa tgttctaggg cactctggga acctataaag gcaggtattt | 1680 |
| cgggccctcc tcttcaggaa tcttcctgaa gacatggccc agtcgaaggc ccaggatggc | 1740 |
| ttttgctgcg gccccgtggg gtaggaggga cagagagaca gggagagtca gcctccacat | 1800 |
| tcagaggcat cacaagtaat ggcacaattc ttcggatgac tgcagaaaat agtgttttgt | 1860 |
| agttcaacaa ctcaagacga agcttatttc tgaggataag ctctttaaag gcaaagctttt | 1920 |
| attttcatct ctcatctttt gtcctcctta gcacaatgta aaaagaata gtaatatcag | 1980 |
| aacaggaagg aggaatggct tgctggggag cccatccagg acactgggag cacatagaga | 2040 |
| ttcacccatg tttgttgaac ttagagtcat tctcatgctt ttctttataa ttcacacata | 2100 |
| tatgcagaga agatatgttc ttgttaacat tgtatacaac atagcccaa atatagtaag | 2160 |
| atctatacta gataatccta gatgaaatgt tagagatgct atatgataca actgtggcca | 2220 |
| tgactgagga aaggagctca cgcccagaga ctgggctgct ctcccggagg ccaaacccaa | 2280 |
| gaaggtctgg caaagtcagg ctcagggaga ctctgccctg ctgcagacct cggtgtggac | 2340 |
| acacgctgca tagagctctc cttgaaaaca gaggggtctc aagacattct gcctaccctat | 2400 |
| tagcttttct ttattttttt aacttttggg ggggaaaagt attttttgaga agtttgtctt | 2460 |
| gcaatgtatt tataaatagt aaataaagtt tttaccatta aaaaaatatc tttcccttttg | 2520 |
| ttattgacca tctctgggct ttgtatcact aattatttta ttttattata taataattat | 2580 |
| tttattataa taaaatcctg aaaggggaaa ataaaaaaaa | 2620 |

<210> SEQ ID NO 66
<211> LENGTH: 105
<212> TYPE: DNA
<213> ORGANISM: Homo sapiens

<400> SEQUENCE: 66

| | |
|---|---:|
| agagcacaga tacccagaac ttctcctccg agtccaagcg ggagacagaa tatggtccct | 60 |
| gccgtagaga aatggaagac acactgaatc acctgaagtt cctca | 105 |

<210> SEQ ID NO 67
<211> LENGTH: 1355
<212> TYPE: DNA
<213> ORGANISM: Homo sapiens

<400> SEQUENCE: 67

| | |
|---|---:|
| cagtggctgg taggcagtgg ctgggaggca gcggcccaat tagtgtcgtg cggcccgtgg | 60 |
| cgaggcgagg tccggggagc gagcgagcaa gcaaggcggg aggggtggcc ggagctgcgg | 120 |
| cggctggcac aggaggagga gcccgggcgg gcgaggggcg gccggagagc gccagggcct | 180 |
| gagctgccga agcggcgcct gtgagtgagt gcagaaagca ggcgcccgcg cgctagccgt | 240 |
| ggcaggagca gcccgcacgc cgcgctctct ccctgggcga cctgcagttt gcaatatgac | 300 |

```
tttggaggaa ttctcggctg gagagcagaa gaccgaaagg atggataagg tggggatgc       360 cctggaggaa gtgctcagca aagccctgag tcagcgcacg atcactgtcg gggtgtacga       420
agcggccaag ctgctcaacg tcgaccccga taacgtggtg ttgtgcctgc tggcggcgga       480
cgaggacgac gacagagatg tggctctgca gatccacttc accctgatcc aggcgttttg       540
ctgcgagaac gacatcaaca tcctgcgcgt cagcaacccg ggccggctgg cggagctcct       600
gctcttggag accgacgctg gccccgcggc gagcgagggc gccgagcagc ccccggacct       660
gcactgcgtg ctggtgacga atccacattc atctcaatgg aaggatcctg ccttaagtca       720
acttatttgt ttttgccggg aaagtcgcta catggatcaa tgggttccag tgattaatct       780
ccctgaacgg tgatggcatc tgaatgaaaa taactgaacc aaattgcact gaagttttg       840 aaatacctt gtagttactc aagcagttac tccctacact gatgcaagga ttacagaaac       900
tgatgccaag gggctgagtg agttcaacta catgttctgg gggcccggag atagatgact       960
ttgcagatgg aaagaggtga aaatgaagaa ggaagctgtg ttgaaacaga aaataagtc       1020 aaaaggaaca aaaattacaa agaaccatgc aggaaggaaa actatgtatt aatttagaat       1080
ggttgagtta cattaaaata aaccaaatat gttaaagttt aagtgtgcag ccatagtttg       1140 ggtattttg gtttatatgc cctcaagtaa agaaaagcc gaagggtta atcatatttg       1200 aaaaccatat tttattgtat tttgatgaga tattaaattc tcaaagttttt attataaatt       1260 ctactaagtt attttatgac atgaaaagtt atttatgcta taaattttt gaaacacaat       1320 acctacaata aactggtatg aataattgca tcatt                                 1355

<210> SEQ ID NO 68
<211> LENGTH: 145
<212> TYPE: DNA
<213> ORGANISM: Homo sapiens

<400> SEQUENCE: 68
gagagcagaa gaccgaaagg atggataagg tggggatgc cctggaggaa gtgctcagca       60
aagccctgag tcagcgcacg atcactgtcg gggtgtacga agcggccaag ctgctcaacg       120
tcgaccccga taacgtggtg ttgtg                                            145

<210> SEQ ID NO 69
<211> LENGTH: 3742
<212> TYPE: DNA
<213> ORGANISM: Homo sapiens

<400> SEQUENCE: 69
atttcctccg aggctggcga tcggcggagc tcccacctcc gcttacagct cgctgccgcc       60
gtcctgcccc gcgcccccag gagacctgga ccagaccacg atgtggaaac gctggctcgc       120
gctcgcgctc gcgctggtgg cggtcgcctg ggtccgcgcc gaggaagagc taaggagcaa       180
atccaagatc tgtgccaatg tgtttttgtgg agccggccgg gaatgtgcag tcacagagaa       240 agggggaaccc acctgtctct gcattgagca atgcaaacct cacaagaggc ctgtgtgtgg       300
cagtaatggc aagacctacc tcaaccactg tgaactgcat cgagatgcct gcctcactgg       360
atccaaaatc caggttgatt acgatggaca ctgcaaagag aagaaatccg taagtccatc       420
tgccagccca gttgtttgct atcagtccaa ccgtgatgag ctccgacgtc gcatcatcca       480
gtggctggaa gctgagatca ttccagatgg ctggttctct aaaggcagca actacagtga       540
aatcctagac aagtatttta agaactttga taatggtgat tctcgcctgg actccagtga       600
```

```
attcctgaag tttgtggaac agaatgaaac tgccatcaat attacaacgt atccagacca    660
ggagaacaac gagttgctta ggggactctg tgttgatgct ctcattgaac tgtctgatga    720
aaatgctgat tggaaactca gcttccaaga gtttctcaag tgcctcaacc catctttcaa    780
ccctcctgag aagaagtgtg ccctggagga tgaaacgtat gcagatggag ctgagaccga    840
ggtggactgt aaccgctgtg tctgtgcctg tggaaattgg gtctgtacag ccatgacctg    900
tgacggaaag aatcagaagg gggcccagac ccagacagag gaggagatga ccagatatgt    960
ccaggagctc caaaagcatc aggaaacagc tgaaagacc aagagagtga gcaccaaaga   1020
gatctaatga ggaggcacag accagtgtct ggatcccagc atcttctcca cttcagcgct   1080
gagttcagta tacacaagtg tctgctacag tcgccaaatc accagtattt gcttatatag   1140
caatgagttt tattttgttt atttgttttg caataaagga tatgaaggtg gctggctagg   1200
aagggaaggg ccacagcctt catttctagg agtgctttaa gagaaactgt aaatggtgct   1260
ctggggctgg aggctagtaa ggaaactgca tcacgattga agaggaaca gacccaaatc   1320 tgaacctctt ttgagtttac tgcatctgtc agcaggctgc agggagtgca cacgatgcca   1380
gagagaactt agcagggtgt ccccggagga gaggtttggg aagctccacg gagaggaacg   1440
ctctctgctt ccagcctctt tccattgccg tcagcatgac agacctccag catccacgca   1500
tctcttggtc ccaataactg cctctagata catagccata ctgctagtta acccagtgtc   1560
cctcagactt ggatggagtt tctgggaggg tacacccaaa tgatgcagat acttgtatac   1620
tttgagcccc ttagcgacct aaccaaattt taaaaatact ttttaccaaa ggtgctattt   1680
ctctgtaaaa cactttttt tggcaggttg actttattct tcaattatta tcattatatt   1740
attgtttttt aatattttat tttcttgact aggtattaag cttttgtaat tatttttcag   1800
tagtcccacc acttcatagg tggaaggagt ttggggttct tcctggtgca ggggctgaaa   1860
taacccagat gcccccaccc tgccacatac tagatgcagc ccatagttgg cccccctagc   1920
ttccagcagt ccactatctg ccagaggagc aagggtgcct tagaccgaag ccaggggaag   1980
aagcatcttc ataaaaaact ttcaagatcc aaacattaat ttgtttttat ttattctgag   2040
aagttgaggc aaatcagtat tcccaaggat ggcgacaagg gcagccaagc agggcttagg   2100
atatcccagc ctaccaatat gctcattcga ctaactagga gggtgagttg gccctgtctc   2160 ttctttttc tggaccctcag tttcctcagt gagctggtaa gaatgcacta accttttgat   2220
ttgataagtt ataaattctg tggttctgat cattggtcca gaggggagat aggttcctgt   2280
gatttttcct tcttctctat agaataaatg aaatcttgtt actagaacaa gaaatgtcag   2340
atggccaaaa acaagatgac cagatttgat ctcagcctga tgaccctaca ggtcgtgcta   2400
tgatatggag tcctcatggg taaagcagga agagagtggg aaagaaacc accccactct   2460 gtcttcatat ttgcatttca tgtttaacct ccggctggaa atagaaagca ttcccttaga   2520
gatgaggata aaagaaagtt tcagattcaa caggggaag aaaatggaga tttaatccta   2580
aaactgtgac ttggggaggt cagtcattta cagttagtcc tgtgtctttc gacttctgtg   2640
attattaacc ccactcacta ccctgtttca gatgcatttg aataccaaa gattaaatcc    2700 ttgacataag atctcatttg cagaaagcag attaagacc atcagaagga aattatttag    2760
gttgtaatgc acaggcaact gtgagaaact gttgtgccaa aaatagaatt ccttctagtt   2820
tttcttgttc tcatttgaaa ggagaaaatt ccactttgtt tagcatttca agcttttatg   2880
tatccatccc atctaaaaac tcttcaaact ccacttgttc agtctgaaat gcagctcccc   2940
gtccaagtgc cttggagaac tcacagcagc acgccttaat caaaggtttt accagcccctt   3000
```

```
ggacactatg ggaggagggc aagagtacac caatttgtta aaagcaagaa accacagtgt    3060
ctcttcacta gtcatttaga acatggttat catccaagac tactctaccc tgcaacattg    3120
aactcccaag agcaaatcca cattcctctt gagttctgca gcttctgtgt aaatagggca    3180
gctgtcgtct atgccgtaga atcacatgat ctgaggacca ttcatggaag ctgctaaata    3240
gcctagtctg gggagtcttc cataaagttt tgcatggagc aaacaaacag gattaaacta    3300
ggtttggttc cttcagccct ctaaaagcat agggcttagc ctgcaggctt ccttgggctt    3360
tctctgtgtg tgtagttttg taaacactat agcatctgtt aagatccagt gtccatggaa    3420
acattcccac atgccgtgac tctggactat atcagttttt ggaaagcagg gttcctctgc    3480
ctgctaacaa gcccacgtgg accagtctga atgtctttcc tttacaccta tgtttttaag    3540
tagtcaaact tcaagaaaca atctaaacaa gtttctgttg catatgtgtt tgtgaacttg    3600
tatttgtatt tagtaggctt ctatattgca tttaacttgt ttttgtaact cctgattctt    3660
ccttttcgga tactattgat gaataaagaa attaaagtga aaaaaaaaaa aaaaaaaaa    3720 aagaaaaaaa aaaaaaaaaa aa                                              3742

<210> SEQ ID NO 70
<211> LENGTH: 204
<212> TYPE: DNA
<213> ORGANISM: Homo sapiens

<400> SEQUENCE: 70
caaccactgt gaactgcatc gagatgcctg cctcactgga tccaaaatcc aggttgatta     60
cgatggacac tgcaaagaga agaaatccgt aagtccatct gccagcccag ttgtttgcta    120
tcagtccaac cgtgatgagc tccgacgtcg catcatccag tggctggaag ctgagatcat    180
tccagatggc tggttctcta aagg                                            204

<210> SEQ ID NO 71
<211> LENGTH: 2199
<212> TYPE: DNA
<213> ORGANISM: Homo sapiens

<400> SEQUENCE: 71
ggagcctgta gcctttattc atgccccct gaccaaatgc agtgagagac aaggcccctg      60
ccgaaaacaa ctccagggc ctgggactct ggtccccta ctgcagacac tttcctgtga     120
gccagaagtg tataaagtgc tggtgtgtga ccatcctttg ggaaggtca aggggggcaa    180 gatccccagg ggccctgagg aagggcaggg cataggcgtg gctcccagag cgctgggagg    240
gagggcccgt gccaccacct cggggctaga aaacaatgca gtcctgggca ggagggaact    300
gaaaatggga gccttcagca tggagccctc aggaggctgg ggttgtaggg ggataatttc    360 tgtaccctg tgaagggagg gggcatgtag gaaaggcctt ggggatctca gagaatggga    420
cagcccctcc gacgcttgtt cttgcggacc tggaggccag cccgagtggc catctcaaac    480
acctcccgca ctccctcctt ggtcttggct gagcactcaa ggtagccaaa ggcactgatc    540
cggttcgcca gtcccggcc ttcctcagac cgaacgggct cctgcttcat cttggccagc    600
tctctcctgg tgtgctcgtc ttgcctcagg tccttcttat tccccaccag gatgatgggc    660
acgttggggc agaagtgctt cacctctggg gtccacttct caggaatgtt ttccaggctg    720
tcagggctgt cgatggagaa gcacatgagg atgacatcag tgtccgggta ggagagaggc    780
cgcagtcgat catagtcttc ctgccctgct gtgtcccaca gagccagctc cacctgcttg    840
```

-continued

| | |
|---|---|
| ccgtccacct caatgtccgc aatatagttc tcaaagacag tagggacgta gacctccgga | 900 |
| aactgatcct tgctgaagac gatgaggagg caggtcttcc cacaggcacc atccccaacg | 960 |
| atcaccagct tctttcggat tgcagccatg gtggggctcc agccggctga agttcccagg | 1020 |
| ctgcaggaag agagggcggg ctctggagct gagatgaagt caaggctgtt gggaaggggg | 1080 |
| aggggctag agtctgggct gggaggagcc ccaaaagaag agacaaatga gggccagtcc | 1140 |
| cagcaccaac caggcaggga gcagttaaga aagcgacggt aacctgatct cagcctcaaa | 1200 |
| cctagctttt tctctcagtc ccacatcctg tcaaactggg ctgactgaac gcctctactc | 1260 |
| cccacacccc accaccacct cacactgccc tttaggaagc gaatactcca gcccaggcc | 1320 |
| tcttcccttc aacatagatc ctgagtggcc cttcccttgc ctccagacac attcacaaaa | 1380 |
| ctgttggttt tgtggacatg agtcagagaa tttacaggag ttcaaagtac acagccacac | 1440 |
| tcttcccacc acaaaacgga ctctctctga ttccccagaa gacaagcaag aaggcattca | 1500 |
| ccctgtcggc agatcgcctc cagaaatgga accatcctc caaaagagg gttccttggg | 1560 |
| aattctatcc cggtgactga cgctgggatt tcttccaact cctccaccca ctccattagt | 1620 |
| tcaccttgcc ctgttttgta aagatgggct ggggtagccc caacctgggg tgggcagtgt | 1680 |
| tgatggaggg caatcactac tggggtgaaa gccagtcact taggcatgag tatgccactg | 1740 |
| ctgtcccccc agcagggtaa ttcagacggc accagagtgg tgggaggcag aggacagaaa | 1800 |
| cccggggttg aggcatgcgt taagggacct ggagcctcca gcccaattag aagactttcc | 1860 |
| ctccaggcta tgattgggcc agaacagcag gcagcccagg ccaggacact aggcccaagg | 1920 |
| ccaagatggc atggacaact ccctgtgaga ggcagcccca gagggactgt cccactgacc | 1980 |
| ccttaagagg ggcaactgag ccccacacag ggcctggaat ggagcctgga acttctgggg | 2040 |
| ccttccccaa gacaagacag tgtggataca tcagacctct ctccaatcgc tctcttgaat | 2100 |
| tcccagatga tccagagcgg ccggttgact ttgccggccc accctacacc ttccgctccg | 2160 |
| ccgcctccag ctgcgcggcc ggtgccggag gctcagact | 2199 |

<210> SEQ ID NO 72
<211> LENGTH: 195
<212> TYPE: DNA
<213> ORGANISM: Homo sapiens

<400> SEQUENCE: 72

| | |
|---|---|
| cctgcctcct catcgtcttc agcaaggatc agtttccgga ggtctacgtc cctactgtct | 60 |
| ttgagaacta tattgcggac attgaggtgg acggcaagca ggtggagctg gctctgtggg | 120 |
| acacagcagg gcaggaagac tatgatcgac tgcggcctct ctcctacccg gacactgatg | 180 |
| tcatcctcat gtgct | 195 |

<210> SEQ ID NO 73
<211> LENGTH: 4125
<212> TYPE: DNA
<213> ORGANISM: Homo sapiens

<400> SEQUENCE: 73

| | |
|---|---|
| cggctatccg cgcgggagtg cgccacgcgg ggccggagcg cctattagcc gccaggacct | 60 |
| cggagcgccc cgaccacccc tgagcccctc tggcttcgga gccccccagc acccccttccc | 120 |
| gggtccccte gcccacccta atccactctc cctcccttc ccggattccc tcgctcaccc | 180 |
| catcctctct cccgccccctt cctggattcc ctcaccgtc tcgatcccct ctcgccctt | 240 |
| tcccagagac ccagagcccc tgaccccccg cgccctcccc ggagccccc gcgcgtgccg | 300 |

```
cggccatggc ggccgtgcgc ggggcgcccc tgctcagctg cctcctgcg ttgctggccc      360
tgtgccctgg agggcgcccg cagacggtgc tgaccgacga cgagatcgag gagttcctcg     420
agggcttcct gtcagagcta gaacctgagc cccggagga cgacgtggag gccccgccgc      480
ctcccgagcc caccccgcgg gtccgaaaag cccaggcggg gggcaagcca gggaagcggc     540
cagggacggc cgcagaagtg cctccggaaa agaccaaaga caaagggaag aaaggcaaga    600
aagacaaagg ccccaaggtg cccaaggagt ccttggaggg gtcccccagg ccgcccaaga    660
aggggaagga gaagccaccc aaggccacca agaagcccaa ggagaagcca cctaaggcca    720
ccaagaagcc caaggagaag ccacccaagg ccaccaagaa gcccaaagag aagccaccca    780
aggccaccaa gaagcccccg tcagggaaga ggccccccat tctggctccc tcagaaaccc    840
tggagtggcc actgcccccca ccccccagcc ctggccccga ggagctaccc caggagggag   900
gggcgcccct ctcaaataac tggcagaatc caggagagga gacccatgtg gaggcacggg    960
agcaccagcc tgagccggag gaggagaccg agcaacccac actggactac aatgaccaga   1020
tcgagaggga ggactatgag gactttgagt acattcggcg ccagaagcaa cccaggccac   1080
ccccaagcag aaggaggagg cccgagcggg tctggccaga gcccctgag gagaaggccc    1140
cggccccagc cccggaggag aggattgagc ctcctgtgaa gcctctgctg ccccgctgc    1200
cccctgacta tggtgatggt tacgtgatcc caactacga tgacatggac tattactttg    1260
ggcctcctcc gccccagaag cccgatgctg agcgccagac ggacgaagag aaggaggagc   1320
tgaagaaacc caaaaaggag gacagcagcc caaggagga ccgacaag tgggcagtgg      1380
agaagggcaa ggaccacaaa gagccccgaa agggcgagga gttggaggag gagtggacgc    1440
ctacggagaa agtcaagtgt ccccccattg ggatggagtc acaccgtatt gaggacaacc    1500
agatccgagc ctcctccatg ctgcgccacg gcctggggc acagcgcggc cggctcaaca   1560
tgcagaccgg tgccactgag gacgactact atgatggtgc gtggtgtgcc gaggacgatg   1620
ccaggaccca gtggatagag gtggacacca ggaggactac ccggttcaca ggcgtcatca    1680
cccagggcag agactccagc atccatgacg attttgtgac caccttcttc gtgggcttca    1740
gcaatgacag ccagacatgg gtgatgtaca ccaacggcta tgaggaaatg accttcatg    1800
ggaacgtgga caaggacaca cccgtgctga gtgagctccc agagccggtg gtggctcgtt    1860
tcatccgcat ctacccactc acctggaatg cagcctgtg catgcgcctg gaggtgctgg    1920
ggtgctctgt ggcccctgtc tacagctact acgcacagaa tgaggtggtg gccaccgatg    1980
acctggattt ccggcaccac agctacaagg acatgcgcca gctcatgaag gtggtgaacg    2040
aggagtgccc caccatcacc cgcacttaca gcctgggcaa gagctcacga ggcctcaaga    2100
tctatgccat ggagatctca gacaaccctg gggagcatga actggggggag cccgagttcc  2160
gctacactgc tgggatccat ggcaacgagg tgctgggccg agagctgttg ctgctgctca    2220
tgcagtacct gtgccgagag taccgcgatg ggaaccacg tgtgcgcagc ctggtgcagg    2280
acacacgcat ccacctggtg ccctcactga accctgatgg ctacgaggtg cagcgcaga    2340
tgggctcaga gtttgggaac tgggcgctgg gactgtggac tgaggaggc tttgacatct    2400
ttgaagattt cccggatctc aactctgtgc tctgggagc tgaggagagg aaatgggtcc    2460
cctaccgggt ccccaacaat aacttgccca tccctgaacg ctaccttcg ccagatgcca    2520
cggtatccac ggaggtccgg gccatcattg cctggatgga aagaaccccc ttcgtgctgg   2580
gagcaaatct gaacggcggc gagcggctag tatcctaccc ctacgatatg gcccgcacgc    2640
```

| | |
|---|---|
| ctacccagga gcagctgctg gccgcagcca tggcagcagc ccgggggggag gatgaggacg | 2700 |
| aggtctccga ggcccaggag actccagacc acgccatctt ccgtggcttt gccatctcct | 2760 |
| tcgcctccgc acacctcacc ttgaccgagc cctaccgcgg aggctgccaa gcccaggact | 2820 |
| acaccggcgg catgggcatc gtcaacgggg ccaagtggaa ccccggacc gggactatca | 2880 |
| atgacttcag ttacctgcat accaactgcc tggagctctc cttctacctg gctgtgaca | 2940 |
| agttccctca tgagagtgag ctgccccgcg agtgggagaa caacaaggag cgcctgctca | 3000 |
| ccttcatgga gcaggtgcac cgcggcatta aggggggtggt gacggacgag caaggcatcc | 3060 |
| ccattgccaa cgccaccatc tctgtgagtg gcattaatca cggcgtgaag acagccagtg | 3120 |
| gtggtgatta ctggcgaatc ttgaacccgg gtgagtaccg cgtgacagcc cacgcggagg | 3180 |
| gctacaccc gagcgccaag acctgcaatg ttgactatga catcgggcc actcagtgca | 3240 |
| acttcatcct ggctcgctcc aactggaagc gcatccggga gatcatggcc atgaacggga | 3300 |
| accggcctat cccacacata gacccatcgc gccctatgac cccccaacag cgacgcctgc | 3360 |
| agcagcgacg cctacaacac cgcctgcggc ttcgggcaca gatgcggctg cggcgcctca | 3420 |
| acgccaccac caccctaggc ccccacactg tgcctcccac gctgccccct gccctgcca | 3480 |
| ccaccctgag cactaccata gagccctggg gcctcatacc gccaaccacc gctggctggg | 3540 |
| aggagtcgga gactgagacc tacacagagg tggtgacaga gtttgggacc gaggtggagc | 3600 |
| ccgagtttgg gaccaaggtg gagcccgagt ttgagaccca gttggagcct gagtttgaga | 3660 |
| cccagctgga acccgagttt gaggaagagg aggaggagga gaaagaggag gagatagcca | 3720 |
| ctggccaggc attcccccttc acaacagtag agacctacac agtgaacttt ggggacttct | 3780 |
| gagatcagcg tcctaccaag accccagccc aactcaagct acagcagcag cacttcccaa | 3840 |
| gcctgctgac cacagtcaca tcacccatca gcacatggaa ggcccctggt atggacactg | 3900 |
| aaaggaaggg ctggtcctgc ccctttgagg gggtgcaaac atgactggga cctaagagcc | 3960 |
| agaggctgtg tagaggctcc tgctccacct gccagtctcg taagagatgg ggttgctgca | 4020 |
| gtgttggagt aggggcagag ggagggagcc aaggtcactc caataaaaca agctcatggc | 4080 |
| aaaaaaaaaa aaaaaaaaaa aaaaaaaaaa aaaaaaaaaa aaaaa | 4125 |

<210> SEQ ID NO 74
<211> LENGTH: 105
<212> TYPE: DNA
<213> ORGANISM: Homo sapiens

<400> SEQUENCE: 74

| | |
|---|---|
| aaagggcgag gagttggagg aggagtggac gcctacggag aaagtcaagt gtcccccat | 60 |
| tgggatggag tcacaccgta ttgaggacaa ccagatccga gcctc | 105 |

<210> SEQ ID NO 75
<211> LENGTH: 987
<212> TYPE: DNA
<213> ORGANISM: Homo sapiens

<400> SEQUENCE: 75

| | |
|---|---|
| aatataagtg gaggcgtcgc gctggcgggc attcctgaag ctgacagcat tcgggccgag | 60 |
| atgtctcgct ccgtggcctt agctgtgctc gcgctactct ctctttctgg cctggaggct | 120 |
| atccagcgta ctccaaagat tcaggtttac tcacgtcatc cagcagagaa tggaaagtca | 180 |
| aatttcctga attgctatgt gtctgggttt catccatccg acattgaagt tgacttactg | 240 |
| aagaatggag agagaattga aaaagtggag cattcagact tgtctttcag caaggactgg | 300 |

```
tctttctatc tcttgtacta cactgaattc accccactg aaaaagatga gtatgcctgc        360
cgtgtgaacc atgtgacttt gtcacagccc aagatagtta agtgggatcg agacatgtaa        420
gcagcatcat ggaggtttga agatgccgca tttggattgg atgaattcca aattctgctt        480
gcttgctttt taatattgat atgcttatac acttacactt tatgcacaaa atgtagggtt        540
ataataatgt taacatggac atgatcttct ttataattct actttgagtg ctgtctccat        600
gtttgatgta tctgagcagg ttgctccaca ggtagctcta ggagggctgg caacttagag        660
gtggggagca gagaattctc ttatccaaca tcaacatctt ggtcagattt gaactcttca        720
atctcttgca ctcaaagctt gttaagatag ttaagcgtgc ataagttaac ttccaattta        780
catactctgc ttagaaatttg ggggaaaatt tagaaatata attgacagga ttattggaaa        840
tttgttataa tgaatgaaac attttgtcat ataagattca tatttacttc ttatacattt        900
gataaagtaa ggcatggttg tggttaatct ggtttatttt tgttccacaa gttaaataaa        960
tcataaaact tgatgtgtta tctctta                                            987

<210> SEQ ID NO 76
<211> LENGTH: 337
<212> TYPE: DNA
<213> ORGANISM: Homo sapiens

<400> SEQUENCE: 76
aggctatcca gcgtactcca aagattcagg tttactcacg tcatccagca gagaatggaa         60
agtcaaattt cctgaattgc tatgtgtctg ggtttcatcc atccgacatt gaagttgact        120
tactgaagaa tggagagaga attgaaaaag tggagcattc agacttgtct ttcagcaagg        180
actggtcttt ctatctcttg tactacactg aattcacccc cactgaaaaa gatgagtatg        240
cctgccgtgt gaaccatgtg actttgtcac agcccaagat agttaagtgg gatcgagaca        300
tgtaagcagc atcatggagg tttgaagatg ccgcatt                                 337

<210> SEQ ID NO 77
<211> LENGTH: 1035
<212> TYPE: DNA
<213> ORGANISM: Homo sapiens

<400> SEQUENCE: 77
gcggtgccct tgcggcgcag ctggggtcgc ggccctgctc cccgcgcttt cttaaggccc         60
gcgggcggcg caggagcggc actcgtggct gtggtggctt cggcagcggc ttcagcagat        120
cggcggcatc agcggtagca ccagcactag cagcatgttg agccgggcag tgtgcggcac        180
cagcaggcag ctggctccgg ttttggggta tctgggctcc aggcagaagc acagcctccc        240
cgacctgccc tacgactacg cgccctgga acctcacatc aacgcgcaga tcatgcagct        300
gcaccacagc aagcaccacg cggcctacgt gaacaacctg aacgtcaccg aggagaagta        360
ccaggaggcg ttggccaagg gagatgttac agcccagata gctcttcagc ctgcactgaa        420
gttcaatggt ggtggtcata tcaatcatag cattttctgg acaaacctca gccctaacgg        480
tggtggagaa cccaaagggg agttgctgga agccatcaaa cgtgactttg gttcctttga        540
caagtttaag gagaagctga cggctgcatc tgttggtgtc caaggctcag gttggggttg        600
gcttggtttc aataaggaac ggggacactt acaaattgct gcttgtccaa atcaggatcc        660
actgcaagga acaacaggcc ttattccact gctggggatt gatgtgtggg agcacgctta        720
ctaccttcag tataaaaatg tcaggcctga ttatctaaaa gctatttgga atgtaatcaa        780
```

| | |
|---|---|
| ctgggagaat gtaactgaaa gatacatggc ttgcaaaaag taaaccacga tcgttatgct | 840 |
| gatcataccc taatgatccc agcaagataa tgtcctgtct tctaagatgt gcatcaagcc | 900 |
| tggtacatac tgaaaaccct ataaggtcct ggataatttt tgtttgatta ttcattgaag | 960 |
| aaacatttat tttccaattg tgtgaagttt ttgactgtta ataaaagaat ctgtcaacca | 1020 |
| tcaaaaaaaa aaaaa | 1035 |

<210> SEQ ID NO 78
<211> LENGTH: 180
<212> TYPE: DNA
<213> ORGANISM: Homo sapiens

<400> SEQUENCE: 78

| | |
|---|---|
| aacctcagcc ctaacggtgg tggagaaccc aaaggggagt tgctggaagc catcaaacgt | 60 |
| gactttggtt cctttgacaa gtttaaggag aagctgacgg ctgcatctgt tggtgtccaa | 120 |
| ggctcaggtt ggggttggct tggtttcaat aaggaacggg gacacttaca aattgctgct | 180 |

<210> SEQ ID NO 79
<211> LENGTH: 4593
<212> TYPE: DNA
<213> ORGANISM: Homo sapiens

<400> SEQUENCE: 79

| | |
|---|---|
| gctgccgcgc cccgcccttt ctcggccccc ggagggtgac ggggtgaagg cgggggaacc | 60 |
| gaggtgggga gtccgccaga gctcccagac tgcgagcacg cgagccgccg cagccgtcac | 120 |
| ccgcgccgcg tcacggctcc cgggcccgcc ctcctctgac ccctcccctc tctccgtttc | 180 |
| cccctctccc cctcctccgc cgaccgagca gtgacttaag caacggagcg cggtgaagct | 240 |
| cattttctc cttcctcgca gccgcgccag ggagctcgcg gcgcgcggcc cctgtcctcc | 300 |
| ggcccgagat gaatcctgcg gcagaagccg agttcaacat cctcctggcc accgactcct | 360 |
| acaaggttac tcactataaa caatatccac ccaacacaag caaagtttat tcctactttg | 420 |
| aatgccgtga aagaagaca gaaaactcca aattaaggaa ggtgaaatat gaggaaacag | 480 |
| tattttatgg gttgcagtac attcttaata agtacttaaa aggtaaagta gtaaccaaag | 540 |
| agaaaatcca ggaagccaaa gatgtctaca agaacatttt ccaagatgat gtctttaatg | 600 |
| aaaagggatg gaactacatt cttgagaagt atgatgggca tcttccaata gaaataaaag | 660 |
| ctgttcctga gggctttgtc attcccagag gaaatgttct cttcacggtg gaaaacacag | 720 |
| atccagagtt ttactggctt acaaattgga ttgagactat tcttgttcag tcctggtatc | 780 |
| caatcacagt ggccacaaat tctagagagc agaagaaaat attggccaaa tatttgttag | 840 |
| aaacttctgg taacttagat ggtctggaat acaagttaca tgattttggc tacagaggag | 900 |
| tctcttccca agagactgct ggcataggag catctgctca cttggttaac ttcaaggaa | 960 |
| cagatacagt agcaggactt gctctaatta aaaaatatta tggaacgaaa gatcctgttc | 1020 |
| caggctattc tgttccagca gcagaacaca gtaccataac agcttggggg aaagaccatg | 1080 |
| aaaaagatgc ttttgaacat attgtaacac agttttcatc agtgcctgta tctgtggtca | 1140 |
| gcgatagcta tgacatttat aatgcgtgtg agaaaatatg gggtgaagat ctaagacatt | 1200 |
| taatagtatc aagaagtaca caggcaccac taataatcag acctgattct ggaaaccctc | 1260 |
| ttgacactgt gttaaaggtt ttggagattt taggtaagaa gtttcctgtt actgagaact | 1320 |
| caaagggtta caagttgctg ccaccttatc ttagagttat tcaaggggat ggagtagata | 1380 |
| ttaataccctt acaagagatt gtagaaggca tgaaacaaaa aatgtggagt attgaaaata | 1440 |

```
ttgccttcgg ttctggtgga ggtttgctac agaagttgac aagagatctc ttgaattgtt    1500
ccttcaagtg tagctatgtt gtaactaatg gccttgggat taacgtcttc aaggacccag    1560
ttgctgatcc caacaaaagg tccaaaaagg gccgattatc tttacatagg acgccagcag    1620
ggaattttgt tacactggag gaaggaaaag gagaccttga ggaatatggt caggatcttc    1680
tccatactgt cttcaagaat ggcaaggtga caaaaagcta ttcatttgat gaaataagaa    1740
aaaatgcaca gctgaatatt gaactggaag cagcacatca ttaggcttta tgactgggtg    1800
tgtgttgtgt gtatgtaata cataatgttt attgtacaga tgtgtggggt ttgtgttttta   1860 tgatacatta cagccaaatt atttgttggt ttatggacat actgcccttt cattttttt    1920 cttttccagt gtttaggtga tctcaaatta ggaaatgcat ttaaccatgt aaaagatgag    1980
tgctaaagta agcttttag ggcccttttgc caataggtag tcattcaatc tggtattgat    2040
cttttcacaa ataacagaac tgagaaactt ttatatataa ctgatgatca cataaaacag    2100
atttgcataa aattaccatg attgctttat gtttatattt aacttgtatt tttgtacaaa    2160
caagattgtg taagatatat ttgaagtttc agtgatttaa cagtcttttcc aacttttcat   2220 gattttttatg agcacagact ttcaagaaaa tacttgaaaa taaattacat tgccttttgt   2280
ccattaatca gcaaataaaa catggcctta acaaagttgt ttgtgttatt gtacaatttg    2340
aaaattatgt cgggacatac cctatagaat tactaacctt actgcccctt gtagaatatg    2400
tattaatcat tctacattaa agaaaataat ggttcttact ggaatgtcta ggcactgtac    2460
agttattata tatcttggtt gttgtattgt accagtgaaa tgccaaattt gaaaggcctg    2520
tactgcaatt ttatatgtca gagattgcct gtggctctaa tatgcacctc aagatttttaa  2580 ggagataatg ttttttagaga gaatttctgc ttccactata gaatatatac ataaatgtaa   2640
aatacttaca aaagtggaag tagtgtattt taaagtaatt acacttctga atttatttt     2700 catattctat agttggtatg acttaaatga attactggag tgggtagtga gtgtacttaa    2760
atgtttcaat tctgttatat tttttattaa gttttttaaaa aattaaattg gatattaaat   2820
tgtatggaca tcatttatta attttaaact gaatgccctc aataagtaat actgaagcac    2880
attcttaaat gaagataaat tatctccaat gaaaagcatg acatgtgttt caatagaaga    2940
atcttaagtt ggctaaattc aaagtgcttg acatcaaaat gttctagagt gattagctac    3000
tagattctga atcatacatc acatctgact agagaccagt ttctttcgaa tgattctttt    3060
atgtatgtag atctgttctt ctgaggcagc ggttggccaa ctatagccca aaggccaaat    3120
ttggacttct ttttataaat gcagattgtc tatggctgct ttcccactac tccagcctaa    3180
ggtaaacagc tgcaatagaa gccaaatgag aatcgcaaag cccaaaatgt ttattaacct    3240 gcccttaca caaaattaca caaaagtttt cctgatctct gttctaagaa aaggagtgtg     3300
ccttgcattt aaaaggaaat gttggtttct agggaaggga ggaggctaaa taattgatac    3360
ggaattttcc tcttttgtct tcttttttct cacttaagaa tccgatactg gaagactgat    3420
ttagaaaagt ttttaacatg acattaaatg tgaaatttta aaaattgaaa agccataaat    3480
catctgtttt aaatagttac atgagaaaat gatcactaga ataacctaat tagaagtgtt    3540
atcttcatta aatgttttt gtaagtggta ttagaaagaa tatgttttc agatggttct      3600 ttaaacatgt agtgagaaca ataagcatta ttcactttta gtaagtcttc tgtaatccat    3660
gatataaaat aattttaaaa tgattttta atgtatttga gtaaagatga gtagtattaa     3720
gaaaaacaca catttcttca caaaatgtgc taaggggcgt gtaaagaatc aaaagaaact    3780
```

```
attaccaata atagttttga taatcaccca taattttgtg tttaaacatt gaaattatag    3840
tacagacagt attctctgtg ttctgtgaat ttcagcagct tcagaataga gtttaattta    3900
gaaatttgca gtgaaaaaag ctatctcttt gttcacaacc ataaatcagg agatggagat    3960
taattctatt ggctcttagt cacttggaac tgattaattc tgactttctg tcactaagca    4020
cttggtattt ggccatctcc attctgagca ccaaacggtt aacacgaatg tccactagaa    4080
ctctgctgtg tgtcaccctt aaatcagtct aaatcttcca gacaaaagca aatggcattt    4140
atggatttaa gtcattagat tttcaactga cattaattaa tccctcttga ttgattatat    4200
catcaagtat ttatatctta aataggaggt aggatttctg tgttaagact cttatttgta    4260
ccctataatt aaagtaaaat gttttttatg agtatccctt gttttccctt cttaaattgt    4320
tatcaaacaa ttttttataat gaaatctatc ttggaaaatt agaaagaaaa atggcaaggt    4380
atttattgtt ctgtttgcca taatttagaa ctcacactta agtattttgt agttttacat    4440
tcctttttaa cccattcagt ggagaatgtc agcttttctc ccaagttgta tgttaagtct    4500
attctaatat gtactcaaca tcaagttata aacatgtaat aaacatggaa ataaagttta    4560
gctctattag tgaagtgtta aaaaaaaaaa aaa                                 4593

<210> SEQ ID NO 80
<211> LENGTH: 155
<212> TYPE: DNA
<213> ORGANISM: Homo sapiens

<400> SEQUENCE: 80
attgccttcg gttctggtgg aggtttgcta cagaagttga caagagatct cttgaattgt      60
tccttcaagt gtagctatgt tgtaactaat ggccttggga ttaacgtctt caaggaccca    120
gttgctgatc ccaacaaaag gtccaaaaag ggccg                               155
```